United States Patent [19]

Kempf et al.

[11] Patent Number: 5,616,720
[45] Date of Patent: Apr. 1, 1997

[54] RETROVIRAL PROTEASE INHIBITING COMPOUNDS

[75] Inventors: Dale J. Kempf, Libertyville; Daniel W. Norbeck, Crystal Lake; Hing L. Sham; Chen Zhao, both of Gurnee, all of Ill.; Daniel S. Reno, Kenosha, Wis.

[73] Assignee: Abbott Laboratories, Abbott Park, Ill.

[21] Appl. No.: 418,056

[22] Filed: Apr. 6, 1995

Related U.S. Application Data

[60] Division of Ser. No. 158,587, Dec. 2, 1993, abandoned, which is a continuation-in-part of Ser. No. 998,114, Dec. 29, 1992, abandoned, which is a continuation-in-part of Ser. No. 777,626, Oct. 23, 1991, abandoned, which is a continuation-in-part of Ser. No. 746,020, Aug. 15, 1991, abandoned, which is a continuation-in-part of Ser. No. 616,170, Nov. 20, 1990, abandoned, which is a continuation-in-part of Ser. No. 518,730, May 9, 1990, Pat. No. 5,142,056, which is a continuation-in-part of Ser. No. 456,124, Dec. 22, 1989, abandoned, which is a continuation-in-part of Ser. No. 405,604, Sep. 8, 1989, abandoned, which is a continuation-in-part of Ser. No. 355,945, May 23, 1983, abandoned.

[51] Int. Cl.$^6$ ............................................. C07D 277/30
[52] U.S. Cl. ........................... 548/204; 548/214; 548/236; 548/247
[58] Field of Search ........................................... 548/204

[56] References Cited

U.S. PATENT DOCUMENTS

| | | |
|---|---|---|
| 5,142,056 | 8/1992 | Kempf ................................. 546/256 |
| 5,354,866 | 10/1994 | Kempf ................................. 546/256 |

FOREIGN PATENT DOCUMENTS

| | | |
|---|---|---|
| 393445 | 10/1990 | European Pat. Off. . |
| 402646 | 12/1990 | European Pat. Off. . |
| 428849 | 5/1991 | European Pat. Off. . |
| 441192 | 8/1991 | European Pat. Off. . |
| 486948 | 5/1992 | European Pat. Off. . |
| 3829594 | 3/1990 | Germany . |
| 4003575 | 8/1992 | Germany . |
| WO88/02374 | 4/1988 | WIPO . |
| WO92/00948 | 8/1990 | WIPO . |
| WO90/09191 | 8/1990 | WIPO . |
| WO91/18866 | 12/1991 | WIPO . |
| WO92/06996 | 4/1992 | WIPO . |
| WO92/20665 | 11/1992 | WIPO . |
| WO93/01174 | 1/1993 | WIPO . |

*Primary Examiner*—Jane Fan
*Attorney, Agent, or Firm*—Steven R. Crowley

[57] ABSTRACT

A retroviral protease inhibiting compound of the formula:

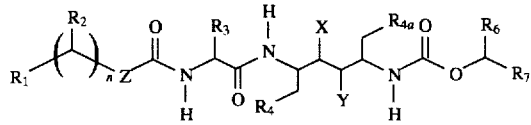

is disclosed.

4 Claims, No Drawings

RETROVIRAL PROTEASE INHIBITING COMPOUNDS

This invention was made with Government support under contract number AI27220 awarded by the National Institute of Allergy and Infectious Diseases. The Government has certain rights in this invention.

This is a division of U.S. patent application Ser. No. 08/158,587, filed Dec. 2, 1993, now abandoned which is a continuation-in-part of U.S. patent application Ser. No. 998,114, filed Dec. 29, 1992, now AB which is a continuation-in-part of U.S. patent application Ser. No. 777,626, filed Oct. 23, 1991, now AB which is a continuation-in-part of U.S. patent application Ser. No. 746,020, filed Aug. 15, 1991, now AB which is a continuation-in-part of U.S. patent application Ser. No. 616,170, filed Nov. 20, 1990, now AB which is a continuation-in-part of U.S. patent application Ser. No. 518,730, filed May 9, 1990, now U.S. Pat. No. 5,142,056 which is a continuation-in-part of U.S. patent application Ser. No. 456,124, filed Dec. 22, 1989, now AB which is a continuation-in-part of U.S. patent application Ser. No. 405,604, filed Sep. 8, 1989, now AB which is a continuation-in-part of U.S. patent application Ser. No. 355,945, filed May 23, 1989 now AB.

TECHNICAL FIELD

The present invention relates to novel compounds and a composition and method for inhibiting retroviral proteases and in particular for inhibiting human immunodeficiency virus (HIV) protease, a composition and method for treating a retroviral infection and in particular an HIV infection, processes for making such compounds and synthetic intermediates employed in these processes.

BACKGROUND OF THE INVENTION

Retroviruses are those viruses which utilize a ribonucleic acid (RNA) intermediate and a RNA-dependent deoxyribonucleic acid (DNA) polymerase, reverse transcriptase, during their life cycle. Retroviruses include, but are not limited to, the RNA viruses of the Retroviridae family, and also the DNA viruses of the Hepadnavirus and Caulimovirus families. Retroviruses cause a variety of disease states in man, animals and plants. Some of the more important retroviruses from a pathological standpoint include human immunodeficiency viruses (HIV-1 and HIV-2), which cause acquired immune deficiency syndrome (AIDS)in man, hepatitis B virus, which causes hepatitis and hepatic carcinomas in man, human T-cell lymphotrophic viruses I, II, IV and V, which cause human acute cell leukemia, and bovine and feline leukemia viruses which cause leukemia in domestic animals.

Proteases are enzymes which cleave proteins at specific peptide bonds. Many biological functions are controlled or mediated by proteases and their complementary protease inhibitors. For example, the protease renin cleaves the peptide angiotensinogen to produce the peptide angiotensin I. Angiotensin I is further cleaved by the protease angiotensin converting enzyme (ACE) to form the hypotensive peptide angiotensin II. Inhibitors of renin and ACE are known to reduce high blood pressure in vivo. An inhibitor of a retroviral protease will provide a therapeutic agent for diseases caused by the retrovirus.

The genomes of retroviruses encode a protease that is responsible for the proteolytic processing of one or more polyprotein precursors such as the pol and gag gene products. See Wellink, Arch. Virol. 98 1 (1988). Retroviral proteases most commonly process the gag precursor into core proteins, and also process the pol precursor into reverse transciptase and retroviral protease. In addition, retroviral proteases are sequence specific. See Pearl, Nature 328 482 (1987).

The correct processing of the precursor polyproteins by the retroviral protease is necessary for the assembly of infectious virions. It has been shown that in vitro mutagenesis that produces protease-defective virus leads to the production of immature core forms which lack infectivity. See Crawford, J. Virol. 53 899 (1985); Katoh, et al., Virology 145 280 (1985). Therefore, retroviral protease inhibition provides an attractive target for antiviral therapy. See Mitsuya, Nature 325 775 (1987).

Current treatments for viral diseases usually involve administration of compounds that inhibit viral DNA synthesis. Current treatments for AIDS involve administration of compounds such as 3'-azido-3'-deoxythymidine (AZT), 2',3'-dideoxycytidine (DDC) and 2',3'-dideoxyinosine (DDI) and compounds which treat the opportunistic infections caused by the immunosuppression resulting from HIV infection. None of the current AIDS treatments have proven to be totally effective in treating and/or reversing the disease. In addition, many of the compounds currently used to treat AIDS cause adverse side effects including low platelet count, renal toxicity and bone marrow cytopenia.

DISCLOSURE OF THE INVENTION

In accordance with the present invention, there are retroviral protease inhibiting compounds of the formula A:

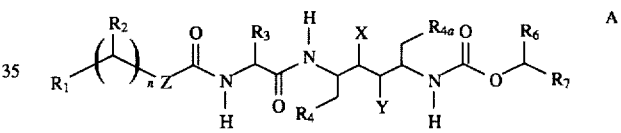

wherein $R_1$ is monosubstituted thiazolyl, monosubstituted oxazolyl, monosubstituted isoxazolyl or monosubstituted isothiazolyl wherein the substituent is selected from (i) loweralkyl, (ii) loweralkenyl, (iii) cycloalkyl, (iv) cycloalkylalkyl, (v) cycloalkenyl, (vi) cycloalkenylalkyl, (vii) heterocyclic wherein the heterocyclic is selected from aziridinyl, azetidinyl, pyrrolidinyl, piperidinyl, piperazinyl, morpholinyl, thiomorpholinyl, thiazolyl, oxazolyl, isoxazolyl, isothiazolyl, pyridinyl, pyrimidinyl, pyridazinyl and pyrazinyl and wherein the heterocyclic is unsubstituted or substituted with a substituent selected from halo, loweralkyl, hydroxy, alkoxy and thioalkoxy, (viii) (heterocyclic)alkyl wherein heterocyclic is defined as above, (ix) alkoxyalkyl, (x) thioalkoxyalkyl, (xi) alkylamino, (xii) dialkylamino, (xiii) phenyl wherein the phenyl ring is unsubstituted or substituted with a substituent selected from halo, loweralkyl, hydroxy, alkoxy and thioalkoxy, (xiv) phenylalkyl wherein the phenyl ring is unsubstituted or substituted as defined above, (xv) dialkylaminoalkyl, (xvi) alkoxy and (xvii) thioalkoxy;

n is 1,2 or 3;

$R_2$ is hydrogen or loweralkyl;

$R_3$ is loweralkyl;

$R_4$ and $R_{4a}$ are independently selected from phenyl, thiazolyl and oxazolyl wherein the phenyl, thiazolyl or oxazolyl ring is unsubstituted or substituted with a substituent selected from (i) halo, (ii) loweralkyl, (iii) hydroxy, (iv) alkoxy and (v) thioalkoxy;

R₆ is hydrogen or loweralkyl;

R₇ is thiazolyl, oxazolyl, isoxazolyl or isothiazolyl wherein the thiazolyl, oxazolyl, isoxazolyl or isothiazolyl ring is unsubstituted or substituted with loweralkyl;

X is hydrogen and Y is —OH or X is —OH and Y is hydrogen, with the proviso that X is hydrogen and Y is —OH when Z is —N(R₈)— and R₇ is unsubstituted and with the proviso that X is hydrogen and Y is —OH when R₃ is methyl and R₇ is unsubstituted; and Z is absent, —O—, —S—, —CH₂— or —N(R₈)— wherein R₈ is loweralkyl, cycloalkyl, —OH or —NHR₈ₐ wherein R₈ₐ is hydrogen, loweralkyl or an N-protecting group; or a pharmaceutically acceptable salt, ester or prodrug thereof.

Preferred compounds of the formula A are those wherein R₁ is monosubstituted thiazolyl or monosubstituted oxazolyl; n is 1; R₂ is hydrogen; R₄ is phenyl or thiazolyl; R₄ₐ is phenyl; R₆ is hydrogen and R₇ is thiazolyl, oxazolyl, isothiazolyl or isoxazolyl.

More preferred compounds of the formula A are those wherein R₁ is 2-monosubstituted-4-thiazolyl or 2-monosubstituted-4-oxazolyl; n is 1; R₂ is hydrogen; R₄ is phenyl; R₄ₐ is phenyl; R₆ is hydrogen and R₇ is 5-thiazolyl, 5-oxazolyl, 5-isothiazolyl or 5-isoxazolyl.

Even more preferred compounds of the formula A are those wherein R₁ is 2-monosubstituted-4-thiazolyl or 2-monosubstituted-4-oxazolyl wherein the substituent is loweralkyl; n is 1; R₂ is hydrogen; R₄ is phenyl; R₄ₐ is phenyl; R₆ is hydrogen; R₇ is 5-thiazolyl, 5-oxazolyl, 5-isothiazolyl or 5-isoxazolyl; and Z is —O— or —N(R₈)— wherein R₈ is loweralkyl.

Most preferred compounds of the formula A are those wherein R₁ is 2-monosubstituted-4-thiazolyl or 2-monosubstituted-4-oxazolyl wherein the substituent is ethyl or isopropyl; n is 1; R₂ is hydrogen; R₃ is methyl or isopropyl; R₄ is phenyl; R₄ₐ is phenyl; R₆ is hydrogen; R₇ is 5-thiazolyl, 5-oxazolyl, 5-isothiazolyl or 5-isoxazolyl; and Z is —O—.

Most preferred compounds of the formula A are also those wherein R₁ is 2-monosubstituted-4-thiazolyl or 2-monosubstituted-4-oxazolyl wherein the substituent is ethyl or isopropyl; n is 1; R₂ is hydrogen; R₃ is isopropyl; R₄ is phenyl; R₄ₐ is phenyl; R₆ is hydrogen; R₇ is 5-thiazolyl, 5-oxazolyl, 5-isothiazolyl or 5-isoxazolyl; and Z is —N(R₈)— wherein R₈ is methyl.

Most preferred compounds of the formula A are also those wherein the configuration of the carbon atom bearing —CH₂R₄ is "S" and the configuration of the carbon bearing X is "S" when X is —OH and the configuration of the carbon atom bearing Y is "S" when Y is —OH and the configuration of the carbon atom bearing —CH₂(R₅-substituted phenyl) is "S".

Preferred compounds of the invention are compounds of the formula A1:

wherein R₁ is monosubstituted thiazolyl, monosubstituted oxazolyl, monosubstituted isoxazolyl or monosubstituted isothiazolyl wherein the substituent is selected from (i) loweralkyl, (ii) loweralkenyl, (iii) cycloalkyl, (iv) cycloalkylalkyl, (v) cycloalkenyl, (vi) cycloalkenylalkyl, (vii) heterocyclic wherein the heterocyclic is selected from aziridinyl, azetidinyl, pyrrolidinyl, piperidinyl, piperazinyl, morpholinyl, thiomorpholinyl, thiazolyl, oxazolyl, isoxazolyl, isothiazolyl, pyridinyl, pyrimidinyl, pyridazinyl and pyrazinyl and wherein the heterocyclic is unsubstituted or substituted with a substituent selected from halo, loweralkyl, hydroxy, alkoxy and thioalkoxy, (viii) (heterocyclic)alkyl wherein heterocyclic is defined as above, (ix) alkoxyalkyl, (x) thioalkoxyalkyl, (xi) alkylamino, (xii) dialkylamino, (xiii) phenyl wherein the phenyl ring is unsubstituted or substituted with a substituent selected from halo, loweralkyl, hydroxy, alkoxy and thioalkoxy, (xiv) phenylalkyl wherein the phenyl ring is unsubstituted or substituted as defined above, (xv) dialkylaminoalkyl, (xvi) alkoxy and (xvii) thioalkoxy;

n is 1,2 or 3;

R₂ is hydrogen or loweralkyl;

R₃ is loweralkyl;

R₄ is phenyl, thiazolyl or oxazolyl wherein the phenyl, thiazolyl or oxazolyl ring is unsubstituted or substituted with a substituent selected from (i) halo, (ii) loweralkyl, (iii) hydroxy, (iv) alkoxy and (v) thioalkoxy;

R₅ is hydrogen, halo, loweralkyl, hydroxy, alkoxy or thioalkoxy;

R₆ is hydrogen or loweralkyl;

R₇ is thiazolyl, oxazolyl, isoxazolyl or isothiazolyl wherein the thiazolyl, oxazolyl, isoxazolyl or isothiazolyl ring is unsubstituted or substituted with loweralkyl;

X is hydrogen and Y is —OH or X is —OH and Y is hydrogen, with the proviso that X is hydrogen and Y is —OH when Z is —N(R₈)— and R₇ is unsubstituted and with the proviso that X is hydrogen and Y is —OH when R₃ is methyl and R₇ is unsubstituted;

Z is absent, —O—, —S—, —CH₂— or —N(R₈)— wherein R₈ is loweralkyl, cycloalkyl, —OH or —NHR₈ₐ wherein R₈ₐ is hydrogen, loweralkyl or an N-protecting group; or a pharmaceutically acceptable salt, ester or prodrug thereof.

Preferred compounds of the formula A1 are those wherein R₁ is monosubstituted thiazolyl or monosubstituted oxazolyl; n is 1; R₂ is hydrogen; R₄ is phenyl or thiazolyl; R₅ is hydrogen; R₆ is hydrogen and R₇ is thiazolyl, oxazolyl, isothiazolyl or isoxazolyl.

More preferred compounds of the formula A1 are those wherein R₁ is 2-monosubstituted-4-thiazolyl or 2-monosubstituted-4-oxazolyl; n is 1; R₂ is hydrogen; R₄ is phenyl; R₅ is hydrogen; R₆ is hydrogen and R₇ is 5-thiazolyl, 5-oxazolyl, 5-isothiazolyl or 5-isoxazolyl.

Even more preferred compounds of the formula A1 are those wherein R₁ is 2-monosubstituted-4-thiazolyl or 2-monosubstituted-4-oxazolyl wherein the substituent is loweralkyl; n is 1; R₂ is hydrogen; R₄ is phenyl; R₅ is hydrogen; R₆ is hydrogen; R₇ is 5-thiazolyl, 5-oxazolyl, 5-isothiazolyl or 5-isoxazolyl; and Z is —O— or —N(R₈)— wherein R₈ is loweralkyl.

Most preferred compounds of the formula A1 are those wherein R₁ is 2-monosubstituted-4-thiazolyl or 2-monosubstituted-4-oxazolyl wherein the substituent is ethyl or isopropyl; n is 1; R₂ is hydrogen; R₃ is methyl or isopropyl; R₄ is phenyl; R₅ is hydrogen; R₆ is hydrogen; R₇ is 5-thiazolyl, 5-oxazolyl, 5-isothiazolyl or 5-isoxazolyl; and Z is —O—.

Most preferred compounds of the formula A1 are also those wherein R₁ is 2-monosubstituted-4-thiazolyl or 2-monosubstituted-4-oxazolyl wherein the substituent is ethyl or isopropyl; n is 1; R₂ is hydrogen; R₃ is isopropyl;

$R_4$ is phenyl; $R_5$ is hydrogen; $R_6$ is hydrogen; $R_7$ is 5-thiazolyl, 5-oxazolyl, 5-isothiazolyl or 5-isoxazolyl; and Z is —N($R_8$)— wherein $R_8$ is methyl.

Most preferred compounds of the formula A1 are also those wherein X is hydrogen and Y is —OH.

Most preferred compounds of the formula A1 are also those wherein the configuration of the carbon atom bearing —$CH_2R_4$ is "S" and the configuration of the carbon bearing X is "S" when X is —OH and the configuration of the carbon atom bearing Y is "S" when Y is —OH and the configuration of the carbon atom bearing —$CH_2(R_5$-substituted phenyl) is "S".

In accordance with the present invention, there are also retroviral protease inhibiting compounds of the formula A2:

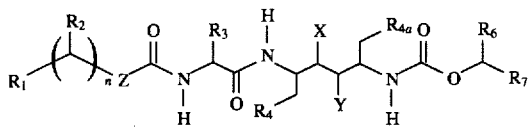

wherein $R_1$ is monosubstituted thiazolyl, monosubstituted oxazolyl, monosubstituted isoxazolyl or monosubstituted isothiazolyl wherein the substituent is selected from (i) loweralkyl, (ii) loweralkenyl, (iii) cycloalkyl, (iv) cycloalkylalkyl, (v) cycloalkenyl, (vi) cycloalkenylalkyl, (vii) heterocyclic wherein the heterocyclic is selected from aziridinyl, azetidinyl, pyrrolidinyl, piperidinyl, piperazinyl, morpholinyl, thiomorpholinyl, thiazolyl, oxazolyl, isoxazolyl, isothiazolyl, pyridinyl, pyrimidinyl, pyridazinyl and pyrazinyl and wherein the heterocyclic is unsubstituted or substituted with a substituent selected from halo, loweralkyl, hydroxy, alkoxy and thioalkoxy, (viii) (heterocyclic)alkyl wherein heterocyclic is defined as above, (ix) alkoxyalkyl, (x) thioalkoxyalkyl, (xi) alkylamino, (xii) dialkylamino, (xiii) phenyl wherein the phenyl ring is unsubstituted or substituted with a substituent selected from halo, loweralkyl, hydroxy, alkoxy and thioalkoxy, (xiv) phenylalkyl wherein the phenyl ring is unsubstituted or substituted as defined above, (xv) dialkylaminoalkyl, (xvi) alkoxy and (xvii) thioalkoxy;

n is 1,2 or 3;

$R_2$ is hydrogen or loweralkyl;

$R_3$ is loweralkyl;

$R_4$ and $R_{4a}$ are independently selected from phenyl, thiazolyl and oxazolyl wherein the phenyl, thiazolyl or oxazolyl ring is unsubstituted or substituted with a substituent selected from
(i) halo, (ii) loweralkyl, (iii) hydroxy, (iv) alkoxy and (v) thioalkoxy;

$R_6$ is hydrogen or loweralkyl;

$R_7$ is thiazolyl, oxazolyl, isoxazolyl or isothiazolyl wherein the thiazolyl, oxazolyl, isoxazolyl or isothiazolyl ring is unsubstituted or substituted with loweralkyl;

X is —OH and Y is —OH; and

Z is absent, —O—, —S—, —$CH_2$— or —N($R_8$)— wherein $R_8$ is loweralkyl, cycloalkyl, —OH or —NH$R_{8a}$ wherein $R_{8a}$ is hydrogen, loweralkyl or an N-protecting group; or a pharmaceutically acceptable salt, ester or prodrug thereof.

Preferred compounds of the formula A2 are those wherein $R_1$ is monosubstituted thiazolyl or monosubstituted oxazolyl; n is 1; $R_2$ is hydrogen; $R_4$ is phenyl or thiazolyl; $R_{4a}$ is phenyl; $R_6$ is hydrogen and $R_7$ is thiazolyl, oxazolyl, isothiazolyl or isoxazolyl.

More preferred compounds of the formula A2 are those wherein $R_1$ is 2-monosubstituted-4-thiazolyl or 2-monosubstituted-4-oxazolyl; n is 1; $R_2$ is hydrogen; $R_4$ is phenyl; $R_{4a}$ is phenyl; $R_6$ is hydrogen and $R_7$ is 5-thiazolyl, 5-oxazolyl, 5-isothiazolyl or 5-isoxazolyl.

Even more preferred compounds of the formula A2 are those wherein $R_1$ is 2-monosubstituted-4-thiazolyl or 2-monosubstituted-4-oxazolyl wherein the substituent is loweralkyl; n is 1; $R_2$ is hydrogen; $R_4$ is phenyl; $R_{4a}$ is phenyl; $R_6$ is hydrogen; $R_7$ is 5-thiazolyl, 5-oxazolyl, 5-isothiazolyl or 5-isoxazolyl; and Z is —O— or —N($R_8$)— wherein $R_8$ is loweralkyl.

Preferred compounds of the formula A2 are also those wherein the configuration of the carbon atom bearing —$CH_2R_4$ is "S" and the configuration of the carbon atom bearing —$CH_2(R_5$-substituted phenyl) is "S".

The compounds of the invention comprise asymmetrically substituted centers (i.e., asymmetrically substituted carbon atoms). The present invention is intended to include all stereoiosomeric forms of the compounds, including racemic mixtures, mixtures of diastereomers, as well as single diastereomers of the compounds of the invention. The terms "S" and "R" configuration are as defined by the IUPAC 1974 Recommendations for Section E, Fundamental Stereochemistry, Pure Appl. Chem. (1976) 45, 13–30.

The terms "Val" and "Ala" as used herein refer to valine and alanine, respectively. Unless otherwise noted, when "Val" and "Ala" are used herein they refer to the L-isomer. In general, the amino acid abbreviations used herein follow the IUPAC-IUB Joint Commission on Biochemical Nomenclature for amino acids and peptides (Eur. J. Blochem. 1984, 158, 9–31).

The term "N-protecting group" or "N-protected" as used herein refers to those groups intended to protect the N-terminus of an amino acid or peptide or to protect an amino group against undersirable reactions during synthetic procedures. Commonly used N-protecting groups are disclosed in Greene, "Protective Groups In Organic Synthesis," (John Wiley & Sons, New York (1981)), which is hereby incorporated by reference. N-protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, triphenylmethyl, benzyloxymethyl and the like; and silyl groups such as trimethylsilyl and the like. Preferred N-protecting groups are formyl, acetyl, benzoyl, pivaloyl, t-butylacetyl, phenylsulfonyl, benzyl, t-butyloxycarbonyl (Boc) and benzyloxycarbonyl (Cbz).

The term "O-protecting group" as used herein refers to a substituent which protects hydroxyl groups against undesirable reactions during synthetic procedures such as those O-protecting groups disclosed in Greene, "Protective Groups In Organic Synthesis," (John Wiley & Sons, New York (1981)). O-protecting groups comprise substituted methyl ethers, for example, methoxymethyl, benzyloxymethyl, 2-methoxyethoxymethyl, 2-(trimethylsilyl)ethoxymethyl, t-butyl, benzyl and triphenylmethyl; tetrahydropyranyl ethers; substituted ethyl ethers, for example, 2,2,2-trichloroethyl; silyl ethers, for example, trimethylsilyl, t-butyldimethylsilyl and t-butyldiphenylsilyl; and esters prepared by reacting the hydroxyl group with a carboxylic acid, for example, acetate, propionate, benzoate and the like.

The term "loweralkyl" as used herein refers to straight or branched chain alkyl radicals containing from 1 to 6 carbon atoms including, but not limited to, methyl, ethyl, n-propyl, iso-propyl, n-butyl, iso-butyl, sec-butyl, n-pentyl, 1-methylbutyl, 2,2-dimethylbutyl, 2-methylpentyl, 2,2-dimethylpropyl, n-hexyl and the like.

The term "loweralkenyl" as used herein refers to a straight or branched chain alkyl radical containing from 2 to 6 carbon atoms and also having one carbon-carbon double bond including, but not limited to, vinyl, 2-propenyl, 2-methyl-2-propenyl, 3-butenyl, 4-pentenyl, 5-hexenyl and the like.

The term "phenyl" as used herein refers to a phenyl group which is unsubstituted or substituted with a substituent selected from loweralkyl, alkoxy, thioalkoxy, hydroxy and halo.

The term "phenylalkyl" as used herein refers to an phenyl group appended to a loweralkyl radical including, but not limited to, benzyl, 4-hydroxybenzyl, 4-chlorobenzyl, 1-naphthylmethyl and the like.

The term "alkylamino" as used herein refers to a loweralkyl radical appended to an —NH radical.

The term "cycloalkyl" as used herein refers to an aliphatic ring having 3 to 7 carbon atoms including, but not limited to, cyclopropyl, cyclopentyl, cyclohexyl and the like. A preferred cycloalkyl group is cyclopropyl The term "cycloalkylalkyl" as used herein refers to a cycloalkyl group appended to a loweralkyl radical, including but not limited to cyclohexylmethyl.

The term "cycloalkenyl" as used herein refers to to an aliphatic ring having 5 to 7 carbon atoms and also having one carbon-carbon double bond including, but not limited to, cyclopentenyl, cyclohexenyl and the like.

The term "cycloalkenylalkyl" as used herein refers to a cycloalkenyl group appended to a loweralkyl radical including, but not limited to, cyclopentenylmethyl, cyclohexenylmethyl and the like.

The terms "alkoxy" and "thioalkoxy" as used herein refer to $R_{15}O$— and $R_{15}S$—, respectively, wherein $R_{15}$ is a loweralkyl group or benzyl.

The term "alkoxyalkyl" as used herein refers to an alkoxy group appended to a loweralkyl radical.

The term "thioalkoxyalkyl" as used herein refers to a thioalkoxy group appended to a loweralkyl radical.

The term "dialkylamino" as used herein refers to —$NR_{16}R_{17}$ wherein $R_{16}$ and $R_{17}$ are independently selected from loweralkyl groups.

The term "dialkylaminoalkyl" as used herein refers to —$NR_{18}R_{19}$ which is appended to a loweralkyl radical wherein $R_{18}$ and $R_{19}$ are independently selected from loweralkyl.

The term "halo" or "halogen" as used herein refers to —Cl, —Br, —I or —F.

The term "heterocyclic" as used herein refers to a heterocyclic group selected from aziridinyl, azetidinyl, pyrrolidinyl, piperidinyl, piperazinyl, morpholinyl, thiomorpholinyl, thiazolyl, oxazolyl, isoxazolyl, isothiazolyl, pyridinyl, pyrimidinyl, pyridazinyl and pyrazinyl and wherein the heterocyclic is unsubstituted or substituted with a substituent selected from halo, loweralkyl, hydroxy, alkoxy and thioalkoxy.

The term "(heterocyclic)alkyl" as used herein refers to a heterocyclic group appended to a loweralkyl radical including, but not limited to, pyrrolidinylmethyl and morpholinylmethyl.

The term "activated ester derivative" as used herein refer to acid halides such as acid chlorides, and activated esters including, but not limited to, formic and acetic acid derived anhydrides, anhydrides derived from alkoxycarbonyl halides such as isobutyloxycarbonylchloride and the like, N-hydroxysuccinimide derived esters, N-hydroxyphthalimide derived esters, N-hydroxybenzotriazole derived esters, N-hydroxy-5-norbornene-2,3-dicarboxamide derived esters, 2,4,5-trichlorophenol derived esters and the like.

In the compounds of the invention, combinations of substituents and/or variables are permissible only if such combinations result in stable compounds. As used herein, the term "stable compound" refers to a compound that is sufficiently stable to survive isolation to a useful degree of purity from a reaction mixture and formulation into a therapeutic dosage form suitable for administration.

Preferred compounds of the invention are selected from the group consisting of:

(2S,3S,5S)-5-(N-(N-((N-Methyl-N-((2-isopropyl-4-thiazolyl)methyl)amino)carbonyl)valinyl)amino)-2-(N-((5-thiazolyl)methoxycarbonyl)amino)-1,6-diphenyl-3-hydroxyhexane;

(2S,3S,5S)-5-(N-(N-((N-Methyl-N-((2-isopropyl-4-thiazolyl)methyl)amino)carbonyl)alaninyl)amino)-2-(N-((5-thiazolyl)methoxycarbonyl)amino)-1,6-diphenyl-3-hydroxyhexane;

(2S,3S,5S)-5-(N-(N-((2-Isopropyl-4-thiazolyl)methoxycarbonyl)valinyl)amino)-2-(N-((5-thiazolyl)methoxycarbonyl)amino)-1,6-diphenyl-3-hydroxyhexane;

(2S,3S,5S)-2-(N-(N-((2-Isopropyl-4-thiazolyl)methoxycarbonyl)valinyl)amino)-5-(N-((5-thiazolyl)methoxycarbonyl)amino)-1,6-diphenyl-3-hydroxyhexane;

(2S,3S,5S)-5-(N-(N-((2-Isopropyl-4-thiazolyl)methoxycarbonyl)alaninyl)amino)-2-(N-((5-thiazolyl)methoxycarbonyl)amino)-1,6-diphenyl-3-hydroxyhexane;

(2S,3S,5S)-5-(N-(N-((2-(N,N-Dimethylamino)-4-thiazolyl)methoxycarbonyl)valinyl)amino)-2-(N-((5-thiazolyl)methoxycarbonyl)amino)-1,6-diphenyl-3-hydroxyhexane;

(2S,3S,5S)-2-(N-(N-((2-(N,N-Dimethylamino)-4-thiazolyl)methoxycarbonyl)valinyl)amino)-5-(N-((5-thiazolyl)methoxycarbonyl)amino)-1,6-diphenyl-3-hydroxyhexane;

(2S,3S,5S)-5-(N-(N-((2-(4-Morpholinyl)-4-thiazolyl)methoxycarbonyl)valinyl)amino)-2-(N-((5-thiazolyl)methoxycarbonyl)amino)-1,6-diphenyl-3-hydroxyhexane;

(2S,3S,5S)-2-(N-(N-((2-(4-Morpholinyl)-4-thiazolyl)methoxycarbonyl)valinyl)-amino)-5-(N-((5-thiazolyl)methoxycarbonyl)amino)-1,6-diphenyl-3-hydroxyhexane;

(2S,3S,5S)-5-(N-(N-((2-(1-Pyrrolidinyl)-4-thiazolyl)methoxycarbonyl)valinyl)amino)-2-(N-((5-thiazolyl)methoxycarbonyl)amino)-1,6-diphenyl-3-hydroxyhexane;

(2S,3S,5S)-5-(N-(N-((N-Methyl-N-((2-isopropyl-4-oxazolyl)methyl)amino)carbonyl)valinyl)amino)-2-(N-((5-thiazolyl)methoxycarbonyl)amino)-1,6-diphenyl-3-hydroxyhexane;

(2S,3S,5S)-5-(N-(N-((N-Methyl-N-((2-isopropyl-4-oxazolyl)methyl)amino)carbonyl)valinyl)amino)-2-(N-((5-oxazolyl)methoxycarbonyl)amino)-1,6-diphenyl-3-hydroxyhexane;

(2S,3S,5S)-5-(N-(N-((N-Methyl-N-((2-isopropyl-4-thiazolyl)methyl)amino)carbonyl)valinyl)amino)-2-(N-((5-oxazolyl)methoxycarbonyl)amino)-1,6-diphenyl-3-hydroxyhexane;

(2S,3S,5S)-5-(N-(N-((N-Methyl-N-((2-isopropyl-4-thiazolyl)methyl)amino)carbonyl)valinyl)amino)-2-(N-((5-isoxazolyl)methoxycarbonyl)amino)-1,6-diphenyl-3-hydroxyhexane; and (2S,3S,5S)-5-(N-(N-((N-Methyl-N-((2-isopropyl-4-oxazolyl)methyl)amino)carbonyl)valinyl)amino)-2-(N-((5-isoxazolyl)methoxycarbonyl)amino)-1,6-diphenyl-3-hydroxyhexane;

or a pharmaceutically acceptable salt, ester or prodrug thereof.

Compounds useful as intermediates for the preparation of the compound of formula A and A1 include the compound of the formula A3:

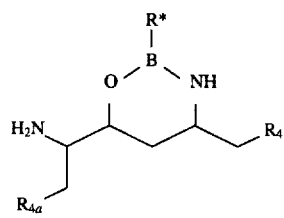

wherein $R_4$ and $R_{4a}$ are independently selected from phenyl, thiazolyl and oxazolyl wherein the phenyl, thiazolyl or oxazolyl ring is unsubstituted or substituted with a substituent selected from (i) halo, (ii) loweralkyl, (iii) hydroxy, (iv) alkoxy and (v) thioalkoxy; and R* is phenyl, halo-substituted phenyl, dihalo-substituted phenyl, alkoxy-substituted phenyl, loweralkyl-substituted phenyl, bis-trifluormethyl-substituted phenyl or naphthyl or loweralkyl; or an acid addition salt thereof.

Preferred intermediates are compounds of the formula A4:

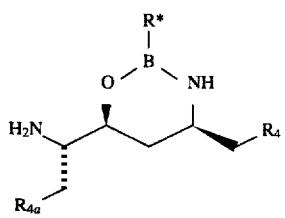

wherein $R_4$ and $R_{4a}$ are independently selected from phenyl, thiazolyl and oxazolyl wherein the phenyl, thiazolyl or oxazolyl ring is unsubstituted or substituted with a substituent selected from (i) halo, (ii) loweralkyl, (iii) hydroxy, (iv) alkoxy and (v) thioalkoxy; and R* is phenyl, halo-substituted phenyl, dihalo-substituted phenyl, alkoxy-substituted phenyl, loweralkyl-substituted phenyl, bis-trifluormethyl-substituted phenyl or naphthyl or loweralkyl; or an acid addition salt thereof.

Preferred compounds of the formula A4 are those wherein $R_{4a}$ is phenyl and R* is phenyl. Most preferred compounds of the formula A4 are those wherein $R_4$ and $R_{4a}$ are phenyl and R* is phenyl.

The compounds of the invention can be prepared as shown in Schemes 1–9. As outlined in Scheme 1, coupling of protected α-aminoaldehyde Ia and Ib ($R_{30}$ is loweralkyl or benzyl) with VCl$_3$(tetrahydrofuran)$_3$ and Zn produces a mixture of diols, out of which compounds II and III can be isolated. Hydrolysis of II and III with barium hydroxide leads, respectively, to diaminodiols IV and V. Alternately, treatment of II with α-acetoxyisobutyryl bromide in acetonitrile leads to compound VI, which upon hydrolysis with barium hydroxide, produces diaminodiol VII. In a preferred embodiment, $R_4$ and $R_{4a}$ are each phenyl and the first reaction in Scheme 1 is a dimerization.

Scheme 1

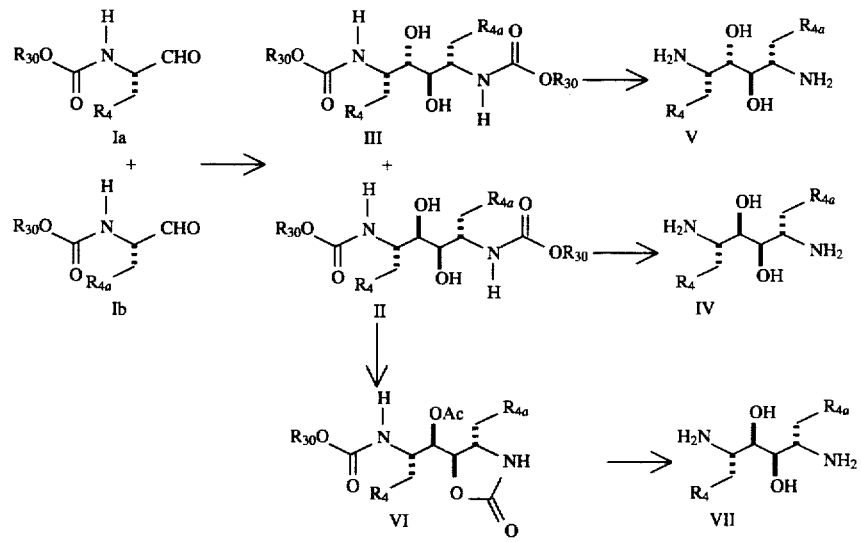

As outlined in Scheme 2, treatment of compound II with α-acetoxyisobutyryl bromide in hexane/dichloromethane produces bromoacetate VIII. Hydrolysis of VIII with concomitant cyclization produces epoxide IX, which is reduced with sodium borohydride and trifluoroacetic acid to produce compound X. Barium hydroxide hydrolysis of X leads to diamine XI.

azide undergoes a Curtius rearrangement. The intermediate isocyanate is trapped with benzyl alcohol to produce com-

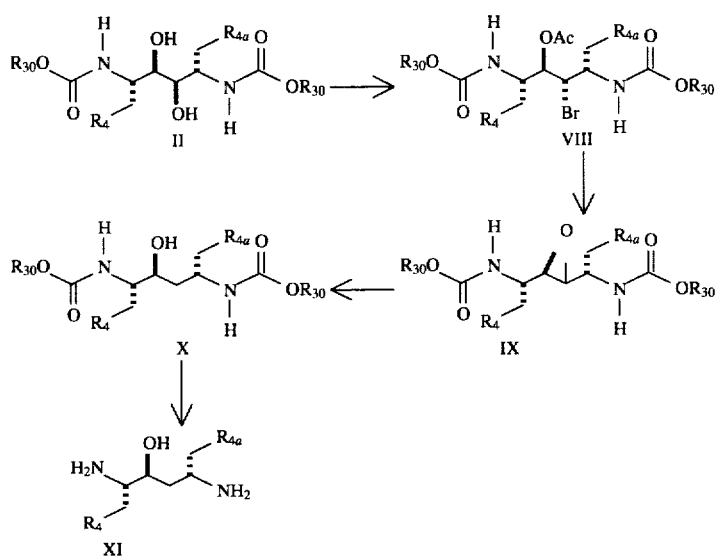

Scheme 2

As outlined in Scheme 3, acylation of the enolate derived from compound XII with ethyl chloroformate gives compound XIII. Subsequent alkylation of the enolate prepared from XIII provides compound XIV ($R_{4a}$ is thiazolyl), which is hydrolyzed and decarboxylated to lactone XV. Hydrolysis of XV and protection of the hydroxyl group leads to compound XVI, which, upon treatment with diphenylphosphoryl pound XVII. Desilylation of XVII with tetrabutylammonium fluoride provides compound XVIII, which is deprotected with HBr to give diamine XIX.

In a preferred embodiment of the process shown in Scheme 3, $R_4$ is phenyl.

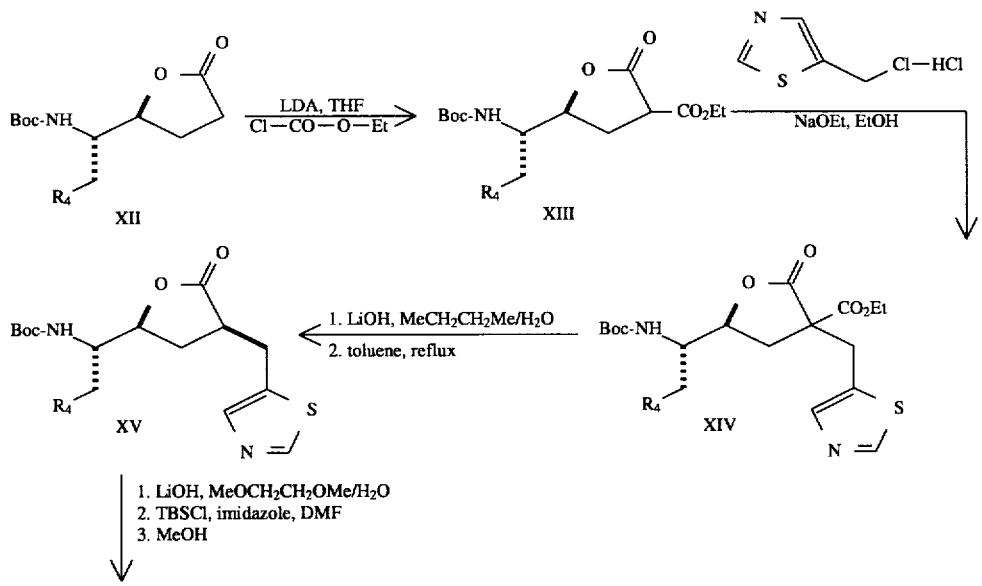

Scheme 3

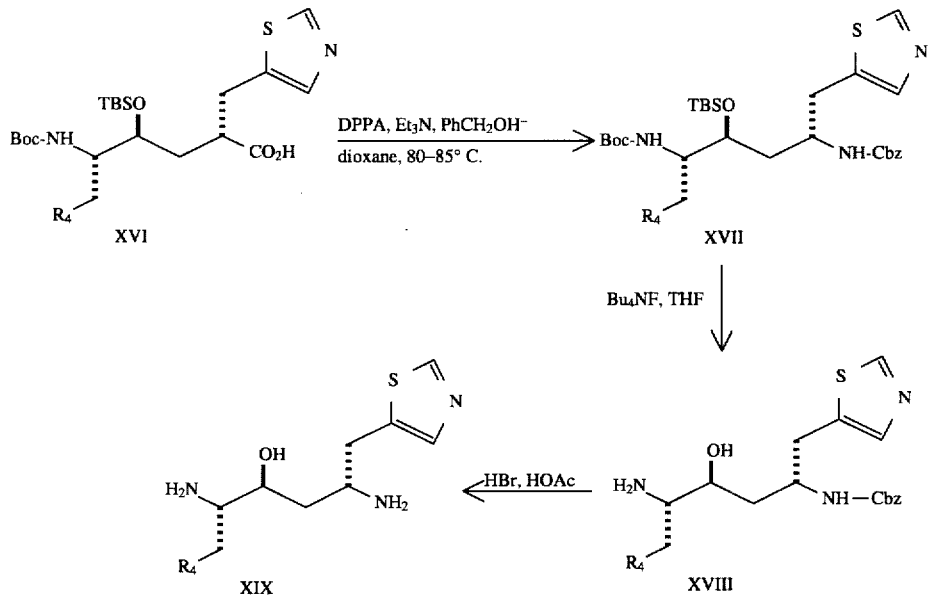

As outlined in Scheme 4, compound XX (R₃ is lower-alkyl) is converted to isocyanate XXI by treatment with phosgene. Alternatively, treatment of XX with 4-nitrophenyl chloroformate produces carbamate XXII. Condensation of either XXI or XXII with compound XXIII wherein Z is O, S or N(R₈), with catalytic 4-dimethylaminopyridine as needed, provides compound XXIV. Lithium hydroxide hydrolysis of XXIV produces compound XXV. In a preferred embodiment of the process shown in Scheme 4, n is 1.

an activated derivative of XXVI having the formula (R₆)(R₇)CHOC(O)OL wherein L is an activating group for the acylation reaction such as p-nitrophenyl, phenyl, N-succinimidyl, N-phthalimidyl, N-benzotriazolyl, N-5-norbornene-2,3-carboxamidyl or 2,4,5-trichlorophenyl and the like (for example, XXVII, which is prepared by reacting XXVI with 4-nitrophenyl chloroformate) to provide a mixture of compounds XXIXa and XXIXb or an acid addition salt thereof. Coupling of XXIXa or XXIXb to compound XXX by treatment with a carbodiimide (or by reaction with

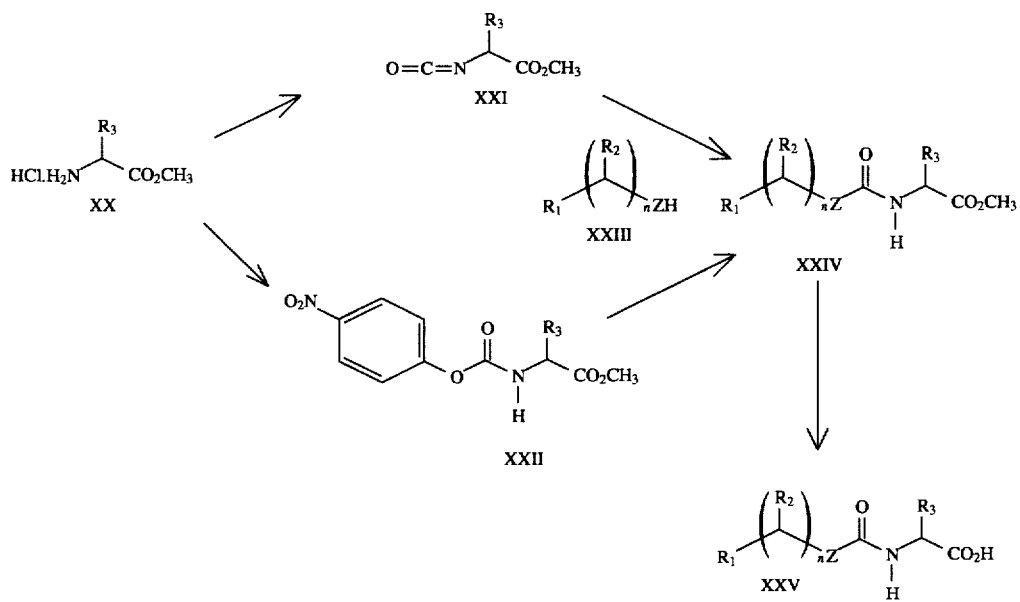

As outlined in Scheme 5, compound XXVIII, which represents diamines IV, V, VII, XI and XIX, is acylated with an activated ester of XXX) produces compound XXXIa or XXXIb, respectively. In a preferred embodiment of the process shown in Scheme 5, n is 1, $R_4$ and $R_{4a}$ are each phenyl, X is H and Y is OH.

shown in Scheme 6A, n is 1, $R_4$ and $R_{4a}$ are each phenyl and R* is phenyl.

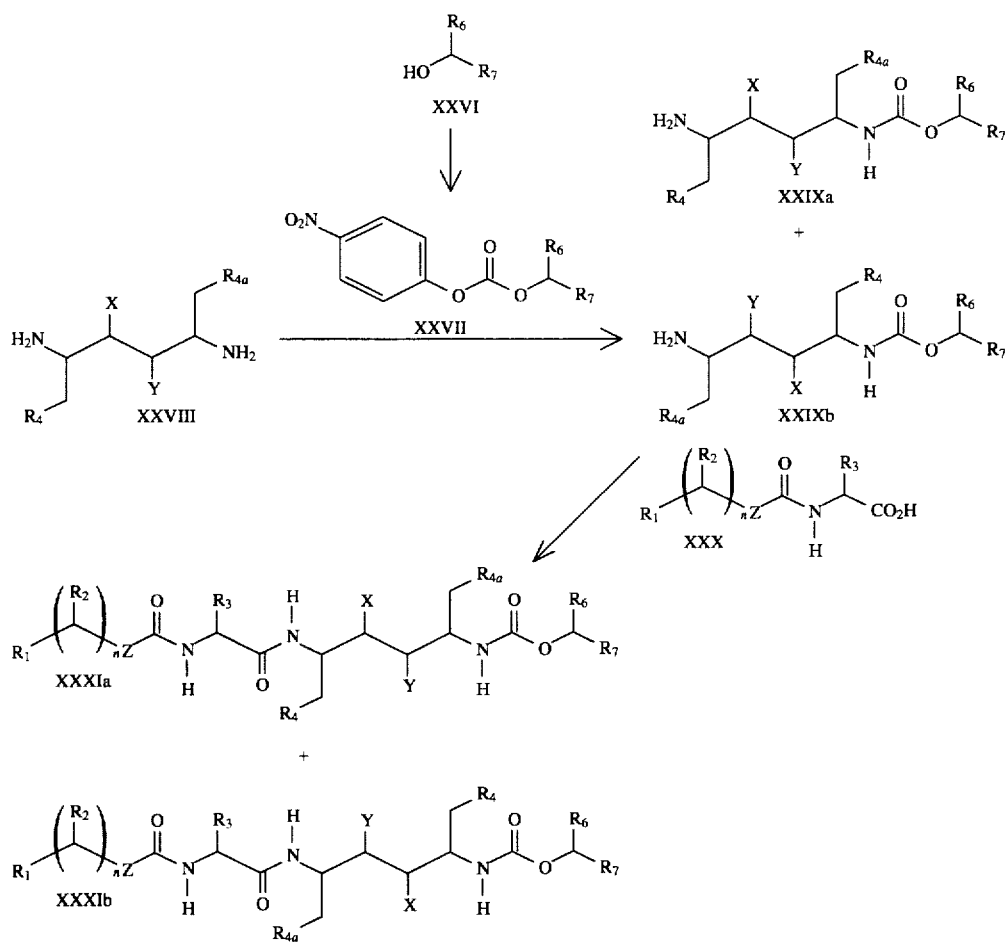

Scheme 5

As outlined in Scheme 6A, treatment of diamine XI with a boronic acid (preferably, phenylboronic acid) or a boroxine produces compound XXXII, which is selectively acylated with an activated derivative of XXVI having the formula $(R_6)(R_7)CHOC(O)OL$ wherein L is an activating group for the acylation reaction such as p-nitrophenyl, phenyl, N-succinimidyl, N-phthalimidyl, N-benzotriazolyl, N-5-norbornene-2,3-carboxamidyl or 2,4,5-trichlorophenyl and the like (for example, XXVII) to provide compound XXXIIIa or an acid addition salt thereof. Carbodiimide-mediated coupling of XXXIIIa to compound XXX (or reaction of XXXIIIa with an activated ester of XXX) leads to compound XXXIVa. In a preferred embodiment of the process Alternatively, compound XXXII can be acylated with compound XXX (or an activated ester thereof) to provide compound XXXIIIb or an acid addition salt thereof. Acylation of compound XXXIIIb with an activated derivative of XXVI having the formula $(R_6)(R_7)CHOC(O)OL$ wherein L is an activating group for the acylation reaction such as p-nitrophenyl, phenyl, N-succinimidyl, N-phthalimidyl, N-benzotriazolyl, N-5-norbornene-2,3-carboxamidyl or 2,4,5-trichlorophenyl and the like (for example, XXVII) provides compound XXXIVb.

Scheme 6A

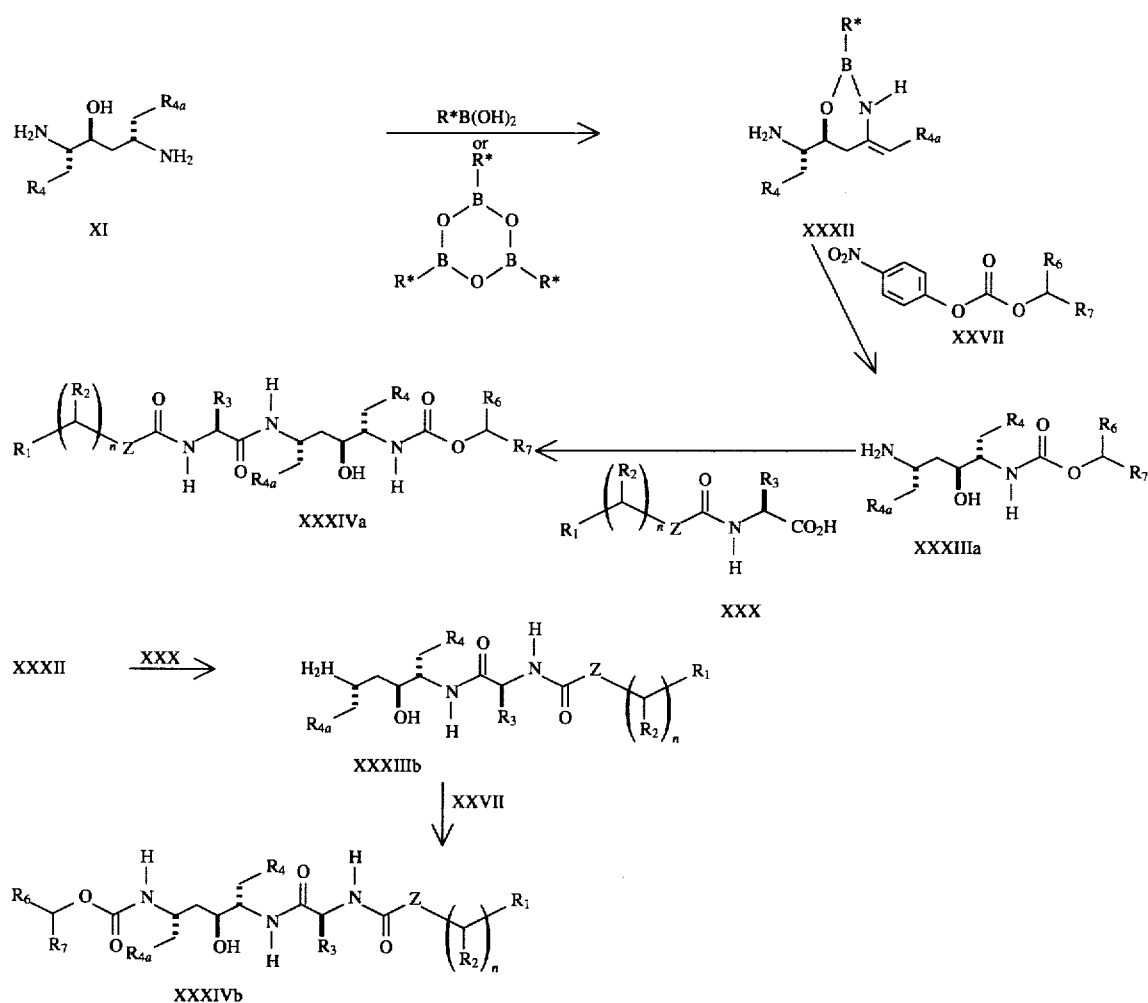

Scheme 6B outlines an alternative preparation of XXXIIIa or XXXIIIb. Reaction of compound XI with (i) two equivalents of B(OR)$_3$ wherein R is loweralkyl (preferably, isopropyl) or (ii) two equivalents of B(R*)$_3$ wherein R* is halo (preferably, fluoro) and four equivalents of an amine such as triethylamine in an inert solvent such as tetrahydrofuran, followed by reaction with an activated derivative of XXVI having the formula (R$_6$)(R$_7$)CHOC(O)OL wherein L is an activating group for the acylation reaction such as p-nitrophenyl, phenyl, N-succinimidyl, N-phthalimidyl, N-benzotriazolyl, N-5-norbornene-2,3-carboxamidyl or 2,4,5-trichlorophenyl and the like (for example, XXVII), gives compound XXXIIIa or an acid addition salt thereof. Similarly, reaction of compound XI with two equivalents of B(OR)$_3$ wherein R is loweralkyl (preferably, isopropyl) or two equivalents of B(R*)$_3$ wherein R* is halo (preferably, fluoro), followed by reaction with compound XXX (or an activated ester derivative thereof), gives compound XXXIIIb or an acid addition salt thereof. In the preferred embodiment of the process shown in Scheme 6B, n is 1, R$_4$ and R$_{4a}$ are each phenyl and R is isopropyl or R* is fluoro.

Scheme 6B

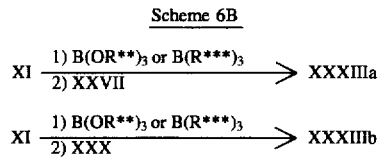

Scheme 6C outlines an alternative preparation of XXXIVa and XXXIVb. Reaction of compound XI with two molar equivalents of Ti(OR**)$_4$ wherein R$_4$ is loweralkyl (preferably, isopropyl), followed by reaction with an activated derivative of XXVI having the formula (R$_6$)(R$_7$)CHOC(O)OL wherein L is an activating group for the acylation reaction such as p-nitrophenyl, phenyl, N-succinimidyl, N-phthalimidyl, N-benzotriazolyl, N-5-norbornene-2,3-carboxamidyl or 2,4,5-trichlorophenyl and the like (for example, XXVII), provides compound XLII or an acid addition salt thereof. Reaction of compound XLII with compound XXX (or an activated ester derivative thereof) gives compound XXXIVb. Similarly, reaction of compound XI with two molar equivalents of Ti(OR)$_4$ wherein R$_4$ is loweralkyl (preferably, isopropyl), followed by reaction with compound XXX (or an activated ester derivative thereof), provides compound XLIII or an acid addition salt thereof. Reaction of compound XLIII with an activated derivative of XXVI having the formula (R₆)(R₇)CHOC(O)OL wherein L is an activating group for the acylation reaction such as p-nitrophenyl, phenyl, N-succinimidyl, N-phthalimidyl, N-benzotriazolyl, N-5-norbornene-2,3-carboxamidyl or 2,4,5-trichlorophenyl and the like (for example, XXVII) gives compound XXXIVa. In the preferred embodiment of the process shown in Scheme 6C, n is 1, R₄ and R₄ₐ are each phenyl and R** is isopropyl.

Scheme 6C

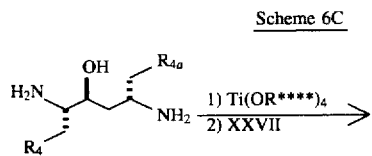

XI

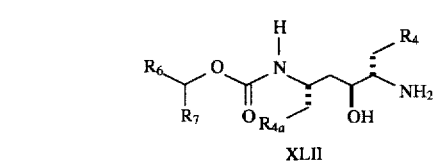

XLII

↓ XXX

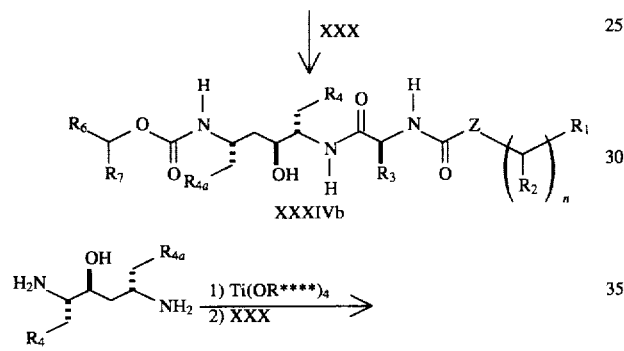

XXXIVb

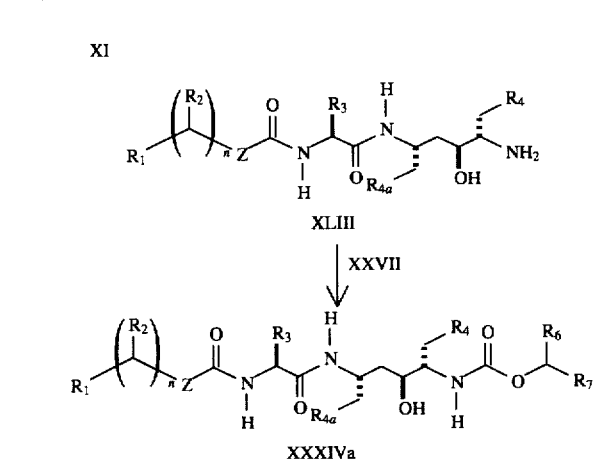

XLIII

↓ XXVII

XXXIVa

Scheme 7 shows an alternative preparation of diamino-mono-ol XI. Reaction of ketonitrile XXXV with Grignard reagent R₄ₐCH₂MgX provides ketoenamine XXXVI. Reaction of the ketoenamine with NaBH₄/CH₃SO₃H, followed by reaction of the resulting intermediate (without isolation) with NaBH₄/CF₃CO₂H, provides XXXVII. Hydrogenation of the benzyl groups gives XI. Alternatively, protection of the free amino group of XXXVII as the t-butyloxycarbonylamino group, followed by hydrogenation of the benzyl groups, gives XXXVIII. In a preferred embodiment, R₄ and R₄ₐ are each phenyl.

Scheme 7

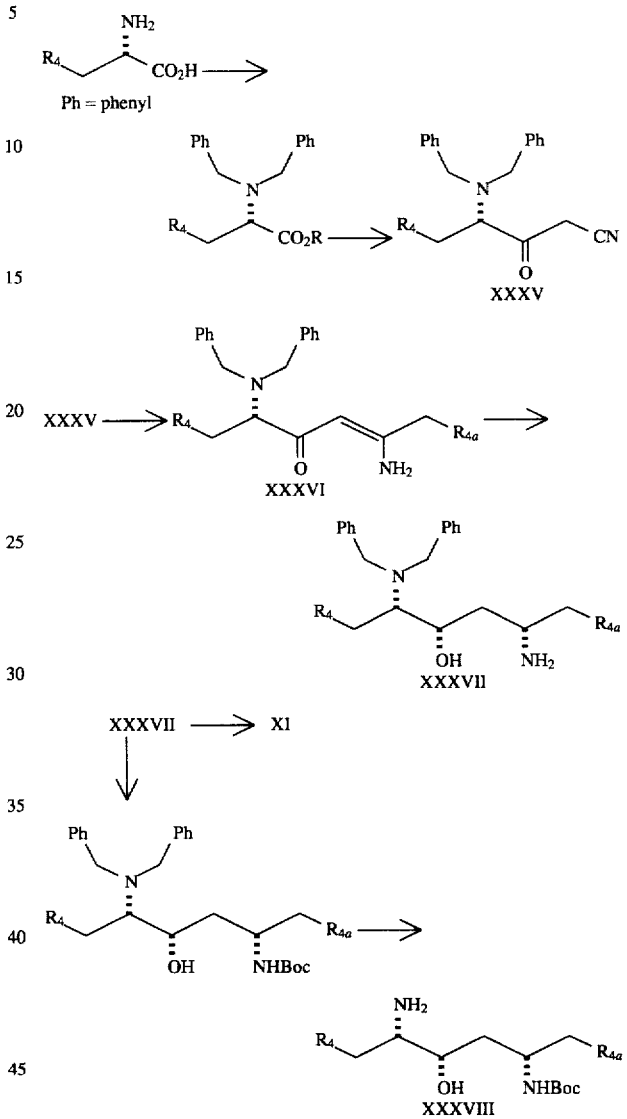

Scheme 8 shows an alternative preparation of XXXVIII. N-protection of XXXVI gives XXXIX. Reaction of XXXIX with borane-tetrahydrofuran complex, followed by reaction of the resulting product with LiAlH₄ or KBH₄, provides the N,N-dibenzyl precursor to XXXVIII.

Scheme 8

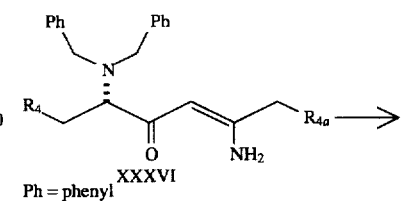

Ph = phenyl   XXXVI

-continued
Scheme 8

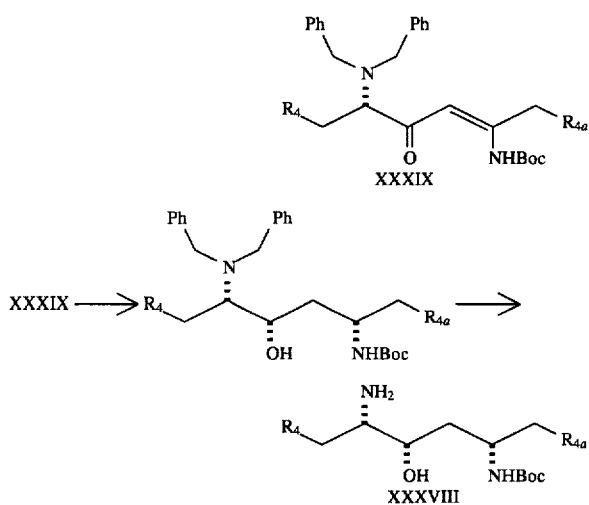

Scheme 9 shows how the selectively protected diamine XXXIX can be used to prepare compounds of the invention XL and XLI.

atmosphere to −60° C. and treated over a period of 15 min with 131 ml of a 2M solution of oxalyl chloride in dichloromethane in order that the internal temperature remained below −50° C. After addition, the solution was stirred at −60° C. for 15 min and treated over a period of 20 min with a solution of 50 g (0.175 mol) of N-(((benzyl)oxy)-carbonyl)-L-phenylalaninol in 200 ml of dichloromethane. The resulting solution was stirred at −60° C. for 1 h, then treated over a period of 15 min with 97 ml of triethylamine in order that the internal temperature remained below −50° C. After addition the solution was stirred at −60° C. for 15 min, then, with the cooling bath in place, was treated rapidly (over a period of 1 min) with a solution of 163 g of citric acid in 550 ml of water. The resulting slurry was stirred vigorously for 10 min, allowed to warm, diluted to 1 liter with water, and separated. The organic layer was washed with 700 ml of water followed by a mixture of 550 ml of water and 150 ml of saturated aqueous $NaHCO_3$, dried over $MgSO_4$, and concentrated in vacuo at 20° C. to give the crude desired compound as a light yellow solid.

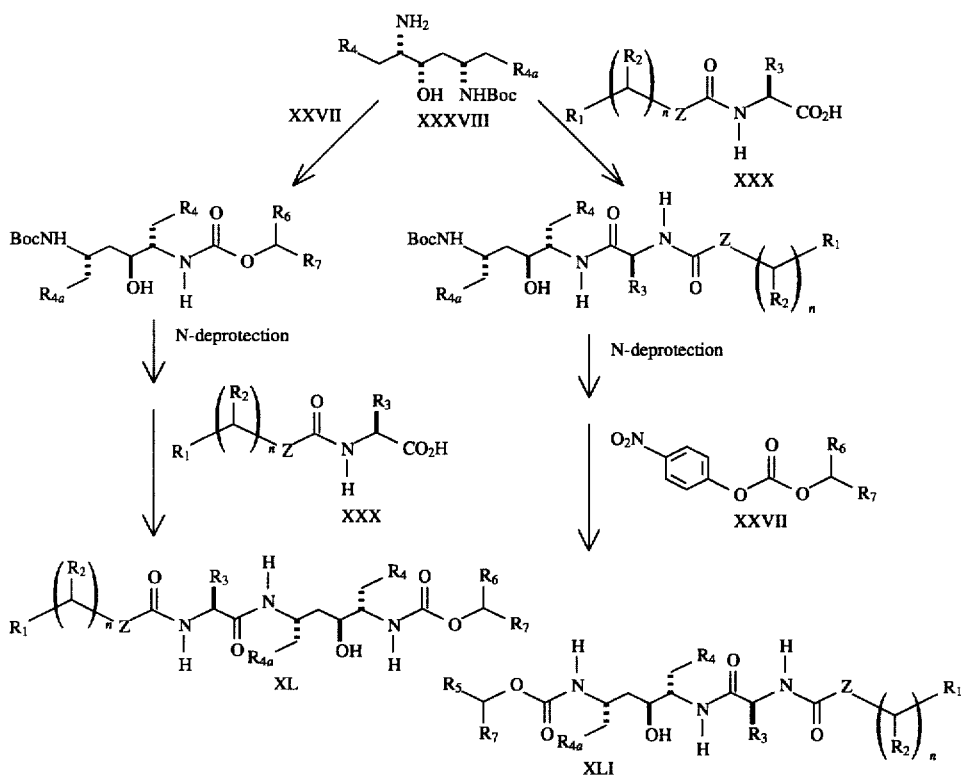

The following examples will serve to further illustrate the preparation of the novel compounds of the invention.

EXAMPLE 1

A. N-(((Benzyl)oxy)carbonyl)-L-phenylalaninal

A solution of 24.5 ml of anhydrous dimethyl sulfoxide in 870 ml of anhydrous dichloromethane was cooled under $N_2$ B. (2S,3R,4R,5S)-2,5-Bis-(N-(((benzyl)oxy)carbonyl)amino)-3,4-dihydroxy-1,6-diphenylhexane and (2S,3S,4S,5S)-2,5-Bis-(N-(((benzyl)oxy)carbonyl)amino)-3,4-dihydroxy-1,6-diphenylhexane A suspension of 78.5 g of $VCl_3$.(tetrahydrofuran)$_3$ and 16 g of zinc dust in 400 ml of dry dichloromethane was stirred under $N_2$ atmosphere for 1 h at 25° C. A solution of 0.175 mol of N-(((benzyl)oxy)carbonyl)-L-phenylalaninal in 200 ml of dichloromethane was then added in one portion, and the resulting mixture was stirred at ambient temperature under $N_2$ atmosphere for 16 h. The resulting mixture was added to 500 ml of 1M aqueous HCl, diluted with 500 ml of hot chloroform, and shaked vigorously for 2 min. The layers were separated, and the organic layer was washed with 1M aqueous HCl and separated. Filtration of the organic phase provided the crude desired product as a solid residue. The residue was slurried in 1.25 liters of acetone, treated with 5 ml of concentrated $H_2SO_4$, and stirred for 16 h at ambient temperature. The resulting mixture was filtered, and the residue (residue A) was washed with 50 ml of acetone. The combined filtrate was concentrated to a volume of 250 ml, diluted with 1000 ml of dichloromethane, washed three times with water and once with saturated brine, dried over $MgSO_4$, and concentrated to give a viscous oil. The oil was taken up in 1000 ml of 1M HCl in methanol (prepared from 71 ml of acetyl chloride and 1000 ml of methanol) and stirred at ambient temperature for 2 h. The resulting precipitate was filtered, washed with methanol, and air-dried on the filter to provide 26.7 g of the desired compound as a white solid. The filtrate was concentrated and filtered to give a second crop (8.3 g) of (2S,3R,4R,5S)-2,5-bis-(N-(((benzyl)oxy)carbonyl)amino)-3,4-dihydroxy-1,6-diphenylhexane. $^1$H NMR ($d_6$-DMSO) δ2.59 (dd, J=13, 5 Hz, 2H), 2.74 (dd, J=13, 9 Hz, 2H), 3.26 (br, 2H), 4.19 (m, 2H), 4.54 (m, 2H), 4.92 (m, 4H), 6.82 (d, J=9 Hz, 2H), 7.0–7.35 (m, 20H). Mass spectrum: $(M+H)^+$=569.

Residue A (above, 2.65 g) was suspended in 75 ml of tetrahydrofuran (THF) and 75 ml of 1M aqueous HCl and heated at reflux for 24 h. After concentration of the resulting solution in vacuo, the residue was taken up in 10% methanol in chloroform, washed two times with water, dried over $Na_2SO_4$, and concentrated in vacuo to provide (2S,3S,4S,5S)-2,5-bis-(N-(((benzyl)oxy)carbonyl)amino) 3,4-dihydroxy-1,6-diphenylhexane as a white solid. $^1$H NMR ($d_6$-DMSO) δ2.64 (m, 2H), 3.04 (m, 2H), 3.49 (m, 2H), 3.78 (m, 2H), 4.70 (d, J=7 Hz, 2H), 4.93 (AA', 4H), 7.1–7.4 (m, 20H). Mass spectrum: $(M+H)^+$=569.

C. (2S,3R,4S,5S)-3-Acetoxy-2,5-bis-(N-(((benzyl)oxy)carbonyl)amino)-3-bromo-1,6-diphenylhexane A suspension of 25 g (44 mmol) of (2S,3R,4R,5S)-2,5-bis-(N-(((benzyl)oxy)carbonyl)amino)-3,4-dihydroxy-1,6-diphenylhexane in 500 ml of 2:1 dichloromethane/hexane was treated with 23 g of α-acetoxyisobutyryl bromide. The resulting mixture was stirred at ambient temperature until the reaction clarified, washed with two 200 ml portions of saturated aqueous $NaHCO_3$, dried over $MgSO_4$, and concentrated in vacuo to give 30.8 g of the crude desired compound. A portion was purified by silica gel chromatography using 9:1 dichloromethane:ethyl acetate to provide the pure desired compound as a white solid. $^1$H NMR (CDCl$_3$) δ2.21 (s, 3H), 2.62 (dd, J=13, 11 Hz, 1H), 2.75 (d, J=7 Hz, 2H), 2.95 (br d, J=15 Hz, 1H), 4.03 (br t, J=10 Hz, 1 h), 4.40 (br d, J=10 Hz, 1H), 4.6–5.0 (m, 6H), 5.12 (br d, J=13 Hz, 1H), 5.33 (br d, J=11 Hz, 1H), 7.0–7.4 (m, 10H). Mass spectrum: $(M+NH_4)^+$=690, 692.

D. (2S,3R,4R,5S)-2,5-Bis-(N-(((benzyl)oxy)carbonyl)amino)-3,4-epoxy-1,6-diphenylhexane A solution of 35.56 g (52.8 mmol) of (2S,3R,4S,5S)-3-acetoxy-2,5-bis-(N-(((benzyl)oxy)carbonyl)amino)-3-bromo-1,6-diphenylhexane in 375 ml of dioxane was treated with 255 ml of 1N aqueous sodium hydroxide and stirred at ambient temperature for 16 h, during which the desired compound precipitated. The resulting mixture was filtered, and the residue was washed with water and dried to provide 22.23 g (76%) of the desired compound as a white solid. $^1$H NMR (CDCl$_3$) δ2.7–2.9 (m, 6H), 3.9–4.0 (m, 2H), 4.6–4.7 (m, 2H), 5.03 (m, 4H), 7.1–7.4 (m, 10H).

E. (2S,3S,5S)-2,5-Bis-(N-(((benzyl)oxy)carbonyl)amino)-1,6-diphenyl-3-hydroxyhexane A mixture of 39.2 g (71.2 mmol) of (2S,3R,4R,5S)-2,5-bis-(N-(((benzyl)oxy)carbonyl)amino)-3,4-epoxy-1,6-diphenylhexane in 600 ml of THF was treated under $N_2$ atmosphere with 13 g (0.36 mol) of sodium borohydride. The resulting mixture was treated dropwise with 27.7 ml (0.36 mol) of trifluoroacetic acid. After being stirred for 3.5 h at ambient temperature, the resulting mixture was quenched with 1N aqueous HCl, diluted with water, and stirred for 16 h. The resulting mixture was filtered, washed with water, and dried to provide 22.85 g (58%) of the desired compound as a white solid.

F. (2S,3S,5S)-2,5-Diamino-1,6-diphenyl-3-hydroxyhexane

A suspension of 32 g of the crude resultant compound of Example 1E and 55.5 g (176 mmol) of barium hydroxide octahydrate in 400 ml of 1,4-dioxane and 400 ml of water was heated at reflux for 4 h. The resulting mixture was filtered, and the residue was rinsed with dioxane. The combined filtrates were concentrated to a volume of approximately 200 ml and extracted with four 400 ml portions of chloroform. The combined organic layers were dried over $Na_2SO_4$, filtered, and concentrated in vacuo. The residue was purified by silica gel chromatography using first 2% isopropylamine in chloroform and then 2% isopropylamine/2% methanol in chloroform to provide 10.1 g (81%) of the pure desired compound as a white solid. $^1$H NMR (CDCl$_3$) δ1.54 (dt, J=14, 10 Hz, 1H), 1.67 (dt, J=14, 3 Hz, 1H), 2.50 (dd, J=13, 8 Hz, 1H), 2.58 (dd, J=13, 8 Hz, 1H), 2.8 (m, 2 H), 2.91 (dd, J=13, 5 Hz, 1H), 3.10 (m, 1H), 3.72 (ddd, J=11,3, 2 Hz, 1H), 7.1–7.4 (m, 10H). Mass spectrum: $(M+H)^+$=285.

G. (4S,6S,1'S)-6-(1-Amino-2-phenylethyl)-4-benzyl-2-phenyl-3-aza-2-bora-1-oxacyclohexane A solution of 131 g (460 mmol) of (2S,3S,5S)-2,5-diamino-1,6-diphenyl-3-hydroxyhexane in 1.2 L of toluene was treated under $N_2$ atmosphere with 56.16 g (460 mmol) of phenylboric acid. The resulting solution was heated at reflux (bath temperature 135° C.) and water azeotropically removed with the aid of a Dean Stark trap until the distillate was clear and the theoretical amount of water (15.6 ml) was collected (ca 1.5 h). After being allowed to cool, the solution was concentrated in vacuo to provide 176 g of the crude desired compound as a resin. H$^1$ NMR (CDCl$_3$) δ7.59 (m, 2H), 7.47–7.07 (m, 13H, 3.92 (m, 1H), 3.78 (s br, 1H), 3.52 (m, 1H), 3.50 (m, 2H), 2.87 (dd, 1H, J=13.5, 5.7 Hz), 2.72 (m, 1H), 2.58 (dd, 1H, J=13.5, 8.7 Hz), 1.92 (m, 1H), 1.68 (m, 1H), 1.60–1.30 (s-very broad, 2H). CIMS m/z 371 (M+H)

H. Thioformamide

To a cooled (0° C.) 2 L three neck round bottom flask equipped with an overhead stirrer charged with a solution of formamide (30.5 mL, 0.76 mol) in 1 L of diethyl ether was added 89 g (0.19 mol) of phosphorous pentasulfide in small portions. The reaction mixture was allowed to warm to ambient temperature, stirred for 2 h, filtered, and concentrated in vacuo to afford thioformamide as a yellow offensive smelling oil which was used without purification.

I. Ethyl 2-Chloro-2-formylacetate

To a three neck 2 L round bottom flask charged with potassium t-butoxide (0.5 mol, 500 mL of a 1M solution in THF) and 500 mL of dry THF cooled to 0° C. was added dropwise from an addition funnel a solution of ethyl chloroacetate (0.5 mol, 53.5 mL) and ethyl formate (0.5 mol, 40.4 mL), in 200 mL of THF over 3 hours. After completion of addition, the reaction mixture was stirred for 1 hour and allowed to stand overnight. The resulting solid was diluted with diethyl ether and cooled in an ice bath. Then, the pH was lowered to approximately 3 using 6N HCl. The organic phase was separated, and the aqueous layer was washed 3 times with diethyl ether. The combined ethereal portions were dried over $NaSO_4$, and concentrated in vacuo. The crude desired compound was stored at −30° C. and used without further purification.

J. Thiazole-5-carboxylate

To a round bottom flask was added 250 mL of dry acetone, 7.5 g (0.123 mol) of thioformamide, and 18.54 g (0.123 mol) of ethyl 2-chloro-2-formylacetate. The reaction was heated at reflux for 2 hours. The solvent was removed in vacuo, and the residue was purified by chromatography ($SiO_2$, 6 cm o.d. column, 100% $CHCl_3$, $R_f$=0.25) to provide 11.6 g (60%) of the desired compound as a light yellow oil. NMR ($CDCl_3$) $\delta1.39$ (t, J=7 Hz, 3H), 4.38 (q, J=7 Hz, 2H), 8.50 (s, 1H), 8.95 (s, 1H).

K. 5-(Hydroxymethyl)thiazole

To a precooled (ice bath) three neck 500 mL flask containing lithium aluminum hydride (76 mmol) in 250 mL of THF was added ethyl thiazole-5-carboxylate (11.82 g, 75.68 mmol) in 100 mL of THF dropwise over 1.5 hours to avoid excess foaming. The reaction was stirred for an additional hour, and treated cautiously with 2.9 mL of water, 2.9 mL of 15% NaOH, and 8.7 mL of water. The solid salts were filtered, and the filtrate set aside. The crude salts were heated at reflux in 100 mL of ethyl acetate for 30 min. The resulting mixture was filtered, and the two filtrates were combined, dried over $Na_2SO_4$, and concentrated in vacuo. The product was purified by silica gel chromatography eluting sequentially with 0%–2%–4% methanol in chloroform, to provide the desired compound, Rf=0.3 (4% methanol in chloroform), which solidified upon standing in 75% yield. NMR ($CDCl_3$), $\delta4.92$ (s, 2H), 7.78 (s, 1H), 8.77 (s, 1H). Mass spectrum: $(M+H)^+$=116.

L. ((5-Thiazolyl)-methyl)-(4-nitrophenyl)carbonate

A solution of 3.11 g (27 mmol) of 5-(hydroxymethyl)thiazole and excess N-methyl morpholine in 100 ml of methylene chloride was cooled to 0° C. and treated with 8.2 g (41 mmol) of 4-nitrophenyl chloroformate. After being stirred for 1 h, the reaction mixture was diluted with $CHCl_3$, washed successively with 1N HCl, saturated aqueous $NaHCO_3$, and saturated brine, dried over $NaSO_4$, and concentrated in vacuo. The residue was purified by silica gel chromatography (SiO2, 1–2% $MeOH/CHCl_3$, Rf=0.5 in 4% $MeOH/CHCl_3$) to yield 5.9 g (78%) of the desired compound as a yellow solid. NMR ($CDCl_3$) $\delta5.53$ (s, 2H), 7.39 (dt, J=9, 3 Hz, 2H), 8.01 (s, 1H), 8.29 (dt, J=9, 3 Hz, 2H), 8.90 (s, 1H). Mass spectrum: $(M+H)^+$=281.

M. (2S,3S,5S)-5-Amino-2-(N-((5-thiazolyl)methoxycarbonyl)amino)-1,6-diphenyl-3-hydroxyhexane and (2S,3S,5S)-2-Amino-5-(N-((5-thiazolyl)methoxycarbonyl)amino)-1,6-diphenyl-3-hydroxyhexane A solution of 500 mg (1.76 mmol) of (2S,3S,5S)-2,5-diamino-1,6-diphenyl-3-hydroxyhexane and 480 mg (1.71 mmol) of ((5-thiazolyl)methyl)(4-nitrophenyl)carbonate in 20 ml of THF was stirred at ambient temperature for 4 h. After removal of the solvent in vacuo, the residue was purified by silica gel chromatography using first 2% then 5% methanol in chloroform to provide a mixture of the two desired compounds. Silica gel chromatography of the mixture using a gradient of 0–1–2% methanol in 93:2 isopropylamine:chloroform provided 110 mg (16%) of (2S,3S,5S)-5-amino-2-(N-((5-thiazolyl)-methoxycarbonyl)amino)-1,6-diphenyl-3-hydroxyhexane ($R_f$ 0.48, 96:2:2 chloroform:methanol:isopropylamine) and 185 mg (28%) of (2S,3S,5S)-2-amino-5-(N-((5-thiazolyl)methoxycarbonyl)amino)-1,6-diphenyl-3-hydroxyhexane ($R_f$ 0.44, 96:2:2 chloroform:methanol:isopropylamine).

(2S,3S,5S)-5-Amino-2-(N-((5-thiazolyl)methoxycarbonyl)amino)-1,6-diphenyl-3-hydroxyhexane: NMR ($CDCl_3$) $\delta1.3–1.6$ (m, 2H), 2.40 (dd, J=14, 8 Hz, 1H), 2.78 (dd, J=5 Hz, 1H), 2.88 (d, J=7 Hz, 2H), 3.01 (m, 1H), 3.72 (br q, 1H), 3.81 (br d, J=10 Hz, 1H), 5.28 (s, 2H), 5.34 (br d, J=9 Hz, 1H), 7.07 (br d, J=7 Hz, 2H), 7.15–7.35 (m, 8H), 7.87 (s, 1H), 8.80 (s, 1H). Mass spectrum: $(M+H)^+$=426.

(2S,3S,5S)-2-Amino-5-(N-((5-thiazolyl)methoxycarbonyl)amino)-1,6-diphenyl-3-hydroxyhexane: NMR ($CDCl_3$) $\delta1.55$ (dt, J=14, 8 Hz, 1H), 1.74 (m, 1H), 2.44 (dd, J=15, 1 Hz, 1H), 2.75–3.0 (m, 4H), 3.44 (m, 1H), 4.00 (br t, 1H), 5.28 (m, 3H), 7.1–7.4 (m, 10H), 7.86 (s, 1H), 8.80 (s, 1H). Mass spectrum: $(M+H)^+$=426.

N. (2S,3S,5S)-5-Amino-2-(N-((5-thiazolyl)methoxycarbonyl)amino)-1,6-diphenyl-3-hydroxyhexane A solution of 40 mmol of crude (4S,6S,1'S)-6-(1-amino-2-phenylethyl)-4-benzyl-2-phenyl-3-aza-2-bora-1-oxacyclohexane in 700 ml of anhydrous THF was cooled to −40° C. and treated dropwise over a period of 1 h with a solution of 7.83 g (27.9 mmol) of ((5-thiazolyl)methyl)-(4-nitrophenyl)carbonate in 300 ml of dry THF. The resulting solution was allowed to warm to 0° C. for 3 h, then to ambient temperature for 16 h. The solvent was removed in vacuo, and the residue was taken up in 700 ml of ethyl acetate, washed with three 150 ml portions of 1N aqueous NaOH and one 150 ml portion of brine. The organic phase was dried over $Na_2SO_4$ and concentrated in vacuo. Purification of the residue by silica gel chromatography using methanol/chloroform mixtures provided the desired compound mixed with its regioisomer. A second chromatography using 1–3% isopropylamine in chloroform provided 5.21 g of the desired compound which solidified upon standing.

O. 2-Methylpropane-thioamide

A suspension of 100 g (1.15 mol) of isobutyramide in 4 L of diethyl ether was stirred vigorously and treated in portions with 51 g (0.115 mol) of $P_4S_{10}$. The resulting mixture was stirred at ambient temperature for 2 h, filtered, and concentrated in vacuo to provide 94.2 g (80%) of the crude desired compound. $^1H$ NMR (DMSO-$d_6$) $\delta1.08$ (d, J=7 Hz, 6H), 2.78 (heptet, J=7 Hz, 1H), 9.06 (br, 1H), 9.30 (br, 1H). Mass spectrum: (M+H)⁺=104.

P. 4-(Chloromethyl)-2-isopropylthiazole hydrochloride

A mixture of 94.0 g (0.91 mol) of 2-methylpropanethioamide, 115.7 g (0.91 mol) of 1,3-dichloroacetone, and 109.7 g (0.91 mol) of MgSO₄ in 1.6 liters of acetone was heated at reflux for 3.5 h. The resulting mixture was allowed to cool, filtered, and the solvent was removed in vacuo to provide the crude desired compound as a yellow oil. ¹H NMR (DMSO-d6) δ1.32 (d, J=7 Hz, 6H), 3.27 (heptet, J=7 Hz, 1H), 4.78 (s, 2H), 7.61 (s, 1H). Mass spectrum: (M+H)⁺=176.

Q. 2-Isopropyl-4-(((N-methyl)amino)methyl)thiazole

A solution of 40 g of 4-(chloromethyl)-2-isopropylthiazole hydrochloride in 100 ml of water was added dropwise with stirring to 400 ml of 40% aqueous methylamine. The resulting solution was stirred for 1 h, then concentrated in vacuo. The residue was taken up in chloroform, dried over Na₂SO₄, and concentrated in vacuo. Purification of the residue by silica gel chromatography using 10% methanol in chloroform provided 21.35 g (55%) of the desired compound. ¹H NMR (DMSO-d₆) δ1.34 (d, J=7 Hz, 6H), 2.56 (s, 3H), 3.30 (heptet, J=7 Hz, 1H), 4.16 (s, 2H), 7.63 (s, 1H). Mass spectrum: (M+H)⁺=171.

R. N-(((4-Nitrophenyl)oxy)carbonyl)-L-valine Methyl Ester

A solution of 66.1 g (0.328 mol) of 4-nitrophenyl chloroformate in 1.2 liters of CH₂Cl₂ was cooled to 0° C. and treated with L-valine methyl ester hydrochloride. The resulting mixture was treated slowly, with stirring, with 68.9 ml (0.626 mol) of 4-methylmorpholine. The resulting solution was allowed to slowly warm to ambient temperature and was stirred overnight. After washing with 3 portions of 10% aqueous NaHCO₃, the solution was dried over Na₂SO₄ and concentrated in vacuo. The residue was purified by silica gel chromatography by eluting with chloroform to provide the desired compound. ¹H NMR (DMSO-d₆) δ0.94 (d, J=7 Hz, 3H), 0.95 (d, J=7 Hz, 3H), 2.12 (octet, J=7 Hz, 1H), 3.69 (s, 3H), 4.01 (dd, J=8, 6 Hz, 1H), 7.41 (dt, J=9, 3 Hz, 2H), 8.27 (dt, J=9, 3 Hz, 2H), 8.53 (d, J=8 Hz, 1H). Mass spectrum: (M+NH₄)⁺=314.

S. N-((N-Methyl-N-((2-isopropyl-4-thiazolyl)methyl)amino)carbonyl)-L-valine Methyl Ester A solution of 15.7 g (92 mmol) of 2-isopropyl-4-(((N-methyl)amino)methyl)thiazole in 200 ml of THF was combined with a solution of 20.5 g (69 mmol) of N-(((4-nitrophenyl)oxy)carbonyl)-L-valine methyl ester. The resulting solution was treated with 1.6 g of 4-dimethylaminopyridine and 12.9 ml (92 mmol) of triethylamine, heated at reflux for 2 h, allowed to cool, and concentrated in vacuo. The residue was taken up in CH₂Cl₂, washed extensively with 5% aqueous K₂CO₃, dried over Na₂SO₄, and concentrated in vacuo. The resulting product mixture was purified by silica gel chromatography using chloroform as an eluent to provide 16.3 g (54%) of the desired compound. ¹H NMR (DMSO-d₆) δ0.88 (d, J=7 Hz, 3H), 0.92 (d, J=7 Hz, 3H), 1.32 (d, J=7 Hz, 3H), 2.05 (octet, J=7 Hz, 1H), 2.86 (s, 3H), 3.25 (heptet, J=7 Hz, 1H), 3.61 (s, 3H), 3.96 (dd, J=8, 7 Hz, 1H), 4.44 (AA', 2H), 6.58 (d, J=8 Hz, 1H), 7.24 (s, 1H). Mass spectrum: (M+H)⁺=328.

T. N-((N-Methyl-N-((2-isopropyl-4-thiazolyl)methyl)amino)carbonyl)-L-valine

A solution of 1.42 g (4.3 mmol) of the resultant compound of Example 1S in 17 ml of dioxane was treated with 17.3 ml of 0.50M aqueous LiOH. The resulting solution was stirred at ambient temperature for 30 min, treated with 8.7 ml of 1M HCl, and concentrated in vacuo. The residue was taken up in dichloromethane, washed with water, dried over Na₂SO₄, and concentrated in vacuo to provide 1.1 g (81%) of the desired compound. Mass spectrum: (M+H)⁺=314.

U. (2S,3S,5S)-5-(N-(N-((N-Methyl-N-((2-isopropyl-4-thiazolyl)methyl)amino)carbonyl)valinyl)amino)-2-(N-((5-thiazolyl)methoxycarbonyl)amino)-1,6-diphenyl-3-hydroxyhexane A solution of 70 mg (0.223 mmol) of N-((N-methyl-N-((2-isopropyl-4-thiazolyl)methyl)amino)carbonyl)-L-valine, 79 mg (0.186 mmol) of (2S,3S,5S)-5-amino-2-(N-((5-thiazolyl)methoxycarbonyl)amino)-1,6-diphenyl-3-hydroxyhexane, 30 mg (0.223 mmol) of 1-hydroxybenzotriazole hydrate, and 51 mg (0.266 mmol) of N-ethyl-N'-dimethylaminopropyl carbodiimide in 2 ml of THF was stirred at ambient temperature for 16 h. The resulting solution was concentrated in vacuo, and the residue was purified by silica gel chromatography using 97:3 CH₂Cl₂:CH₃OH to provide 100 mg (74%) of the desired compound (R_f 0.4, 95:5 CH₂Cl₂:CH₃OH) as a solid. ¹H NMR (d₆-DMSO) δ0.73 (d, J=7 Hz, 6H), 1.30 (d, J=7 Hz, 6H), 1.45 (m, 2H), 1.87 (m, 1H), 2.5–2.7 (m, 4H), 2.87 (s, 3H), 3.23 (heptet, J=7 Hz, 1H), 3.57 (m, 1H), 3.81 (m, 1H), 3.93 (m, 1H), 4.15 (m, 1H), 4.44 (AA', 2H), 4.62 (d, J=6 Hz, 1H), 5.13 (AA', 2H), 6.01 (d, J=9 Hz, 1H), 6.89 (d, J=9 Hz, 1H), 7.1–7.2 (m, 11H), 7.68 (d, J=9 Hz, 1H), 7.85 (s, 1H), 9.05 (s, 1H). Mass spectrum: (M+H)⁺=721. Anal. Calcd for C₃₇H₄₈N₆O₅S₂.0.5H₂O: C, 60.88; H, 6.77; N, 11.51. Found: C, 60.68; H, 6.53; N, 11.36.

EXAMPLE 2

Following the procedures of Example 1, the following compounds can be prepared:

(2S,3S,5S)-5-(N-(N-((N-Methyl-N-((2-cyclohexyl-4-thiazolyl)methyl)amino)carbonyl)valinyl)amino)-2-(N-((5-thiazolyl)methoxycarbonyl)amino)-1,6-diphenyl-3-hydroxyhexane.

(2S,3S,5S)-5-(N-(N-((N-Methyl-N-((2-(1,1-dimethyl)ethyl-4-thiazolyl)methyl)amino)carbonyl)valinyl)amino)-2-(N-((5-thiazolyl)methoxycarbonyl)amino)-1,6-diphenyl-3-hydroxyhexane.

(2S,3S,5S)-5-(N-(N-((N-Methyl-N-((2-ethenyl-4-thiazolyl)methyl)amino)carbonyl)valinyl)amino)-2-(N-((5-thiazolyl)methoxycarbonyl)amino)-1,6-diphenyl-3-hydroxyhexane.

(2S,3S,5S)-5-(N-(N-((N-Methyl-N-((2-(2-propenyl)-4-thiazolyl)methyl)amino)-carbonyl)valinyl)amino)-2-(N-((5thiazolyl)methoxycarbonyl)amino)-1,6-diphenyl-3-hydroxyhexane.

(2S,3S,5S)-5-(N-(N-((N-Methyl-N-((2-(1-cyclopentenyl)-4-thiazolyl)methyl)amino)carbonyl)valinyl)amino)-2-(N-((5-thiazolyl)methoxycarbonyl)amino)-1,6-diphenyl-3-hydroxyhexane.

(2S,3S,5S)-5-(N-(N-((N-Methyl-N-((2-(1-cyclohexenyl)-4-thiazolyl)methyl)amino)carbonyl)valinyl)amino)-2-(N-((5-thiazolyl)methoxycarbonyl)amino)-1,6-diphenyl-3-hydroxyhexane.

(2S,3S,5S)-5-(N-(N-((N-Methyl-N-((4-cyclopentenyl-4-thiazolyl)methyl)amino)-carbonyl)valinyl)amino)-2-(N-((5-thiazolyl)methoxycarbonyl)amino)-1,6-diphenyl-3-hydroxyhexane.

(2S,3S,5S)-5-(N-(N-((N-Methyl-N-((4-cyclohexenyl-4-thiazolyl)methyl)amino)-carbonyl)valinyl)amino)-2-(N-((5-thiazolyl)methoxycarbonyl)amino)-1,6-diphenyl-3-hydroxyhexane.

(2S,3S,5S)-5-(N-(N-((N-Methyl-N-((2-(3-propenyl)-4-thiazolyl)methyl)amino)-carbonyl)valinyl)amino)-2-(N-((5-thiazolyl)methoxycarbonyl)amino)-1,6-diphenyl-3-hydroxyhexane.

(2S,3S,5S)-5-(N-(N-((N-Methyl-N-((2-(1-propenyl)-4-thiazolyl)methyl)amino)-carbonyl)valinyl)amino)-2-(N-((5-thiazolyl)methoxycarbonyl)amino)-1,6-diphenyl-3-hydroxyhexane.

(2S,3S,5S)-5-(N-(N-((N-Methyl-N-((2-(1-methyl-1-propenyl)-4-thiazolyl)methyl)-amino)carbonyl)valinyl)amino)-2-(N-((5-thiazolyl)methoxycarbonyl)amino)-1,6-diphenyl-3-hydroxyhexane.

(2S,3S,5S)-5-(N-(N-((N-Methyl-N-((2-(2-methyl-1-propenyl)-4-thiazolyl)methyl)amino)carbonyl)valinyl)amino)-2-(N-((5-thiazolyl)methoxycarbonyl)amino)-1,6-diphenyl-3-hydroxyhexane.

(2S,3S,5S)-5-(N-(N-((N-Methyl-N-((2-(1,2-dimethyl-1-propenyl)-4-thiazolyl)methyl)amino)carbonyl)valinyl)amino)-2-(N-((5-thiazolyl)methoxycarbonyl)amino)-1,6-diphenyl-3-hydroxyhexane.

(2S,3S,5S)-5-(N-(N-((N-Methyl-N-((2-(cyclopentyl)methyl-4-thiazolyl)methyl)-amino)carbonyl)valinyl)amino)-2-(N-((5-thiazolyl)methoxycarbonyl)amino)-1,6-diphenyl-3-hydroxyhexane.

(2S,3S,5S)-5-(N-(N-((N-Methyl-N-((2-(cyclohexyl)methyl-4-thiazolyl)methyl)amino)carbonyl)valinyl)amino)-2-(N-((5-thiazolyl)methoxycarbonyl)amino)-1,6-diphenyl-3-hydroxyhexane.

(2S,3S,5S)-5-(N-(N-((N-Methyl-N-((2-phenyl-4-thiazolyl)methyl)amino)carbonyl)valinyl)amino)-2-(N-((5-thiazolyl)methoxycarbonyl)amino)-1,6-diphenyl-3-hydroxyhexane.

(2S,3S,5S)-5-(N-(N-((N-Methyl-N-((2-benzyl-4-thiazolyl)methyl)amino)carbonyl)valinyl)amino)-2-(N-((5-thiazolyl)methoxycarbonyl)amino)-1,6-diphenyl-3-hydroxyhexane.

(2S,3S,5S)-5-(N-(N-((N-Methyl-N-((2-(2-phenyl)ethyl-4-thiazolyl)methyl)amino)-carbonyl)valinyl)amino)-2-(N-((5-thiazolyl)methoxycarbonyl)amino)-1,6-diphenyl-3-hydroxyhexane.

(2S,3S,5S)-5-(N-(N-((N-Methyl-N-((2-(2-phenyl-1-ethenyl)-4-thiazolyl)methyl)amino)carbonyl)valinyl)amino)-2-(N-((5-thiazolyl)methoxycarbonyl)amino)-1,6-diphenyl-3-hydroxyhexane.

(2S,3S,5S)-5-(N-(N-((N-Methyl-N-((2-(4-fluoro)phenyl-4-thiazolyl)methyl)amino)carbonyl)valinyl)amino)-2-(N-((5-thiazolyl)methoxycarbonyl)amino)-1,6-diphenyl-3-hydroxyhexane.

(2S,3S,5S)-5-(N-(N-((N-Methyl-N-((2-(2-chloro)phenyl-4-thiazolyl)methyl)amino)carbonyl)valinyl)amino)-2-(N-((5-thiazolyl)methoxycarbonyl)amino)-1,6-diphenyl-3-hydroxyhexane.

(2S,3S,5S)-5-(N-(N-((N-Methyl-N-((2-(3-methoxy)phenyl-4-thiazolyl)methyl)amino)carbonyl)valinyl)amino)-2-(N-((5-thiazolyl)methoxycarbonyl)amino)-1,6-diphenyl-3-hydroxyhexane.

(2S,3S,5S)-5-(N-(N-((N-Methyl-N-((2-(2-thiazolyl)-4-thiazolyl)methyl)amino)carbonyl)valinyl)amino)-2-(N-((5-thiazolyl)methoxycarbonyl)amino)-1,6-diphenyl-3-hydroxyhexane. p0 (2S,3S,5S)-5-(N-(N-((N-Methyl-N-((2-(2-thiazolyl)methyl-4-thiazolyl)methyl)amino)carbonyl)valinyl)amino)-2-(N-((5-thiazolyl)methoxycarbonyl)amino)-1,6-diphenyl-3-hydroxyhexane.

(2S,3S,5S)-5-(N-(N-((N-Methyl-N-((2-methoxy-4-thiazolyl)methyl)amino)carbonyl)valinyl)amino)-2-(N-((5-thiazolyl)methoxycarbonyl)amino)-1,6-diphenyl-3-hydroxyhexane.

(2S,3S,5S)-5-(N-(N-((N-Methyl-N-((2-ethoxy-4-thiazolyl)methyl)amino)carbonyl)valinyl)amino)-2-(N-((5-thiazolyl)methoxycarbonyl)amino)-1,6-diphenyl-3-hydroxyhexane.

(2S,3S,5S)-5-(N-(N-((N-Methyl-N-((2-isopropyloxy-4-thiazolyl)methyl)amino)-carbonyl)valinyl)amino)-2-(N-((5-thiazolyl)methoxycarbonyl)amino)-1,6-diphenyl-3-hydroxyhexane.

(2S,3S,5S)-5-(N-(N-((N-Methyl-N-((2-(N,N-dimethylamino)methyl-4-thiazolyl)-methyl)amino)carbonyl)valinyl)amino)-2-(N-((5-thiazolyl)methoxycarbonyl)-amino)-1,6-diphenyl-3-hydroxyhexane.

(2S,3S,5S)-5-(N-(N-((N-Methyl-N-((2-(1-pyrrolidinyl)methyl-4-thiazolyl)methyl)-amino)carbonyl)valinyl)amino)-2-(N-((5-thiazolyl)methoxycarbonyl)amino)-1,6-diphenyl-3-hydroxyhexane.

(2S,3S,5S)-5-(N-(N-((N-Methyl-N-((2-propyl-4-thiazolyl)methyl)amino)carbonyl)valinyl)amino)-2-(N-((5-thiazolyl)methoxycarbonyl)amino)-1,6-diphenyl-3-hydroxyhexane.

(2S,3S,5S)-5-(N-(N-((N-Methyl-N-((2-(2-methyl)propyl-4-thiazolyl)methyl)amino)carbonyl)valinyl)amino)-2-(N-((5-thiazolyl)methoxycarbonyl)amino)-1,6-diphenyl-3-hydroxyhexane.

(2S,3S,5S)-5-(N-(N-((N-Methyl-N-((2-(1-methyl)propyl-4-thiazolyl)methyl)amino)carbonyl)valinyl)amino)-2-(N-((5-thiazolyl)methoxycarbonyl)amino)-1,6-diphenyl-3-hydroxyhexane.

(2S,3S,5S)-5-(N-(N-((N-Methyl-N-((2-(1-ethyl)propyl-4-thiazolyl)methyl)amino)-carbonyl)valinyl)amino)-2-(N-((5thiazolyl)methoxycarbonyl)amino)-1,6-diphenyl-3-hydroxyhexane.

EXAMPLE 3

A. N-(((4-nitrophenyl)oxy)carbonyl)-L-alanine Methyl Ester

Using the procedure of Example 1R, but replacing L-valine methyl ester hydrochloride with L-alanine methyl ester hydrochloride provided the desired compound ($R_f$ 0.25, dichloromethane) in 95% yield.

B. N-((N-Methyl-N-((2-isopropyl-4-thiazolyl)methyl)amino)carbonyl)-L-alanine Methyl Ester Using the procedure of Example 1S, but replacing N-(((4-nitrophenyl)oxy)carbonyl)-L-valine methyl ester with the resultant compound of Example 3A provided, after silica gel chromatography using 97:3 $CH_2Cl_2$:$CH_3OH$, the desired compound ($R_f$ 0.55, 95:5 $CH_2Cl_2$:$CH_3OH$) in 24% yield. $^1$H NMR ($CDCl_3$) δ1.39 (d, J=7 Hz, 6H), 1.43 (d, J=7 Hz, 3H), 2.98 (s, 3H), 3.28 (heptet, J=7 Hz, 1H), 3.74 (s, 3H), 4.46 (s, 2H), 4.49 (q, J=7 Hz, 1H), 6.12 (br, 1H), 6.98 (s, 1H). Mass spectrum: $(M+H)^+$=300.

C. N-((N-Methyl-N-((2-isopropyl-4-thiazolyl)methyl)amino)carbonyl)-L-alanine Using the procedure of Example 1T, but replacing the resultant compound of Example 1S with the resultant compound of Example 3B provided the desired compound.

D. (2S,3S,5S)-5(N-(N-((N-Methyl-N-((2-isopropyl-4-thiazolyl)methyl)amino)carbonyl)alaninyl)amino-2-(N-((5-thiazolyl)methoxycarbonyl)amino)-1,6-diphenyl-3-hydroxyhexane Using the procedure of Example 1U but replacing N-((N-methyl-N-((2-isopropyl-4-thiazolyl)methyl)amino)carbonyl)-L-valine with the resultant compound of Example 3C provided, after silica gel chromatography using 97:3 $CH_2Cl_2$:$CH_3OH$, 70 mg (35%) of the desired compound ($R_f$ 0.36, 95:5 $CH_2Cl_2$:$CH_3OH$), mp. 56°–58° C. Mass spectrum: $(M+H)^+=693$. Anal. Calcd for $C_{35}H_{44}N_6O_5S_2 \cdot 0.5H_2O$: C, 59.89; H, 6.46; N, 11.97. Found: C, 60.07; H, 6.39; N, 12.00.

EXAMPLE 4

A. 2-Isopropyl-4-(((N-ethyl)amino)methyl)thiazole

Using the procedure of Example 1Q, but replacing 40% aqueous methylamine with 70% aqueous ethylamine provided the crude desired compound. $^1H$ NMR (DMSO-$d_6$) δ1.12 (t, J=7 Hz, 3H), 1.32 (d, J=7 Hz, 6H), 2.78 (q, J=7 Hz, 2H), 3.27 (q, J=7 Hz, 1H), 3.97 (s, 2H), 7.44 (s, 1H).

B. N-((N-Ethyl-N-((2-isopropyl-4-thiazolyl)methyl)amino)carbonyl)-L-valine Methyl Ester Using the procedure of Example 1S, but replacing 2-isopropyl-4-(((N-methyl)amino)methyl)thiazole with 2-isopropyl-4-(((N-ethyl)amino)methyl)-thiazole provided, after silica gel chromatography using 98:2 $CHCl_3$:$CH_3OH$, the desired compound ($R_f$ 0.5, 95:3 $CH_2Cl_2$:$CH_3OH$) in 54% yield. $^1H$ NMR (CDCl$_3$) δ0.94 (d, J=7 Hz, 3H), 0.98 (d, J=7 Hz, 3H), 1.16 (t, J=7 Hz, 3H), 1.39 (d, J=7 Hz, 6H), 2.16 (m, 1H), 3.25–3.50 (m, 3H), 3.71 (s, 3H), 4.38 (dd, J=8, 6 Hz, 1H), 4.46 (AA', 2H), 6.13 (br, 1H), 7.00 (s, 1H). Mass spectrum: $(M+H)^+=342$.

C. N-((N-Ethyl-N-((2-isopropyl-4-thiazolyl)methyl)amino)carbonyl)-L-valine

Using the procedure of Example 1T, but replacing the resultant compound of Example 1S with the resultant compound of Example 4B provided the desired compound.

D. (2S,3S,5S)-5-(N-(N-((N-Ethyl-N-((2-isopropyl-4-thiazolyl)methyl)amino)carbonyl)valinyl)amino)-2-(N-((5-thiazolyl)methoxy)carbonyl)amino)-1,6-diphenyl-3-hydroxyhexane Using the procedure of Example 1U but replacing N-((N-methyl-N-((2-isopropyl-4-thiazolyl)methyl)amino)carbonyl)-L-valine with the resultant compound of Example 4C provided, after silica gel chromatography using 98:2 $CHCl_3$:$CH_3OH$, 60 mg (35%) of the desired compound ($R_f$ 0.4, 95:5 $CH_2Cl_2$:$CH_3OH$), mp. 58°–60° C. Mass spectrum: $(M+H)^+=735$.

EXAMPLE 5

A. Ethyl 2-Isopropylthiazole-4-carboxylate

A solution of 2.35 g (23 mmol) of 2-methylpropanethioamide and 2.89 ml (23 mmol) of ethyl bromopyruvate in 75 ml of acetone was treated with excess $MgSO_4$ and heated at reflux for 2.5 h. The resulting mixture was allowed to cool, filtered, and concentrated in vacuo to an oil, which was taken up in chloroform, washed sequentially with aqueous $NaHCO_3$ and brine, dried over $Na_2SO_4$, and concentrated. The residue was purified by chromatography on silica gel using chloroform as an eluent to provide 3.96 g (86%) of the desired compound, $R_f$ 0.21 (chloroform) as an oil. $^1H$ NMR (CDCl$_3$) δ1.41 (t, J=8 Hz, 3H), 1.42 (d, J=7 Hz, 6H), 3.43 (heptet, J=7 Hz, 1H), 4.41 (q, J=8 Hz, 2H), 8.05 (s, 1H). Mass spectrum: $(M+H)^+=200$.

B. 4-(Hydroxymethyl)-2-isopropylthiazole

A solution of 10 ml (10 mmol) of lithium aluminum hydride in toluene was diluted in a dry flask under $N_2$ atmosphere with 75 ml of THF. The resulting mixture was cooled to 0° C. and treated dropwise with a solution of 3.96 g (20 mmol) of ethyl 2-isopropyl-4-thiazolecarboxylate in 10 ml of THF. After addition, the solution was stirred at 0° C. for 3 h, diluted with ether, and treated with a small amount of aqueous Rochelle's salt. After stirring, the slurry was filtered, washed with ethyl acetate, and the combined filtrates were concentrated in vacuo. The residue was purified by silica gel chromatography using 2% methanol in chloroform to provide 2.18 g (69%) of the desired compound, $R_f$ 0.58 (4% methanol in chloroform). $^1H$ NMR (CDCl$_3$) δ1.39 (d, J=7 Hz, 6H), 2.94 (br, 1H), 3.31 (heptet, J=7 Hz, 1H), 4.74 (s, 2H), 7.04 (s, 1H). Mass spectrum: $(M+H)^+=158$.

C. α-Isocyanato-valine Methyl Ester

A suspension of L-valine methyl ester hydrochloride (49 g, 0.29 mol) in toluene (700 ml) was heated to 100° C. and phosgene gas was bubbled into the reaction mixture. After approximately 6 h, the mixture became homogeneous. The bubbling of phosgene was continued for 10 more min, then the solution was cooled with the bubbling of $N_2$ gas. The solvent was then evaporated and the residue chased with toluene two times. Evaporation of solvent gave 40.8 g (89%) of the crude desired compound.

D. N-((2-Isopropyl-4-thiazolyl)methoxycarbonyl)valine Methyl Ester

A solution of 2.18 g (15 mmol) of 4-(hydroxymethyl)-2-isopropylthiazole, 15.8 mmol of α-isocyanato-valine methyl ester and 1.5 mmol of 4-dimethylaminopyridine in 75 ml of dichloromethane was heated at reflux for 5 h. The resulting solution was washed successively with 10% citric acid, aqueous $NaHCO_3$ and brine, dried over $Na_2SO_4$, and concentrated in vacuo. Silica gel chromatography of the residue using 5% ethyl acetate in chloroform provided 2.67 g (57%) of the pure desired compound, $R_f$ 0.46 (4% methanol in chloroform). NMR $^1H$ NMR (DMSO-$d_6$) δ1.26 (d, J=8 Hz, 3H), 1.32 (d, J=7 Hz, 6H), 3.27 (heptet, J=7 Hz, 1H), 3.63 (s, 3H), 4.10 (pentet, J=8 Hz, 1H), 5.02 (s, 2H), 7.47 (s, 1H), 7.81 (d, J=8 Hz, 1H). Mass spectrum: $(M+H)^+=287$.

E. N-((2-Isopropyl-4-thiazolyl)methoxycarbonyl)valine

Using the procedure of Example 1T, but replacing the resultant compound of Example 1S with the resultant compound of Example 5D provided the desired compound.

F. (2S,3S,5S)-5-(N-(N-((2-Isopropyl-4-thiazolyl)methoxycarbonyl)valinyl)amino)-2-(N-((5-thiazolyl)methoxycarbonyl)amino)-1,6-diphenyl-3-hydroxyhexane Using the procedure of Example 1U but replacing N-((N-methyl-N-((2-isopropyl-4-thiazolyl)methyl)amino)carbonyl)-L-valine with the resultant compound of Example 5E provided, after silica gel chromatography using 2% methanol in chloroform, 110 mg (58%) of the desired compound ($R_f$ 0.44, 10% methanol in chloroform), mp. 142°–145° C. Mass spectrum: $(M+H)^+=708$.

EXAMPLE 6

(2S,3S,5S)-2-(N-(N-((2-Isopropyl-4-thiazolyl)methoxycarbonyl)valinyl)amino)-5-(N-((5-thiazolyl)methoxycarbonyl)amino)-1,6-diphenyl-3-hydroxyhexane Using the procedure of Example 1U but replacing N-((N-methyl-N-((2-isopropyl-4-thiazolyl)methyl)amino)carbonyl)-L-valine with the resultant compound of Example 5E and replacing (2S,3S,5S)-5-amino-2-(N-((5-thiazolyl)methoxycarbonyl)amino)-1,6-diphenyl-3-hydroxyhexane with (2S,3S,5S)-2-amino-5-(N-((5-thiazolyl)methoxycarbonyl)amino)-1,6-diphenyl-3-hydroxyhexane provided, after silica gel chromatography using 2% methanol in chloroform, 105 mg (55%) of the desired compound ($R_f$ 0.33, 10% methanol in chloroform), mp. 172°–174° C. Mass spectrum: $(M+H)^+=708$.

EXAMPLE 7

A. N-((2-Isopropyl-4-thiazolyl)methoxycarbonyl)alanine Methyl Ester

A solution of 1.12 g (5.56 mmol) of 4-nitrophenyl chloroformate in 20 ml of $CH_2Cl_2$ was cooled to 0° C. and treated sequentially with 0.8 g (5.1 mmol) of 4-(hydroxymethyl)-2-isopropylthiazole and 0.6 ml (5.6 mmol) of 4-methylmorpholine. The resulting solution was stirred at 0° C. for 1 h, diluted with $CH_2Cl_2$, washed with three portions of aqueous $NaHCO_3$, dried over $Na_2SO_4$, and concentrated in vacuo to give crude 2-isopropyl-4-(p-nitrophenyloxycarbonyloxymethyl)thiazole. A portion (0.53 g, 1.65 mmol) of the residue was taken up in 20 ml of chloroform, treated with 0.23 g (1.67 mmol) of L-alanine methyl ester hydrochloride and 0.36 ml (3.3 mmol) of 4-methylmorpholine, and heated at reflux for 16 h. After being allowed to cool, the solvent was removed in vacuo, and the residue was purified by silica gel chromatography using 2% methanol in chloroform to provide 0.45 g (94%) of the desired compound, $R_f$ 0.43 (5% methanol in $CH_2Cl_2$). $^1$H NMR (DMSO-$d_6$) δ1.26 (d, J=8 Hz, 3H), 1.32 (d, J=7 Hz, 6H), 3.27 (heptet, J=7 Hz, 1H), 3.63 (s, 3H), 4.10 (p, J=8 Hz, 1H), 5.02 (s, 2H), 7.47 (s, 1H), 7.81 (d, J=8 Hz, 1H). Mass spectrum: $(M+H)^+=287$.

B. N-((2-Isopropyl-4-thiazolyl)methoxycarbonyl)alanine

Using the procedure of Example 1T, but replacing the resultant compound of Example 1S with the resultant compound of Example 7A provided the desired compound.

C. (2S,3S,5S)-5-(N-(N-((2-Isopropyl-4-thiazolyl)methoxycarbonyl)alaninyl)amino)-2-(N-((5-thiazolyl)methoxycarbonyl)amino)-1,6-diphenyl-3-hydroxyhexane Using the procedure of Example 1U but replacing N-((N-methyl-N-((2-isopropyl-4-thiazolyl)methyl)amino)carbonyl)-L-valine with the resultant compound of Example 7B provided, after silica gel chromatography using 1% methanol in chloroform, 110 mg (69%) of the desired compound ($R_f$ 0.4, 5% methanol in $CH_2Cl_2$), mp. 59°–61° C. Mass spectrum: $(M+H)^+=680$. Anal. Calcd for $C_{34}H_{41}N_5O_6S_2 \cdot 0.5H_2O$: C, 59.28; H, 6.15; N, 10.17. Found: C, 59.37; H, 5.96; N, 10.18.

EXAMPLE 8

A. (5S,1'S)-5-(1-(tert-Butyloxycarbonylamino)-2-phenylethyl)-dihydrofuran-2(3H)-one Prepared from commercially available ethyl-3-bromopropionate by using the procedure of A. E. DeCamp, et al., (*Tetrahedron Lett.* 1991, 32, 1867).

B. (5S,1'S)-5-(1-(tert-Butyloxycarbonylamino)-2-phenylethyl)-3-carboethoxy-dihydrofuran-2(3H)-one Lithium diisopropylamide (LDA) was prepared by dropwise addition of 16.5 ml (41.2 mmol) of 2.5M n-BuLi to a solution of 5.8 ml (41.2 mmol) of diisopropyl amine in 30 ml of dry tetrahydrofuran at −78° C. The LDA solution was stirred for 30 min at −78° C. and 6.0 g (19.6 mmol) of the resultant compound of Example 8A in 30 ml of dry tetrahydrofuran was added dropwise. The reaction mixture was stirred for 30 min at −78° C. and 4.7 ml (49.1 mmol) of ethyl chloroformate was then added. After being stirred at −78° C. for 5 h, the reaction was quenched with saturated aqueous $NH_4Cl$, extracted with three 60 ml portions of dichloromethane. The combined organic layers were dried over $Na_2SO_4$, concentrated in vacuo and the residue was purified by silica gel chromatography using 25% ethyl acetate in hexane to provide 4.73 g (64%) of the desired compound as a white solid. Mass spectrum: $(M+H)^+=378$.

C. (5S,1'S)-5-(1-(tert-Butyloxycarbonylamino)-2-phenylethyl)-3-carboethoxy-3-((5-thiazolyl)methyl)dihydrofuran-2(3H)-one Sodium metal (536 mg, 23.3 mmol) was dissolved in 10 ml of absolute ethanol. A solution of 4.0 g (10.6 mmol) of the resultant compound of Example 8B in 50 ml of absolute ethanol was added dropwise. The mixture was stirred at ambient temperature for 20 min and 5-chloromethylthiazole hydrochloride was then added. After being stirred at ambient temperature for 60 h, the reaction was cooled in an ice bath, neutralized with 10% citric acid to pH ~6 and extracted with four 50 ml portions of dichloromethane. The combined organic layers were dried over $Na_2SO_4$, concentrated in vacuo and the residue was purified by silica gel chromatography using 10% methanol in dichloromethane to provide 3.88 g (78%) of the desired compound as a white foamy solid. Mass spectrum: $(M+H)^+=475$.

D. (3S,5S,1'S)-5-(1-(tert-Butyloxycarbonylamino)-2-phenylethyl)-3-((5-thiazolyl)methyl)dihydrofuran-2(3H)-one A solution of 3.88 g (8.18 mmol) of the resultant compound of Example 8C in 65 ml of dimethoxyethane was treated with 32.7 ml (32.7 mmol) of 1M aqueous lithium hydroxide. After being stirred at ambient temperature for 4 h, the bulk of the 1,2-dimethoxyethane was removed in vacuo. The remaining mixture was treated with 10% citric acid to pH 4–5 and extracted with four 50 ml portions of dichloromethane. The combined organic layers were dried over $Na_2SO_4$ and concentrated in vacuo to give the crude acid. The acid was dissolved in 50 ml of toluene, heated at reflux for 15 h. The solvent was removed in vacuo, and the residue was separated by silica gel chromatography using 50% ethyl acetate in hexane to provide 0.86 g (26%) of 3R isomer and 1.58 g (48%) of the desired compound as a white solid. $^1$H NMR (CDCl$_3$) δ1.40 (s, 9H), 1.84 (m, 1H), 2.21 (ddd, 1H), 2.82–2.99 (m, 3H), 3.07 (dd, 1H), 3.43 (dd, 1H), 3.97 (br q, 1H), 4.36 (ddd, 1H), 4.55 (br d, 1H), 7.21–7.33 (m, 5H), 7.63 (s, 1H), 8.69 (s, 1H). Mass spectrum: $(M+H)^+$=403.

E. (2S,4S,5S)-4-(tert-Butyldimethylsilyloxy)-5-(tert-butyloxycarbonylamino)-6-phenyl-2-((5-thiazolyl)methyl)hexanoic acid A solution of 1.50 g (3.73 mmol) of the resultant compound of Example 8D in 80 ml of a 2:1 mixture of 1,2-dimethoxyethane and water was treated with 14.9 ml (14.9 mmol) of 1M aqueous lithium hydroxide. After being stirred at ambient temperature for 1.5 h, the bulk of the 1,2-dimethoxyethane was removed in vacuo. The remaining mixture was treated with 10% citric acid to pH 4–5 and extracted with four 50 ml portions of diohloromethane. The combined organic layers were dried over $Na_2SO_4$ and concentrated in vacuo to give 1.48 g of the crude hydroxy acid. This hydroxy acid was dissolved in 14 ml of dry DMF and 2.64 g (17.5 mmol) of tert-butyldimethylsilyl chloride and 2.23 g (32.8 mmol) of imidazole were added. After being stirred at ambient temperature for 18 h, 28 ml of methanol was added to the mixture. Stirring was continued for 4 h and the solvents were then removed in vacuo. The residue was treated with 10% citric acid to pH 4–5 and extracted with four 50 ml portions of dichloromethane. The combined organic layers were dried over $Na_2SO_4$, concentrated in vacuo and the residue was purified by silica gel chromatography using 10% methanol in dichloromethane to provide 1.70 g (85%) of the desired compound as a white foamy solid. Mass spectrum: $(M+H)^+$=529.

Anal. Calcd for $C_{27}H_{42}N_2O_5SSi \cdot 0.5H_2O$: C, 59.64; H, 7.97; N, 5.15; Found: C, 59.71; H, 7.83; N, 5.31.

F. (2S,3S,5S)-5-((((Benzyl)oxy)carbonyl)amino)-3-(tert-butyldimethylsilyloxy)-2-(tert-butyloxycarbonylamino)-1-phenyl-6-(5-thiazolyl)hexane A solution of 500.0 mg (0.935 mmol) of the resultant compound of Example 8E, 402 μl (1.87 mmol) of diphenylphosphoryl azide and 326 μl (2.38 mmol) of triethylamine in 5 ml of dioxane was heated at 70° C. for 1 h. Benzyl alcohol (483 μl, 4.67 mmol) was subsequently added. The mixture was stirred at 80° C. for 24 h. The solvents were removed in vacuo and the residue was purified by silica gel chromatography using 10% methanol in dichloromethane to provide 598.1 mg (100%) of the desired compound as a white foamy solid. Mass spectrum: $(M+H)^+$=640.

G. (2S,3S,5S)-5-((((Benzyl)oxy)carbonyl)amino)-2-(tert-butyloxycarbonylamino)-1-phenyl-6-(5-thiazolyl)-3-hydroxyhexane A solution of 570.6 mg (0.892 mmol) of the resultant compound of Example 8F in 25 ml of tetrahydrofuran was treated with 0.89 ml of 1M solution of tetrabutylammonium fluoride in tetrahydrofuran. After being stirred at ambient temperature for 20 h, the solvent was removed in vacuo and the residue was purified by silica gel chromatography using 10% methanol in dichloromethane to provide 295.6 mg (63%) of the desired compound as a white solid. $^1$H NMR (CDCl$_3$) δ1.39 (s, 9H), 1.54 (m, 2H), 2.87 (m, 2H), 3.08 (m, 2H), 3.69 (m, 2H), 3.96 (m, 1H), 4.77 (br d, 1H), 5.08 (s, 2H), 5.11 (br s, 1H), 7.18–7.36 (m, 10H), 7.53 (s, 1H),8.67 (s, 1H). Mass spectrum: $(M+H)^+$=526.

H. (2S,3S,5S)-2,5-Diamino-1-phenyl-6-(5-thiazolyl)-3-hydroxyhexane

The resultant compound of Example 8G (201.2 mg, 0.383 mmol) was dissolved in 1 ml of acetic acid saturated with hydrogen bromide and stirred at ambient temperature for 1 h. The solvent was removed in vacuo. The residue was treated with 2 ml of saturated aqueous $NaHCO_3$, extracted with five 5 ml portions of dichloromethane. The combined organic layers were dried over $Na_2SO_4$ and concentrated in vacuo to provide 99.3 mg (89%) of the desired compound as a white solid. Mass spectrum: $(M+H)^+$=292.

I. (4S,6S,1'S)-6-(1-Amino-2-phenylethyl)-2-phenyl-4-((5-thiazolyl)methyl)-3-aza-2-bora-1-oxacyclohexane A solution of 95.7 mg (0.328 mmol) of the resultant compound of Example 8H and 40.0 mg (0.328 mmol) of phenylboric acid in 5 ml of toluene was heated at reflux and the water azeotropically removed with the aid of a Dean Stark trap until the distillate was clear. The solvent was then removed in vacuo to provided 124.3 mg (100%) of the desired compound as a resin. Mass spectrum: $(M+H)^+$=378.

J. (2S,3S,5S)-5-Amino-1-phenyl-2-(N-((5-thiazolyl)methoxycarbonyl)amino)-6-(5-thiazolyl)-3-hydroxyhexane A solution of 100.0 mg (0.265 mmol) of the resultant compound of Example 8I and 74.0 mg (0.265 mmol) of ((5-thiazolyl)methyl)-(4-nitrophenyl)carbonate in 5 ml of tetrahydrofuran was stirred at ambient temperature for 24 h. The solvent was then removed in vacuo. The residue was dissolved in 20 ml of dichloromethane, washed with three 5 ml portions of 0.5N NaOH and two 5 ml portions of water. The organic layer was dried over $Na_2SO_4$ and concentrated in vacuo. The residue was purified by silica gel chromatography using 2% methanol and 2% isopropylamine in chloroform to provide 22.8 mg (20%) of the desired compound as a white solid. Mass spectrum: $(M+H)^+$=433.

K. (2S,3S,5S)-5-(N-(N-((N-Methyl-N-((2-isopropyl-4-thiazolyl)methyl)amino)carbonyl)valinyl)amino)-1-phenyl-2-(N-((5-thiazolyl)methoxycarbonyl)amino)-6-(5-thiazolyl)-3-hydroxyhexane Using the procedure of Example 1U but replacing (2S,3S,5S)-5-amino-2-(N-((5-thiazolyl)methoxycarbonyl)amino)-1,6-diphenyl-3-hydroxyhexane with the resultant compound of Example 8J provided 16.7 mg (47%) of the desired compound as a white solid. $^1$H NMR (CDCl$_3$) δ0.90

(d, 3H), 0.94 (d, 3H), 1.38 (d, OH), 1.63 (m, 2H), 2.32 (m, 1H), 2.85 (m, 2H), 2.97 (s, 3H), 3.04 (m, 2H), 3.31 (m, 1H), 3.68 (m, 1H), 3.77 (m, 1H), 3.96 (m, 1H), 4.16 (m, 1H), 4.39 (s, 2H), 5.22 (m, 4H), 6.40 (br s, 1H), 6.80 (br d, 1H), 7.04 (s, 1H), 7.18–7.28 (m, 5H), 7.55 (s, 1H), 7.83 (s, 1H), 8.58 (s, 1H), 8.80 (s, 1H). Mass spectrum: $(M+H)^+=728$.

EXAMPLE 9

A. 4-(Chloromethyl)-2-(dimethylamino)thiazole

A mixture of 15 g (144 mmol) of N,N-dimethylthiourea and excess $MgSO_4$ in 350 ml of acetone was heated to reflux and treated dropwise with a solution of 18.3 g (144 mmol) of 1,3-dichloroacetone in 35 ml of acetone. The resulting mixture was heated at reflux for 1.5 h, allowed to cool, filtered, and concentrated in vacuo. The residue was purified by silica gel chromatography using 20% ethyl acetate in hexane to provide 14.0 g (70%) of the desired compound.

B. 2-(N,N-Dimethylamino)-4-(hydroxymethyl)thiazole

A solution of 5.186 g (29 mmol) of 4-(chloromethyl)-2-(dimethylamino)thiazole in 100 ml of 1:1 $THF/H_2O$ was cooled to 0° C. and treated dropwise with a solution of 5.73 g (29 mmol) of silver tetrafluoroborate in 50 ml of 1:1 $THF/H_2O$. After being stirred for 1 h, the mixture was filtered, the solid mass was washed with ethyl acetate, and the combined filtrates were concentrated in vacuo. The black residue was purified by silica gel chromatography to provide 0.80 g (17%) of the desired compound ($R_f$ 0.24, 6% methanol in chloroform) as an oil. $^1H$ NMR ($CDCl_3$) δ2.67 (br, 1H), 3.09 (s, 6H), 4.54 (s, 2H), 6.35 (s, 1H). Mass spectrum: $(M+H)^+=159$.

C. N-((2-(N,N-Dimethylamino)-4-thiazolyl)methoxycarbonyl)valine Methyl Ester A solution of 505 mg (3.19 mmol) of 2-(N,N-dimethylamino)-4-(hydroxymethyl)thiazole, 3.19 mmol of α-isocyanato-L-valine methyl ester, and 100 mg of 4-dimethylaminopyridine in 30 ml of dichloromethane was heated at reflux for 3 h. The resulting solution was allowed to cool, diluted with dichloromethane, washed sequentially with 10% citric acid, aqueous $Na_2CO_3$, and brine, dried over $Na_2SO_4$, and concentrated in vacuo. The residue was purified by silica gel chromatography using 2% methanol in chloroform to provide 0.95 g (95%) of the desired compound, $R_f$ 0.42 (4% methanol in chloroform). $^1H$ NMR ($CDCl_3$), δ0.84 (d, J=7 Hz, 3H), 0.93 (d, J=7 Hz, 3H), 2.12 (m, 1H), 3.11 (s, 6H), 3.73 (s, 3H), 4.24 (dd, J=8, 4 Hz, 1H), 4.99 (s, 2H), 5.26 (br d, 1H), 6.49 (s, 1H). Mass spectrum: $(M+H)^+=316$.

D. N-((2-(N,N-Dimethylamino)-4-thiazolyl)methoxycarbonyl)valine

Using the procedure of Example 1T, but replacing the resultant compound of Example 1S with the resultant compound of Example 9C provided the desired compound. Mass spectrum: $(M+H)^+=302$.

E. (2S,3S,5S)-5-(N-(N-((2-(N,N-Dimethylamino)-4-thiazolyl)methoxycarbonyl)valinyl)amino)-2-(N-((5-thiazolyl)methoxycarbonyl)amino)-1,6-diphenyl-3-hydroxyhexane Using the procedure of Example 1U but replacing N-((N-methyl-N-((2-isopropyl-4-thiazolyl)methyl)amino)carbonyl)-L-valine with the resultant compound of Example 9D provided, after silica gel chromatography using 2% methanol in chloroform, 100 mg of the desired compound ($R_f$ 0.49, 10% methanol in chloroform), mp. 162°–165° C. Mass spectrum: $(M+H)^+=709$.

EXAMPLE 10

(2S,3S,5S)-2-(N-(N-((2-(N,N-Dimethylamino)-4-thiazolyl)methoxycarbonyl)valinyl)amino)-5-(N-((5-thiazolyl)methoxycarbonyl)amino)-1,6-diphenyl-3-hydroxyhexane Using the procedure of Example 1U but replacing N-((N-methyl-N-((2-isopropyl-4-thiazolyl)methyl)amino)carbonyl)-L-valine with the resultant compound of Example 9D and replacing (2S,3S,5S)-5-amino-2-(N-((5-thiazolyl)methoxycarbonyl)amino)-1,6-diphenyl-3-hydroxyhexane with (2S,3S,5S)-2-amino-5-(N-((5-thiazolyl)methoxycarbonyl)amino)-1,6-diphenyl-3-hydroxyhexane provided, after silica gel chromatography using 2% methanol in chloroform, 25 mg (10%) of the desired compound ($R_f$ 0.49, 10% methanol in chloroform), mp. 157°–159° C. Mass spectrum: $(M+H)^+=709$.

EXAMPLE 11

A. 4-((Amino)thiocarbonyl)morpholine

A solution of 3.35 g (18.8 mmol) of thiocarbonyl diimidazole in 100 ml of THF was treated with 0.82 ml (9.4 mmol) of morpholine. After being stirred at ambient temperature for 3.5 h, an additional 0.82 ml portion of morpholine was added, and stirring was continued. After 6 h, the solution was treated with excess concentrated aqueous ammonia, and stirred overnight. The resulting solution was concentrated in vacuo, taken up in chloroform, separated from the aqueous phase, dried over $Na_2SO_4$, and concentrated. Purification of the residue by silica gel chromatography using ethyl acetate provided 1.85 g (76%) of the desired compound, $R_f$ 0.17 (10% methanol in chloroform), as a white solid. $^1HNMR$ ($CDCl_3$) δ3.76 (m, 4H), 3.83 (m, 4H), 5.75 (br, 2H). Mass spectrum: $(M+H)^+=147$.

B. Ethyl 2-(4-Morpholinyl)thiazole-4-carboxylate

A mixture of 1.85 g (12.7 mmol) of 4-((amino)thiocarbonyl)morpholine, 1.59 ml (12.7 mmol) of ethyl bromopyruvate, and excess $MgSO_4$ in 50 ml of acetone was heated at reflux for 2 h. The resulting mixture was allowed to cool, filtered, and concentrated in vacuo. The residue was taken up in chloroform, washed with aqueous $NaHCO_3$, dried over $Na_2SO_4$, and concentrated. Silica gel chromatography using 1% methanol in chloroform provided 1.7 g (55%) of the desired compound, $R_f$ 0.70 (ethyl acetate). Mass spectrum: $(M+H)^+=243$.

C. 2-(4-Morpholinyl)-4-(hydroxymethyl)thiazole

A solution of 7.0 ml (7.0 immol) of lithium aluminum hydride in toluene was diluted with 10 ml of THF, cooled to 0° C., and treated with a solution of 1.7 g (7.0 mmol) of ethyl 2-(4-morpholinyl)thiazole-4-carboxylate in 25 ml of THF. The resulting solution was stirred for 1 h, quenched cautiously with aqueous Rochelle's salts, diluted with chloroform, filtered, dired over $Na_2SO_4$, and concentrated in vacuo. Silica gel chromatography using 2–4% methanol in chloroform provided 856 mg (61%) of the desired compound, $R_f$ 0.16 (4% methanol in chloroform). $^1H$ NMR ($CDCl_3$) δ2.44 (br, 1H), 3.46 (t, J=5 Hz, 4H), 3.81 (t, J=5 Hz, 1H), 4.55 (br s, 2H), 6.45 (s, 1H). Mass spectrum: (M+H)⁺ =200.

D. N-((2-(4-Morpholinyl)-4-thiazolyl)methoxycarbonyl)valine Methyl Ester

Using the procedure of Example 9C but replacing 2-(N,N-dimethylamino)-4-(hydroxymethyl)thiazole with 2-(4-morpholinyl)-4-(hydroxymethyl)thiazole provided, after silica gel chromatography using 1% methanol in chloroform, the desired compound, $R_f$ 0.54 (4% methanol in chloroform), in 65% yield. ¹H NMR (CDCl₃) δ0.97 (d, J=7 Hz, 3H), 1.00 (d, J=7 Hz, 3H), 2.25 (m, 1H), 3.50 (dd, J=5, 4 Hz, 2H), 3.76 (s, 3H), 3.84 (dd, J=5, 4 Hz, 2H), 4.67 (dd, J=9, 5 Hz, 1H), 7.63 (br d, 1H), 8.02 (s, 1H).

E. N-((2-(4-Morpholinyl)-4-thiazolyl)methoxycarbonyl)valine

Using the procedure of Example 1T, but replacing the resultant compound of Example 1S with the resultant compound of Example 11D provided the desired compound.

F. (2S,3S,5S)-5-(N-(N-((2-(4-Morpholinyl)-4-thiazolyl)methoxycarbonyl)valinyl)amino)-2-(N-((5-thiazolyl)methoxycarbonyl)amino)-1,6-diphenyl-3-hydroxyhexane Using the procedure of Example 1U but replacing N-((N-methyl-N-((2-isopropyl-4-thiazolyl)methyl)amino)carbonyl)-L-valine with the resultant compound of Example 11E provided, after silica gel chromatography using 2% methanol in chloroform, 201 mg (92%) of the desired compound ($R_f$ 0.19, 4% methanol in chloroform), mp. 169°–170° C. Mass spectrum: (M+H)⁺=751.

EXAMPLE 12

(2S,3S,5S)-2-(N-(N-((2-(4-Morpholinyl)-4-thiazolyl)methoxycarbonyl)valinyl)amino)-5-(N-((5-thiazolyl)methoxycarbonyl)amino)-1,6-diphenyl-3-hydroxyhexane Using the procedure of Example 1U but replacing N-((N-methyl-N-((2-isopropyl-4-thiazolyl)methyl)amino)carbonyl)-L-valine with the resultant compound of Example 11E and replacing (2S,3S,5S)-5-amino-2-(N-((5-thiazolyl)methoxycarbonyl)amino)-1,6-diphenyl-3-hydroxyhexane with (2S,3S,5S)-2-amino-5-(N-((5-thiazolyl)methoxycarbonyl)amino)-1,6-diphenyl-3-hydroxyhexane provided, after silica gel chromatography using 2% methanol in chloroform, 196 mg (90%) of the desired compound ($R_f$ 0.19, 4% methanol in chloroform), mp. 146°–148° C. Mass spectrum: (M+H)⁺=751.

EXAMPLE 13

A. 1-(Amino)thiocarbonyl)pyrrolidline

Using the procedure of Example 11A but replacing morpholine with pyrrolidine, and stirring the solution for six days after addition of aqueous ammonia provided the desired compound. ¹H NMR (CDCl₃) δ1.97 (m, 2H), 2.11 (m, 2H), 3.38 (br t, 2H), 3.85 (br t, 2H), 5.56 (br, 2H). Mass spectrum: (M+H)⁺=131.

B. Ethyl 2-(1-Pyrrolidinyl)thiazole-4-carboxylate

Using the procedure of Example 11B but replacing 4-((amino)thiocarbonyl)morpholine with 1-((amino)thiocarbonyl)pyrrolidine provided the desired compound. ¹H NMR (CDCl₃) δ1.37 (t, J=7 Hz, 3H), 2.04 (m, 4H), 3.51 (m, 4H), 4.35 (q, J=7 Hz, 2H), 7.37 (s, 1H). Mass spectrum: (M+H)⁺=227.

C. 2-(1-Pyrrolidinyl)-4-(hydroxymethyl)thiazole

Using the procedure of Example 11C but replacing ethyl 2-(4-morpholinyl)thiazole-4-carboxylate with ethyl 2-(1-pyrrolidinyl)thiazole-4-carboxylate provided, after silica gel chromatography using 2–4% methanol in chloroform, the desired compound ($R_f$ 0.26, 4% methanol in chloroform) in 53% yield. ¹H NMR (CDCl₃) δ2.04 (m, 4H), 2.75 (br, 1H), 3.45 (m, 4H), 4.56 (s, 2H), 6.32 (s, 1H). Mass spectrum: (M+H)⁺=185.

D. N-((2-(1-Pyrrolidinyl)-4-thiazolyl)methoxycarbonyl)valine Methyl Ester

Using the procedure of Example 9C but replacing 2-(N,N-dimethylamino)-4-(hydroxymethyl)thiazole with 2-(1-pyrrolidinyl)-4-(hydroxymethyl)thiazole provided, after silica gel chromatography using 1.5% methanol in chloroform, the desired compound ($R_f$ 0.34). ¹H NMR (CDCl₃) δ0.89 (d, J=7 Hz, 6H), 2.04 (m, 4H), 2.14 (m, 1H), 3.46 (m, 4H), 3.74 (s, 3H), 4.30 (dd, J=9, 4 Hz, 1H), 5.01 (s, 2H), 5.33 (br d, 1H), 6.44 (s, 1H). Mass spectrum: (M+H)⁺=342.

E. N-((2-(1-Pyrrolidinyl)-4-thiazolyl)methoxycarbonyl)valine

Using the procedure of Example 1T, but replacing the resultant compound of Example 1S with the resultant compound of Example 13D provided the desired compound.

F. (2S,3S,5S)-5-(N-(N-((2-(1-Pyrrolidinyl)-4-thiazolyl)methoxycarbonyl)valinyl)amino)-2-(N-((5-thiazolyl)methoxycarbonyl)amino)-1,6-diphenyl-3-hydroxyhexane Using the procedure of Example 1U but replacing N-((N-methyl-N-((2-isopropyl-4-thiazolyl)methyl)amino)carbonyl)-L-valine with the resultant compound of Example 13E provided, after silica gel chromatography using 1–3% methanol in chloroform, 120 mg (53%) of the desired compound, mp. 146°–148° C. Mass spectrum: (M+H)⁺=735.

EXAMPLE 14

(2S,3S,5S)-2-(N-(N-((2-(1-Pyrrolidinyl}-4-thiazolyl)methoxycarbonyl)valinyl)amino)-5-(N-((5-thiazolyl)methoxycarbonyl)amino)-1,6-diphenyl-3-hydroxyhexane Using the procedure of Example 1U but replacing N-((N-methyl-N-((2-isopropyl-4-thiazolyl)methyl)amino)carbonyl)-L-valine with the resultant compound of Example 13E and replacing (2S,3S,5S)-5-amino-2-(N-((5-thiazolyl)methoxycarbonyl)amino)-1,6-diphenyl-3-hydroxyhexane with (2S,3S,5S)-2-amino-5-(N-((5-thiazolyl)methoxycarbonyl)amino)-1,6-diphenyl-3-hydroxyhexane provided, after silica gel chromatography using 2% methanol in chloroform, 89 mg (39%) of the desired compound ($R_f$ 0.16, 4% methanol in chloroform), mp. 165°–167° C. Mass spectrum: (M+H)⁺=735.

EXAMPLE 15

A. 2-Isopropyl-4-(((N-cyclopropyl)amino)methyl)thiazole

A solution of 1.8 g (10.2 mmol) of 4-(chloromethyl)-2-isopropylthiazole hydrochloride in 10 ml of chloroform was added dropwise with stirring to 10 ml of cyclopropylamine. The resulting solution was stirred at ambient temperature for 16 h, concentrated in vacuo, and purified by silica gel chromatography using 5% methanol in chloroform to provide 0.39 g (19%) of the desired compound. $^1$H NMR (DMSO-d$_6$) δ0.24 (m, 2H), 0.35 (m, 2H),1.30 (d, J=7 Hz, 6H), 2.10 (tt, J=12, 3 Hz, 1H), 3.23 (heptet, J=7 Hz, 1H), 3.77 (s, 2H), 7.21 (s, 1H). Mass spectrum: (M+H)$^+$=197.

B. N-((N-Cyclopropyl-N-((2-isopropyl-4-thiazolyl)methyl)amino)carbonyl)-L-alanine Methyl Ester Using the procedure of Example 1S, but replacing N-(((4-nitrophenyl)oxy)carbonyl)-L-valine methyl ester with N-(((4-nitrophenyl)oxy)carbonyl)-L-alanine methyl ester and replacing 2-isopropyl-4-(((N-methyl)amino)methyl)thiazole with the resultant compound of Example 15A provided, after silica gel chromatography using 1% methanol in chloroform, the desired compound (R$_f$ 0.54, 5% methanol in chloroform)in 56% yield. $^1$H NMR (DMSO-d$_6$) δ0.70 (m, 2H), 0.80 (m, 2H), 1.30 (d, J=7 Hz, 6H), 1.34 (d, J=7 Hz, 3H), 2.57 (m, 1H), 3.22 (heptet, J=7 Hz, 1H), 3.62 (s, 3H), 4.23 (pentet, J=7 Hz, 1H), 4.44 (AA', 2H), 6.54 (d, J=7 Hz, 1H), 7.05 (s, 1H). Mass spectrum: (M+H)$^+$=326.

C. N-((N-Cyclopropyl-N-((2-isopropyl-4-thiazolyl)methyl)amino)carbonyl)-L-alanine Using the procedure of Example 1T, but replacing the resultant compound of Example 1S with the resultant compound of Example 15B provided the desired compound.

D. (2S,3S,5S)-5-(N-(N-((N-Cyclopropyl-N-((2-isopropyl-4-thiazolyl)methyl)amino)carbonyl)alaninyl)amino)-2-(N-((5-thiazolyl)methoxycarbonyl)amino)-1,6-diphenyl-8-hydroxyhexane Using the procedure of Example 1U but replacing N-((N-methyl-N-((2-isopropyl-4-thiazolyl)methyl)amino)carbonyl)-L-valine with the resultant compound of Example 15C provided, after silica gel chromatography using 1% methanol in chloroform, 74 mg (40%) of the desired compound (R$_f$ 0.25, 5% methanol in chloroform), mp. 65°–67° C. Mass spectrum: (M+H)$^+$=719. Anal. Calcd for C$_{37}$H$_{46}$N$_6$O$_5$S$_2$.0.5H$_2$O: C, 61.05; H, 6.51; N, 11.54. Found: C, 61.08; H, 6.32; N, 11.44.

EXAMPLE 16

A. 2-Isopropylthiazole-4-carboxaldehyde

A solution of ethyl 2-isopropylthiazole-4-carboxylate (1 mmol) in 50 ml of dry dichloromethane was cooled to –78° C. under N$_2$ atmosphere and treated dropwise with 1.2 mmol of diisobutylaluminum hydride (1.5M in toluene). The resulting solution was stirred for 0.5 h, quenched with aqueous Rochelle salts, extracted with dichloromethane, dried over Na$_2$SO$_4$, and concentrated in vacuo to provide the crude desired compound.

B. 4-(1-Hydroxyethyl)-2-isopropylthiazole

A solution of the resultant compound of Example 16A (0.5 mmol) in 25 ml of dry THF was cooled to –20° C. under Ar atmosphere, treated with 0.5 mmol of methylmagnesium chloride (3.0M in THF), stirred for 15 min, and quenched with water. The mixture was extracted with ethyl acetate, dried over Na$_2$SO$_4$, and concentrated in vacuo to provide the crude desired compound.

C. N-(1-(2-Isopropyl-4-thiazolyl)ethoxycarbonyl)valine Methyl Ester

Using the procedure of Example 5D but replacing 4-(hydroxymethyl)-2-isopropylthiazole with 4-(1-hydroxyethyl)-2-isopropylthiazole provided the desired compound.

D. N-(1-(2-Isopropyl-4-thiazolyl)ethoxycarbonyl)valine

Using the procedure of Example 1T, but replacing the resultant compound of Example 1S with the resultant compound of Example 16C provided the desired compound.

E. (2S,3S,5S)-5-(N-(N-(1-(2-Isopropyl-4-thiazolyl)ethoxycarbonyl)valinyl)amino)-2-(N-((5-thiazolyl)methoxycarbonyl)amino)-1,6-diphenyl-3-hydroxyhexane Using the procedure of Example 1U but replacing N-((N-methyl-N-((2-isopropyl-4-thiazolyl)methyl)amino)carbonyl)-L-valine with the resultant compound of Example 16D provided the desired compound.

EXAMPLE 17

A. N-((N-Cyclopropyl-N-((2-isopropyl-4-thiazolyl)methyl)amino)carbonyl)-L-valine Methyl Ester Using the procedure of Example 1S, but replacing 2-isopropyl-4-(((N-methyl)amino)methyl)thiazole with the resultant compound of Example 15A provided, after silica gel chromatography using 1% methanol in chloroform, the desired compound (R$_f$ 0.64, 5% methanol in chloroform) in 91% yield. $^1$H NMR (DMSO-d$_6$) δ0.73 (m, 2H), 0.82 (m, 2H), 0.90 (d, J=7 Hz, 6H), 1.30 (d, J=7 Hz, 6H), 2.10 (octet, J=7 Hz, 1H), 2.62 (m, 1H), 3.23 (heptet, J=7 Hz, 1H), 3.64 (s, 3H), 4.10 (dd, J=9, 6 Hz, 1H), 4.45 (AA', 2H), 6.29 (d, J=9 Hz, 1H), 7.06 (s, 1H). Mass spectrum: (M+H)$^+$=354.

B. N-((N-(Cyclopropyl-N-((2-isopropyl-4-thiazolyl)methyl)amino)carbonyl)-L-valine Using the procedure of Example 1T, but replacing the resultant compound of Example 1S with the resultant compound of Example 17A provided the desired compound.

C. (2S,3S,5S)-5-(N-(N-((N-Cyclopropyl-N-((2-isopropyl-4-thiazolyl)methyl)amino)carbonyl)valinyl)amino)-2-(N-((5-thiazolyl)methoxycarbonyl)amino)-1,6-diphenyl-3-hydroxyhexane Using the procedure of Example 1U but replacing N-((N-methyl-N-((2-isopropyl-4-thiazolyl)methyl)amino)carbonyl)-L-valine with the resultant compound of Example 17B provided, after silica gel chromatography using 1% methanol in chloroform, 85 mg (48%) of the desired compound (R$_f$ 0.30, 5% methanol in chloroform), mp. 65°–66° C. Mass spectrum: (M+H)$^+$=747. Anal. Calcd for C$_{39}$H$_{50}$N$_6$O$_5$S$_2$: C, 62.71; H, 6.75; N, 11.25. Found: C, 62.74; H, 6.61; N, 11.03.

EXAMPLE 18

A. 4-Chloromethyl-4-hydroxy-2-isopropyloxazoline

To a solution of isobutyramide (9.876 g, 0.1122 mol) in acetone (130 mL) was added 1,3-dichloroacetone (10.0 g, 0.0748 mol), NaHCO$_3$ (9.429 g, 0.1122 mol), and MgSO$_4$ (18.01 g, 0.1496 mol). The mixture was heated at reflux under argon for 63 hrs, then cooled to room temperature, vacuum filtered, and concentrated in vacuo to a dark brown semi-solid. The residue was purified by SiO$_2$ flash chromatography using a gradient of EtOAc/CH$_2$Cl$_2$ (5%, 10%, 20%, 40%) to obtain the desired product as an orange liquid (6.06 g, 0.0341 mol, 46%): $^1$H NMR (CDCl$_3$) δ1.20–1.28 (m, 6H), 2.56–2.72 (m, 1H), 3.70 (s, 2H), 4.18 (d, J=9.6 Hz, 1H), 4.38 (d, J=9.6 Hz, 1H). Mass spectrum: (M+H)$^+$=178, 180.

B. 4-(Chloromethyl-2-isopropyloxazole

A solution of 4-chloromethyl-4-hydroxy-2-isopropyloxazoline (4.88 g, 0.0275 mol) in 1,2-dichloroethane (20 mL) was added to a solution of SOCl$_2$ (2.40 mL, 0.0329 mol) in 1,2-dichloroethane (80 mL) at 0° C. under argon, and the solution was heated to 70° C. After 15 min at 70° C., the reaction was cooled to room temperature and the solvent removed by rotary evaporation in vacuo. Drying the residue on high vacuum gave the desired compound as a brown semi-solid (4.20 g, 0.0263 mol, 96%): $^1$H NMR (CDCl$_3$) δ1.36 (d, J=7.5 Hz, 6H), 3.03–3.18 (m, 1H), 4.50 (s, 2H), 7.56 (s 1H). Mass spectrum: (M+H)$^+$=160, 162.

C. 2-Isopropyl-4-(((N-methyl)amino)methyl)oxazole

To 40% aqueous methylamine (100 mL) was added dropwise a suspension of 4-chloromethyl-2-isopropyloxazole (4.20 g, 0.0263 mol) in p-dioxane/H$_2$O (1:1 (v/v), 20 mL) over a 25 min period. After stirring for 45 min at ambient temperature, the volume was reduced to ca. 50 mL by rotary evaporation in vacuo, and NaCl was added. The aqueous was extracted with CHCl$_3$ (4×100 mL), and the combined extract was dried over Na$_2$SO$_4$ and concentrated in vacuo. The resulting brown liquid was chromatographed on a 200 g SiO$_2$ flash column with 2% iPrNH$_2$/CH$_2$Cl$_2$ followed by a gradient of iPrNH$_2$/MeOH/CH$_2$Cl$_2$ (0.5:2:97.5, 0.5:4:95.5). Concentration in vacuo of the product-containing fractions afforded the desired compound as a golden oil (2.89 g, 0.0187 mol, 71%): $^1$H NMR (CDCl$_3$) δ1.33 (d, J=6.9 Hz, 6H), 2.46 (s, 3H), 2.99–3.14 (m, 1H), 3.64 (s, 2H), 7.42 (s, 1H). Mass spectrum: (M+H)$^+$=155, (M+NH$_4$)$^+$=172.

D. N-((N-Methyl-N-((2-isopropyl-4-oxazolyl)methyl)amino)carbonyl)-L-valine Methyl Ester A solution of N-(((4-nitrophenyl)oxy)carbonyl)-L-valine methyl ester (0.903 g, 0.00305 mol) in anhydrous DMF (6 mL) was added to a solution of 2-isopropyl-4-(((N-methyl)amino)methyl)oxazole (9, 0.470 g, 0.00305 mol) in anhydrous DMF (6 mL) under argon, and the yellow solution was stirred at room temperature for 30 min. Solvent was removed by rotary evaporation in vacuo and the resulting oil dried on high vacuum for 1 hr. The residue was applied to a 150 g SiO$_2$ flash column and eluted with 20% EtOAc/CH$_2$Cl$_2$ and 3% MeOH/CH$_2$Cl$_2$. The material obtained after concentration of the product fractions was repurified on a 100 g SiO$_2$ flash column with a gradient of MeOH/CH$_2$Cl$_2$ (1%, 2%, 3%) to obtain the desired compound as an oil (0.515 g, 0.00165 mol, 54%): $^1$H NMR (CDCl$_3$) δ0.97 (dd, J$_1$=9 Hz, J$_2$=6.9 Hz, 6H), 1.33 (d, J=6.9 Hz, 6H), 2.11–2.23 (m, 1H), 2.98 (s, 3.00–3.13 (m, 1H), 3.77 (s, 3H), 4.23–4.36 (m, 2H), 4.36–4.42 (m, 1H), 5.79–5.86 (br d, 1H), 7.46 (s, 1H). Mass spectrum: (M+H)$^+$=312.

E. N-((N-Methyl-N-((2-isopropyl-4-oxazolyl)methyl)amino)carbonyl)-L-valine

To a solution of the resultant compound of Example 18D 10 (0.511 g, 0.00164 mol) in p-dioxane (10 mL) and H$_2$O (5 mL) was added LiOH monohydrate (0.103 g, 0.00246 mol). After stirring at room temperature for 1 hr, the p-dioxane was removed by rotary evaporation in vacuo, and the remaining aqueous solution was treated with 1N aq HCl (2.46 mL) and extracted with ethyl acetate (4×100 mL). The combined organic extract was washed with saturated brine and dried for 15 mins over Na$_2$SO$_4$. Concentration in vacuo followed by CH$_2$Cl$_2$ chases (2×) afforded the desired compound as a white solid (0.480 g, 0.00161 mol, 98%): $^1$H NMR (DMSO-d$_6$) δ0.90 (dd, J$_1$=6.9 Hz, J$_2$=2.4 Hz, 6H), 1.24 (d, J=6.9 Hz, 6H), 1.99–2.12 (m, 1H), 2.83 (s, 3H), 2.96–3.10 (m, 1H), 3.96 (dd, J$_1$=8.4 Hz, J$_2$=6 Hz, 1H), 4.19–4.32 (m, 2H), 6.26 (d, J=8.4 Hz, 1H), 7.80 (s, 1H). Mass spectrum: (M+H)$^+$=298

F. (2S,3S,5S)-5-(N-(N-((N-Methyl-N-((2-isopropyl-4-oxazolyl)methyl)amino)carbonyl)valinyl)amino)-2-(N-((5-thiazolyl)methoxycarbonyl)amino)-1,6-diphenyl-3-hydroxyhexane Using the procedure of Example 1U but replacing N-((N-methyl-N-((2-isopropyl-4-thiazolyl)methyl)amino)carbonyl)-L-valine with N-((N-methyl-N-((2-isopropyl-4-oxazolyl)methyl)amino)carbonyl)-L-valine provided, after silica gel chromatography using 3–5–7% methanol in chloroform, 70 mg, (53%) of the desired compound. $^1$H NMR (DMSO-d$_6$) δ0.74 (d, J=6.3 Hz, 6H), 1.23 (d, J=6.9 Hz, 6H), 1.38–1.51 (m, 2H), 1.80–1.94 (m, 1H), 2.54–2.74 (m, 5H), 2.83 (s, 3H), 2.94–3.09 (m, 1H), 3.53–3.63 (m, 3.76–3.97 (m, 2H), 4.08–4.35 (m, 3H), 4.63 (d, J=6 Hz, 1H), 5.08–5.19 (m, 2H), 5.90 (d, J=8.7 Hzm 1H), 6.89 (d, J=9 Hz, 1H), 7.07–7.25 (m, 12H), 7.68 (d, J=8.7 Hz, 1H), 7.77 (s, 1H), 7.86 (s, 1H), 9.05 (s, 1H). High resolution mass spectrum: calcd for C$_{37}$H$_{49}$N$_6$O$_6$S: 705.3434. Found: 705.3431 (M+H)$^+$. Anal. Calcd for C$_{37}$H$_{48}$N$_6$O$_6$S·0.5H$_2$O: C, 62.25; H, 6.92; N, 11.77. Found: C, 62.35; H, 6.86; N, 11.34.

EXAMPLE 19

A. Methyl Isocyanide

A 100 mL 3-neck flask (equipped with septum, stopper, and a short path mini distillation head with cow collector cooled to −78° C.) was charged with p-toluenesulfonyl chloride (36.25 g, 0.1901 mol) and quinoline (60 mL). The vigorously stirred solution was heated to 75° C. with the system under vacuum (H$_2$O aspirator with trap cooled to −40° C.). Neat N-methylformamide (7.50 g, 0.127 mol) was added via syringe in small portions over 15 mins. The increasingly viscous solution was heated for 10 mins, at which time gas evolution had ceased. Material in the cow collector and in the vacuum trap were combined and vacuum distilled to provide the compound as a colorless liquid (2.06 g, 0.0502 mol, 39%).

B. 5-((Diethoxy)methyl)oxazole

Prepared according to the procedure of Schöllkopf (*J. Am. Chem. Soc.* 112 (10) 4070 (1990)). To a solution of methyl isocyanide (2.88 g, 0.0702 mol) in THF (50 mL) under argon at −78° C. was added dropwise n-butyllithium solution (1.6M in hexanes, 44 mL) over 15 mins. After stirring for an additional 20 mins at −78° C., a solution of ethyl diethoxyacetate (12.62 g, 0.0702 mol) in THF (15 mL) was added dropwise over 20 mins. The bath was allowed to warm to −30° C. over the next 2 hrs and the reaction was then stirred at 0° C. for 30 mins. The reaction was quenched at 0° C. with glacial HoAc (4.22 g, 0.0702 mol) and the solvent was removed by rotary evaporation in vacuo. The golden solid was partitioned with $H_2O$ (45 mL) and EtOAc (200 mL), and the aqueous extracted with EtOAc (2×200 mL). The combined organic was washed with satd aq NaCl, dried over $Na_2SO_4$, and concentrated in vacuo to a brown oil. Chromatography on a 300 g $SiO_2$ flash column with a gradient of EtOAc/hexane (10%, 15%, 20%) afforded the desired compound as a colorless liquid (7.46 g, 0.0436 mol, 62%): $^1H$ NMR ($CDCl_3$) δ1.25 (t, J=6.9 Hz, 6H), 3.56–3.70 (m, 4H), 5.62 (s, 1H), 7.26 (s, 1H), 7.86 (s, 1H). Mass spectrum: $(M+H)^+=172$.

C. 5-Oxazolecarboxaldehyde

A flask was charged with 5-((diethoxy)methyl)oxazole (1.02 g, 0.00596 mol) and cooled to 0° C. A solution of trifluoroacetic acid/$CH_2Cl_2$ (1:1 (v/v), 6.7 mL) and $H_2O$ (0.39 mL) was added and the solution stirred at 0° C. for 10 min. The solvent was removed in vacuo, and the residue was treated with toluene and concentrated. Chromatography on a 100 g $SiO_2$ flash column with a gradient of EtOAc/hexane (20%, 30%, 40%) afforded the desired compound as a colorless liquid (0.344 g, 0.00354 mol, 59%): $^1H$ NMR ($CDCl_3$) δ7.89 (s, 1H), 8.12 (s, 1H), 9.87 (s, 1H). Mass spectrum: $(M+H)^+=98$.

D. 5-(Hydroxymethyl)oxazole

A solution of 5-oxazolecarboxaldehyde (0.627 g, 0.00646 mol) in MeOH (10 mL) under argon at 0° C. was treated with $NaBH_4$ (0.247 g, 0.00646 mol). After 5 mins the reaction was quenched with acetone and the solvent removed by rotary evaporation in vacuo. Chromatography on a 100 g $SiO_2$ flash column with a gradient of MeOH/$CH_2Cl_2$ (5%, 10%) afforded the desired compound as a colorless oil (0.408 g, 0.00412 mol, 64%): $^1H$ NMR ($CDCl_3$) δ2.03 (t, J=6.0 Hz, 1H), 4.70 (d, J=6.0 Hz, 2H), 7.04 (s, 1H), 7.87 (s, 1H). MS (CI/$NH_3$) m/e 117 (m+$NH_4$), 100 (m+H).

E. ((5-Oxazolyl)methyl)-(4-nitrophenyl)carbonate

A solution of 5-(hydroxymethyl)oxazole (1.31 g, 0.0132 mol) in $CH_2Cl_2$ (70 mL) under argon at 0° C. was treated with triethylamine (1.90 mL, 0.0139 mol) and 4-nitrophenyl chloroformate (2.75 g, 0.0132 mol). After stirring at 0° C. for 2.5 hrs, solvent was removed by rotary evaporation in vacuo and the yellow solid was dried on vacuum pump to provide the crude desired compound.

F. (2S,3S,5S)-2-Amino-5-((5-oxazolyl)methoxycarbonyl)amino)-1,6-diphenyl-3-hydroxyhexane A solution of crude ((5-oxazolyl)methyl)-(4-nitrophenyl)carbonate (made from 0.0132 mol 5-(hydroxymethyl)oxazole) in THF (110 mL) under argon was treated with a solution of (2S,3S,5S)-2,5-diamino-1,6-diphenyl-3-hydroxyhexane (3.76 g, 0.0132 mol) in THF (20 mL), and the reaction stirred at room temperature for 16 hrs. Solvent was removed by rotary evaporation in vacuo and the yellow foam dried on a vacuum pump. Chromatography on a 200 g $SiO_2$ flash column with 5% MeOH/$CH_2Cl_2$, 2% iPr$NH_2$/$CH_2Cl_2$, and a gradient of iPr$NH_2$/MeOH/$CH_2Cl_2$ (2:2:96, 2:5:93) afforded a mixture (1.74 g) of the desired compound and: (2S,3S,5S)-5-amino-2-(N-((5-oxazolyl)methoxycarbonyl)amino)-1,6-diphenyl-3-hydroxyhexane. The mixture was applied to a 150 g $SiO_2$ flash column (deactivated with 2% iPr$NH_2$/$CH_2Cl_2$) and eluted with 2% iPr$NH_2$/$CH_2Cl_2$ to afford the desired compound as a gummy light yellow solid (0.382 g, 0.933 mmol, 7%): $^1H$ NMR (DMSO-$d_6$) δ1.16–1.30 (m, 1H), 1.36–1.47 (m, 1H), 2.56–2.66 (m, 2H), 2.75–2.85 (m, 1H), 2.89–3.01 (m, 1H), 3.53–3.71 (m, 3H), 4.97 (d, J=2.4 Hz, 2H), 7.01 (d, J=9 Hz, 1H), 7.11–7.32 (m, 14H), 8.36 (s, 1H). Mass spectrum: $(M+H)^+=410$.

G. (2S,3S,5S)-5-(N-(N-((N-Methyl-N-((2-isopropyl-4-oxazolyl)methyl)amino)carbonyl)valinyl)amino)-2-(N-((5-oxazolyl)methoxycarbonyl)amino)-1,6-diphenyl-3-hydroxyhexane Using the procedure of Example 1U but replacing (2S,3S,5S)-5-amino-2-(N-((5-thiazolyl)-methoxycarbonyl)amino)-1,6-diphenyl-3-hydroxyhexane with (2S,3S,5S)-5-amino-2-(N-((5-oxazolyl)methoxycarbonyl)amino)-1,6-diphenyl-3-hydroxyhexane and replacing N-((N-methyl-N-((2-isopropyl-4-thiazolyl)methyl)amino)carbonyl)-L-valine with N-((N-methyl-N-((2-isopropyl-4-oxazolyl)methyl)amino)carbonyl)-L-valine provided, after silica gel chromatography using a gradient of 1%–4% methanol in dichloromethane, 145 mg (80%) of the desired compound. $^1H$ NMR ($CDCl_3$) δ0.74 (d, J=6.9 Hz, 6H), 1.23 (d, J=6.9 Hz, 6H), 1.39–1.50 (m, 2H), 1.80–1.94 (m, 1H), 2.56–2.74 (m, 4H), 2.83 (s, 3H), 2.94–3.09 (m, 1H), 3.52–3.62 (m, 1H), 3.72–3.84 (m, 1H), 3.88–3.92 (m, 1H), 4.08–4.35 (m, 3H), 4.62 (d, J=6Hz, 1H), 4.94 (s, 2H), 5.91 (d, J=8.4 Hz, 1H), 6.89 (d, J=9 Hz, 1H), 7.06–7.26 (m, 11H), 7.69 (d, J=9 Hz, 1H), 7.77 (s, 1H), 8.35 (s, 1H). Mass spectrum: $(M+NH_4)^+=706$; $(M+H)^+=689$. Anal. Calcd for $C_{37}H_{48}N_6O_7 \cdot 0.5\ H_2O$: C, 63.68; H, 7.08; N, 12.04. Found: C, 63.50; H, 7.13; N, 11.60.

EXAMPLE 20

(2S,3S,5S)-5-(N-(N-((N-Methyl-N-((2-isopropyl-4-thiazolyl)methyl)amino)carbonyl)valinyl)amino)-2-(N-((5-oxazolyl)methoxycarbonyl)amino)-1,6-diphenyl-3-hydroxyhexane Using the procedure of Example 1U but replacing (2S,3S,5S)-5-amino-2-(N-((5-thiazolyl)methoxycarbonyl)amino)-1,6-diphenyl-3-hydroxyhexane with (2S,3S,5S)-5-amino-2-(N-((5-oxazolyl)methoxycarbonyl)amino)-1,6-diphenyl-3-hydroxyhexane provided, after silica gel chromatography using 1% methanol in chloroform, 88 mg (55%) of the desired compound ($R_f$ 0.4, 5% methanol in chloroform), mp. 59°–61° C. Mass spectrum: $(M+H)^+=705$. Anal. Calcd for $C_{37}H_{48}N_6O_6S \cdot 0.5H_2O$: C, 62.25; H, 6.92; N, 11.77. Found: C, 62.23; H, 6.55; N, 11.57.

EXAMPLE 21

A. Methyl 4-isopropylthiazole-2-carboxylate

A mixture of 2.11 g (12.8 mmol) of 1-bromo-3-methylbutan-2-one (Gaudry and Marquet, Tetrahedron, 26, 5661 (1970)), 1.0 g (12.8 mmol) of ethyl thiooxamate, and 1.70 g (14 mmol) of MgSO₄ in 50 ml of acetone was heated at reflux for 3 h. After being allowed to cool, the mixture was filtered, concentrated in vacuo, and purified by silica gel chromatography using chloroform to provide 0.29 g (11%) of the desired compound ($R_f$ 0.9, 4% methanol in chloroform). ¹H NMR (DMSO-$d_6$) δ1.27 (d, J=7 Hz, 6H), 1.32 (t, J=7 Hz, 3H), 3.12 (heptet, J=7 Hz, 1H), 4.37 (q, J=7 Hz, 2H), 7.73 (s, 1H). Mass spectrum: (M+H)⁺=200.

B. 2-Hydroxymethyl)-4-isopropylthiazole

Using the procedure of Example 5B, but replacing ethyl 2-isopropyl-4-thiazolecarboxylate with methyl 4-isopropylthiazole-2-carboxylate provided, after silica gel chromatography using 2% methanol in chloroform, the desired compound ($R_f$ 0.3, 5% methanol in chloroform) in 96% yield.

C. N-((4-Isopropyl-2-thiazolyl)methoxycarbonyl)valine Methyl Ester

A solution of 1.4 mmol of α-isocyanato-valine methyl ester and 0.22 g (1.4 mmol) of 2-(hydroxymethyl)-4-isopropylthiazole in 10 ml of chloroform was heated at reflux for 3 h. After being allowed to cool, the solvent was removed in vacuo, and the residue was purified by silica gel chromatography using 2% methanol in chloroform to provide 0.23 g (52%) of the desired compound ($R_f$ 0.54, 5% methanol in dichloromethane). NMR ¹H NMR (DMSO-$d_6$) δ0.87 (d, J=7 Hz, 3H), 0.88 (d, J=7 Hz, 3H), 1.23 (d, J=7 Hz, 6H), 2.04 (octet, J=7 Hz, 1H), 3.01 (heptet, J=7 Hz, 1H), 3.73 (s, 3 H), 3.94 (dd, J=8, 6 Hz, 1H), 5.26 (AA', 2H), 7.28 (s, 1H), 7.92 (d, J=8 Hz, 1H). Mass spectrum: (M+H)⁺=315.

D. N-((4-Isopropyl-2-thiazolyl)methoxycarbonyl)valine

Using the procedure of Example 1T, but replacing the resultant compound of Example 1S with the resultant compound of Example 21C provided the desired compound.

E. (2S,3S,5S)-5-(N-(N-((4-Isopropyl-2-thiazolyl)methoxycarbonyl)valinyl)amino)-2-(N-((5-thiazolyl)methoxycarbonyl)amino)-1,6-diphenyl-3-hydroxyhexane Using the procedure of Example 1U but replacing N-((N-methyl-N-((2-isopropyl-4-thiazolyl)methyl)amino)carbonyl)-L-valine with the resultant compound of Example 21 D provided, after silica gel chromatography using 1% methanol in chloroform, 123 mg (61%) of the desired compound ($R_f$ 0.4, 5% methanol in chloroform), mp. 62–64° C. Mass spectrum: (M+H)⁺=708.

EXAMPLE 22

A. N,N-Diethylthiourea

A mixture of 6.24 g (35 mmol) of thiocarbonyl diimidazole and 3.6 ml (35 mmol) of diethylamine in 50 ml of THF was stirred at ambient temperature for 5 h. The resulting solution was treated with 20 ml of 2M aqueous NH₃ and stirred for 24 h. After removal of the solvent the residue was purified by chromatography on silica gel to provide N,N-diethylthiourea ($R_f$ 0.28, 4% methanol in chloroform).

B. Ethyl 2-(N,N-Diethylamino)thiazole-4-carboxylate

A solution of 0.972 g (7.36 mmol) of N,N-diethylthiourea and 1.02 ml (8.1 mmol) of ethyl bromopyruvate in 25 ml of acetone was treated with excess solid MgSO₄ and heated at reflux for 1 h. The resulting mixture was filtered, and concentrated in vacuo. Silica gel chromatography using CHCl₃ provided 2.36 g (38%) of the desired compound as an oil. Mass spectrum: (M+H)⁺=229.

C. 2-(N,N-Diethylamino)-4-(hydroxymethyl)thiazole

A solution of 3.14 ml of lithium aluminum hydride in toluene was diluted in a dry flask under N₂ atmosphere with 30 ml of THF. The resulting mixture was cooled to 0° C. and treated dropwise with a solution of 1.43 g (6.28 mmol) of ethyl 2-(N,N-diethylamino)thiazole-4-carboxylate in 5 ml of THF. After addition, the solution was allowed to warm slowly to ambient temperature, stirred for 1 h, recooled to 0° C., and treated with a small amount of aqueous Rochelle's salt followed by ethyl acetate. After stirring, the slurry was filtered, washed with additional ethyl acetate, and the combined filtrates were concentrated in vacuo. The residue was purified by silica gel chromatography using methanol in chloroform to provide 0.864 g (73%) of the desired compound, $R_f$ 0.17 (4% methanol in chloroform). Mass spectrum: (M+H)⁺=187.

D. N-((2-(N,N-Diethylamino)-4-thiazolyl)methoxycarbonyl)valine Methyl Ester

A solution of 5.11 mmol of α-isocyanato-valine methyl ester in 10 ml of dichloromethane was treated with 0.864 g (4.65 mmol) of 2-(N,N-diethylamino)-4-(hydroxymethyl)thiazole and 0.46 mmol of 4-dimethylaminopyridine. The resulting solution was stirred at ambient temperature for 16 h, after which it was diluted with 200 ml of chloroform, washed successively with 10% citric acid, aqueous NaHCO₃, and saturated brine. After drying over Na₂SO₄, the solvent was removed in vacuo, and the residue was chromatographed on silica gel using 1–2% methanol in chloroform to provide 1.31 g (82%) of the desired compound, $R_f$ 0.51 (4% methanol in chloroform) as an oil. ¹H NMR (CDCl₃) δ0.89 (d, J=7 Hz, 3H), 0.96 (d, J=7 Hz, 3H), 1.24 (t, J=7 Hz, 6H), 2.15 (m, 1H), 3.51 (q, J=7 Hz, 4H), 3.74 (s, 3H), 4.29 (dd, J=8, 4 Hz, 1H), 5.03 (s, 2H), 5.34 (br d, J=8 Hz, 1H), 6.42 (s, 1H). Mass spectrum: (M+H)⁺=344.

E. N-((2-(N,N-Diethylamino)-4-thiazolyl)methoxycarbonyl)valine

Using the procedure of Example 1T, but replacing the resultant compound of Example 1S with the resultant compound of Example 22D provided the desired compound.

F. (2S,3S,5S)-5-(N-(N-((2-(N,N-Diethylamino)-4-thiazolyl)methoxycarbonyl)valinyl)amino)-2-(N-((5-thiazolyl)methoxycarbonyl)amino)-1,6-diphenyl-3-hydroxyhexane Using the procedure of Example 1U but replacing N-((N-methyl-N-((2-isopropyl-4-thiazolyl)methyl)amino)carbonyl)-L-valine with the resultant compound of Example 22E provided the desired compound.

EXAMPLE 23

A. 2-(N,N-Dimethylamino)-4-(((N-methyl)amino)methyl)thiazole

Using the procedure of Example 1Q but replacing 4-(chloromethyl)-2-isopropylthiazole hydrochloride with 4-(chloromethyl)-2-(dimethylamino)thiazole dihydrochloride provided, after silica gel chromatography using first 10% methanol in chloroform followed by 4% methanol/2% isopropylamine in chloroform, the desired compound, $R_f$ 0.05 (10% methanol in chloroform). $^1$H NMR (CDCl$_3$) $\delta$2.46 (s, 3H), 3.08 (s, 6H), 3.66 (s, 2H), 6.30 (s, 1H). Mass spectrum: (M+H)$^+$=172.

B. N-((N-Methyl-N-(((N,N-dimethylamino)-4-thiazolyl)methyl)amino)carbonyl)-L-valine Methyl Ester A solution of 741 mg (4.42 mmol) of α-isocyanato-L-valine in in 5 ml of dichloromethane was added to a solution of 720 mg (4.21 mmol) of 2-(N,N-dimethylamino)-4-(((N-methyl)amino)methyl)thiazole in 25 ml of dichloromethane. The resulting solution was stirred at ambient temperature for 16 h, partitioned between chloroform and aqueous NaHCO$_3$, dried over Na$_2$SO$_4$, and concentrated in vacuo. The residue was purified by silica gel chromatography using 2% methanol in chloroform to provide 463 mg (34%) of the desired compound, $R_f$ 0.25 (2% methanol in chloroform). NMR (CDCl$_3$) $\delta$0.96 (d, J=7 Hz, 3H), 0.98 (d, J=7 Hz, 3H), 2.13 (m, 1H), 2.97 (s, 3H), 3.11 (s, 6H), 3.71 (s, 3H), 4.07 (br d, J=16 Hz, 1H), 4.34 (dd, J=9, 5 Hz, 1H), 4.42 (d, J=16 Hz, 1H), 6.29 (s, 1H), 6.37 (br, 1H). Mass spectrum: (M+H)$^+$=329.

C. N-((N-Methyl-N-(((N,N-dimethylamino)-4-thiazolyl)methyl)amino)carbonyl)-L-valine Using the procedure of Example 1T, but replacing the resultant compound of Example 1S with the resultant compound of Example 23B provided the desired compound.

D. (2S,3S,5S)-5(N-(N-((N-Methyl-N-(((N,N-dimethylamino)-4-thiazolyl)methyl)amino)carbonyl)valinyl)amino)-2-(N-((5-thiazolyl)methoxycarbonyl)amino)-1,6-diphenyl-3-hydroxyhexane Using the procedure of Example 1U but replacing N-((N-methyl-N-((2-isopropyl-4-thiazolyl)methyl)amino)carbonyl)-L-valine with the resultant compound of Example 23C provided, after silica gel chromatography, the desired compound.

EXAMPLE 24

A. Ethyl 2-Isopropylthiazole-5-carboxylate

Using the procedure of Example 1J but replacing thioformamide with 2-methylpropane-thioamide provided, after silica gel chromatography using 9:1 ethyl acetate:hexane, the desired compound, $R_f$ 0.8, (5% methanol in chloroform) in 83% yield.

B. 5-(Hydroxymethyl)-2-isopropylthiazole

Using the procedure of Example 5B, but replacing ethyl 2-isopropyl-4-thiazolecarboxylate with ethyl 2-isopropylthiazole-5-carboxylate provided, after silica gel chromatography using 3% methanol in chloroform, the desired compound, $R_f$ 0.3, (5% methanol in chloroform) in 25% yield. $^1$H NMR (d$_6$-DMSO) $\delta$1.30 (d, J=7 Hz, 6H), 3.22 (heptet, J=7 Hz, 1H), 4.61 (dd, J=6, 1 Hz, 2H), 5.45 (t, J=6 Hz, 1H), 7.48 (br s, 1H).

C. N-((2-Isopropyl-5-thiazolyl)methoxycarbonyl)valine Methyl Ester

Using the procedure of Example 5D but replacing 4-(hydroxymethyl)-2-isopropylthiazole with 5-(hydroxymethyl)-2-isopropylthiazole provided, after silica gel chromatography using 3% methanol in chloroform, the desired compound, $R_f$ 0.8, (5% methanol in chloroform) in 29% yield. $^1$H NMR $\delta$0.89 (d, J=7 Hz, 6H), 0.95 (d, J=7 Hz, 3H), 0.97 (d, J=7 Hz, 3H), 2.14 (m, 1H), 3.33 (heptet, J=7 Hz, 1H), 3.74 (s, 3H), 4.30 (dd, J=9, 5 Hz, 1H), 5.23 (s, 2H), 5.25 (br d, 1H), 7.63 (s, 1H). Mass spectrum: (M+H)$^+$=315.

D. N-((2-Isopropyl-5-thiazolyl)methoxycarbonyl)valine

Using the procedure of Example 1T, but replacing the resultant compound of Example 1S with the resultant compound of Example 24C provided the desired compound.

E. (2S,3S,5S)-5-(N-(N-((2-Isopropyl-4-thiazolyl)methoxycarbonyl)valinyl)amino)-2-(N-((5-thiazolyl)methoxycarbonyl)amino)-1,6-diphenyl-3-hydroxyhexane Using the procedure of Example 1U but replacing N-((N-methyl-N-((2-isopropyl-4-thiazolyl)methyl)amino)carbonyl)-L-valine with the resultant compound of Example 24D provided the desired compound.

EXAMPLE 25

A. 2-Methoxythioacetamide

Using the procedure of Example 1O but replacing isobutyramide with 2-methoxyacetamide provided the desired compound in 52% yield.

B. 4-(Chloromethyl)-2-(methoxymethyl)thiazole hydrochloride

Using the procedure of Example 1P but replacing 2-methylpropane-thioamide with 2-methoxythioacetamide provided the crude desired compound in 41% yield.

C. 2-(Methoxymethyl)-4-(((N-methyl)amino)methyl)thiazole

Using the procedure of Example 1Q but replacing 4-(chloromethyl)-2-isopropylthiazole hydrochloride with 4-(chloromethyl)-2-(methoxymethyl)thiazole hydrochloride provided, after silica gel chromatography using 3% methanol in chloroform, the desired compound, $R_f$ 0.1, (5% methanol in chloroform) in 73% yield.

D. N-((N-Methyl-N-((2-(methoxymethyl)-4thiazolyl)methyl)amino)carbonyl)-L-valine Methyl Ester Using the procedure of Example 1S but replacing 2-isopropyl-4-(((N-methyl)amino)-methyl)thiazole with 2-(methoxymethyl)-4-(((N-methyl)amino)-methyl)thiazole provided, after silica gel chromatography using 3% methanol in chloroform, the desired Compound, $R_f$ 0.5, (5% methanol in chloroform) in 23% yield.

E. N-((N-Methyl-N-((2-((methoxymethyl-4-thiazolyl)methyl)amino)carbonyl)-L-valine Using the procedure of Example 1 T, but replacing the resultant compound of Example 1S with the resultant compound of Example 25D provided the desired compound.

F. (2S,3S,5S)-5-(N-(N-((N-Methyl-N-((2-(methoxymethyl)-4-thiazolyl)methyl)amino)carbonyl)valinyl)amino)-2-(N-((5-thiazolyl)methoxycarbonyl)amino)-1,6-diphelnyl-3-hydroxyhexane Using the procedure of Example 1U but replacing N-((N-methyl-N-((2-isopropyl-4-thiazolyl)methyl)amino)carbonyl)-L-valine with the resultant compound of Example 25E provided the desired compound.

EXAMPLE 26

A. 1,1-Diethoxy-4-(3,4,5,6-tetrahydro-2H-pyran-2-yl)oxy)-2-butyne

A 1M solution of ethylmagnesium bromide in THF (200 ml, 0.2 mol) was treated with 29 ml (0.2 mol) of a solution of 3,4,5,6-tetrahydro-2-(2-propynyloxy)-2H-pyran in toluene, while maintaining ambient temperature through use of a cool water bath. The resulting solution was stirred for 4 h and treated with 47 ml (0.28 mol) of a solution of triethylorthoformate in toluene, while maintaining ambient temperature with a cool water bath. The resulting solution was heated to 85° C. for 8 h, allowing the removal of THF by distillation. After being allowed to cool, the resulting solution was poured into 500 ml of ice-water containing 29 g of NH$_4$OAc, extracted with two portions of ether, dried over K$_2$CO$_3$, and concentrated in vacuo. The residue was distilled at ca. 0.5 mm Hg pressure (b.p. 103°–108° C.) to provide 39.5 g (79%) of the desired compound. $^1$H NMR (CDCl$_3$) δ1.24 (t, J=7 Hz, 6H), 1.5–1.9 (m, 6H), 3.5–3.65 (m, 3H), 3.7–3.9 (m, 3H), 4.32 (AA', 2H), 4.81 (m, 1H), 5.31 (m, 1H). Mass spectrum: (M+NH$_4$)$^+$=260.

B. 5-(Hydroxymethyl)isoxazole

A solution of 39.28 g (161 mmol) of the resultant compound of Example 26A and 26 g (376 mmol) of hydroxylamine hydrochloride in 168 ml of ethanol and 34 ml of water was heated at reflux under N$_2$ atmosphere for 1 h. After being allowed to cool, the resulting solution was concentrated in vacuo to 1/3 the original volume, diluted with 50 ml of water, and extracted with 2 portions, of ether. The combined extracts were concentrated to an oil. The crude product (7.04 g, 44%) was obtained after distillation (79°–84° C., 0.5 mm Hg). Silica gel chromatography using 0–3% methanol in dichloromethane provided 4.9 g of the desired compound contaminated with 5-hydroxypentanal oxime. $^1$H NMR (CDCl$_3$) δ1.95 (br, 1H), 4.81 (s, 2H), 6.27 (d, J=1 Hz, 1H), 8.23 (d, J=1 Hz, 1H). Mass spectrum: (M+NH$_4$)$^+$=117.

C. ((5-Isoxazolyl)methyl)-(4-nitrophenyl)carbonate

Using the procedure of Example 1L, but replacing 5-(hydroxymethyl)thiazole with 5-(hydroxymethyl)isoxazole provided, after silica gel chromatography using 8:2 dichloromethane:hexane, the desired compound. $^1$H NMR (CDCl$_3$) δ5.41 (s, 2H), 6.46 (d, J=1 Hz, 1H), 7.40 (m, 2H), 8.30 (m, 3H). Mass spectrum: (M+NH4)$^+$=282.

D. (2S,3S,5S)-5-Amino-2-(N-((5-isoxazolyl)methoxycarbonyl)amino)-1,6-diphenyl-3-hydroxyhexane A mixture of 1.54 g (5.41 mmol) of (2S,3S,5S)-2,5-diamino-1,6-diphenyl-3-hydroxyhexane and 0.673 g (5.41 mmol) of phenylboric acid in anhydrous toluene (130 mL) was heated at reflux under argon for 2 hrs with removal of H$_2$O by a Dean-Slark trap. The resulting yellow solution was allowed to cool and the solvent was removed in vacuo to give an oil which solidified upon standing. The residue was taken up in 90 ml of THF, cooled to −40° C., and treated dropwise under Ar atmosphere over a period of 1 h with 1.11 g (3.78 mmol) of ((5-isoxazolyl)methyl)-(4-nitrophenyl)carbonate in 40 ml of THF. The solution was allowed to warm to −20° C. over the next 0.5 hr, then was stirred at 0° C. for 2.5 hrs and at room temperature for 1 hr. After removal of the solvent in vacuo, the residue was taken up in ethyl acetate (200 mL), washed sequentially with 5% aqueous K$_2$CO$_3$ (4×25 mL) and saturated brine (25 mL), dried over Na$_2$So$_4$ and concentrated in vacuo. Silica gel chromatography of the residue using a gradient of methanol in chloroform (2%, 4%, 6%) afforded a mixture of the desired product and its regioisomer. Purification of the mixture on two consecutive 250 g SiO$_2$ columns (deactivated with 1% isopropylamine/CH$_2$Cl$_2$) with a gradient of isopropylamine/CH$_2$Cl$_2$ (0.5%, 1%) afforded the desired compound as a sticky solid (0.730 g, 1.78 mmol, 33%): $^1$H NMR (DMSO-d$_6$) δ1.17–1.57 (m, 5H), 2.56–2.69 (m, 2H), 2.75–2.86 (m, 1H), 2.89–3.00 (m, 2H), 3.53–3.71 (m, 3H), 5.06 (s, 2H), 6.32 (d, J=2.4 Hz, 1H), 7.11–7.30 (m, 10H), 8.54 (d, J=2.4 Hz, 1H). Mass spectrum: (M+H)$^+$=410.

E. (2S,3S,5S)-5-(N-(N-((N-Methyl-N-((2-isopropyl-4-thiazolyl)methyl)amino)carbonyl)valinyl)amino)-2-(N-((5-isoxazolyl)methoxycarbonyl)amino)-1,6-diphenyl-3-hydroxyhexane Using the procedure of Example 1U but replacing (2S,3S,5S)-5-amino-2-(N-((5-thiazolyl)methoxycarbonyl)amino)-1,6-diphenyl-3-hydroxyhexane with (2S,3S,5S)-5-amino-2-(N-((5-isoxazolyl)methoxycarbonyl)amino)-1,6-diphenyl-3-hydroxyhexane provided, after silica gel chromatography using 1% methanol in chloroform, 120 mg (70%) of the desired compound, R$_f$ 0.3, (5% methanol in chloroform), as a solid, mp 60°–62° C. Mass spectrum: (M+H)$^+$=705. Anal. Calcd for C$_{37}$H$_{48}$N$_6$O$_6$S: C, 63.05; H, 6.86; N, 11.92. Found: C, 62.68; H, 7.00; N, 11.65.

EXAMPLE 27

(2S,3S,5S)-5-(N-(N-((N-Methyl-N-((2-isopropyl-4-oxazolyl)methyl)amino)carbonyl)valinyl)amino)-2-(N-((5isoxazolyl)methoxycarbonyl)amino)-1,6-diphenyl-3-hydroxyhexane Using the procedure of Example 1U but replacing (2S,3S,5S)-5-amino-2-(N-((5-thiazolyl)-methoxycarbonyl)amino)-1,6-diphenyl-3-hydroxyhexane with (2S,3S,5S)-5-amino-2-(N-((5-isoxazolyl)methoxycarbonyl)amino)-1,6-diphenyl-3-hydroxyhexane and replacing N-((N-methyl-N-((2-isopropyl-4-thiazolyl)methyl)amino)carbonyl)-L-valine with N-((N-methyl-N-((2-isopropyl-4-oxazolyl)methyl)amino)carbonyl)-L-valine provided, after silica gel chromatography using a gradient of 1–4% methanol in dichloromethane, 225 mg (80%) of the desired compound. $^1$H NMR (DMSO-d$_6$) δ0.74 (d, J=6.9 Hz, 6H), 1.23 (d, J=6.9 Hz, 6H), 1.35–1.54 (m, 2H), 1.80–1.95 (m, 1H), 2.55–2.73

(m, 4H), 2.83 (s, 3H), 2.94–3.09 (m, 1H), 3.53–3.63 (m, 1H), 3.73–3.86 (m, 1H), 3.92 (t, J=8.4 Hz, 1H), 4.08–4.34 (m, 3H), 4.65 (d, J=6 Hz, 1H), 5.04 (s, 2H), 5.91 (d, J=9 Hz, 1H), 6.29 (d, J=2.4 Hz, 1H), 7.01 (d, J=9 Hz, 1H), 7.06–7.27 (m, 10H), 7.69 (d, J=9 Hz, 1H), 7.77 (s, 1H), 8.52 (d, J=2.4 Hz, 1H). Mass spectrum: $(M+H)^+=689$; $(M+NH_4)^+=706$. Anal. Calcd for $C_{37}H_{48}N_6O_7$: C, 64.52; H, 7.02; N, 12.20. Found: C, 64.52; H, 7.14; N, 12.06.

EXAMPLE 28

A. Ethyl 2-Methylthiazole-5-carboxylate

Using the procedure of Example 1J, but replacing thioformamide with thioacetamide provided the crude desired compound.

B. 5-(Hydroxymethyl)-2-methylthiazole

Using the procedure of Example 1K, but replacing ethyl thiazole-5-carboxylate with crude ethyl 2-methylthiazole-5-carboxylate provided, after silica gel chromatography using 3% then 5% methanol in chloroform, the desired compound, $R_f$ 0.27, (4% methanol in chloroform) in 78% yield. $^1$H NMR (CDCl$_3$) $\delta$2.32 (br, 1H), 2.70 (s, 3H), 4.80 (s, 2H), 7.46 (s, 1H). Mass spectrum: $(M+H)^+=130$.

C. ((2-Methyl-5-thiazolyl)methyl)-(4-nitrophenyl)carbonate

Using the procedure of Example 1L, but replacing 5-(hydroxymethyl)thiazole with 5-(hydroxymethyl)-2-methylthiazole provided, after silica gel chromatography using first 1:5 chloroform:hexane, then 4% methanol in chloroform, the desired compound, $R_f$ 0.46 (20% ethyl acetate in chloroform) in 97% yield.

D. (2S,3S,5S)-5-Amino-2-(N-((2-methyl-5-thiazolyl)methoxycarbonyl)amino)-1,6-diphenyl-3-hydroxyhexane and (2S,3S,5S)-2-Amino-5-(N-((2-methyl-5-thiazolyl)methoxycarbonyl)amino)-1,6-diphenyl-3-hydroxyhexane Using the procedure of Example 1M, but replacing ((5-thiazolyl)methyl)-(4-nitrophenyl)carbonate with ((2-methyl-5-thiazolyl)methyl)-(4-nitrophenyl)-carbonate provided, after silica gel chromatography using 4% methanol in chloroform, a mixture of the desired compounds. A second chromatography using 1%–3% isopropylamine in chloroform provided pure (2S,3S,5S)-5-amino-2-(N-((2-methyl-5-thiazolyl)methoxycarbonyl)-amino)-1,6-diphenyl-3-hydroxyhexane and (2S,3S,5S)-2-amino-5-(N-((2-methyl-5-thiazolyl)methoxy-carbonyl)amino)-1,6-diphenyl-3-hydroxyhexane.

E. (2S,3S,5S)-5-(N-(N-((N-Methyl-N-((2-isopropyl-4-thiazolyl)methyl)amino)carbonyl)valinyl)amino)-2-(N-((2-methyl-5-thiazolyl)methoxycarbonyl)amino)-1,6-diphenyl-3-hydroxyhexane Using the procedure of Example 1U but replacing (2S,3S,5S)-5-amino-2-(N-((5-thiazolyl)methoxycarbonyl)amino)-1,6-diphenyl-3-hydroxyhexane with (2S,3S,5S)-5-amino-2-(N-((2-methyl-5-thiazolyl)methoxycarbonyl)amino)-1,6-diphenyl-3-hydroxyhexane provided, after silica gel chromatography using 2% methanol in chloroform, 210 mg (84%) of the desired compound, $R_f$ 0.18, (4% methanol in chloroform). Mass spectrum: $(M+H)^+=735$. Anal. Calcd for $C_{38}H_{50}N_6O_5S_2 \cdot 2H_2O$: C, 59.20; H, 7.06; N, 10.90. Found: C, 58.92; H, 6.37; N, 10.71.

EXAMPLE 29

A. 5-Methyl-1-((3,4,5,6-tetrahydro-2H-pyran-2-yl)oxy)-2-hexyn-4-one

The desired compound was prepared from isobutyryl chloride and 3,4,5,6-tetrahydro-2-(2-propynyloxy)-2H-pyran by analogy to the procedure of Tohda, et. al. (Synthesis, 777 (1977)).

B. 5-(Hydroxymethyl)-3-isopropylisoxazole

Using the procedure of Example 26B but replacing the resultant compound of Example 26A with the resultant compound of Example 29A provided the desired compound.

C. N-((3-Isopropyl-5-isoxazolyl)methoxycarbonyl)valine Methyl Ester

Using the procedure of Example 5D but replacing 4-(hydroxymethyl)-2-isopropylthiazole with 5-(hydroxymethyl)-3-isopropylisoxazole provided the desired compound.

D. N-((3-Isopropyl-5-isoxazolyl)methoxycarbonyl)valine

Using the procedure of Example 1T, but replacing the resultant compound of Example 1S with the resultant compound of Example 29C provided the desired compound.

E. (2S,3S,5S)-5-(N-(N-((3-Isopropyl-5-isoxazolyl)methoxycarbonyl)valinyl)amino)-2-(N-((5-thiazolyl)methoxycarbonyl)amino)-1,6-diphenyl-3-hydroxyhexane Using the procedure of Example 1U but replacing N-((N-methyl-N-((2-isopropyl-4-thiazolyl)methyl)amino)carbonyl)-L-valine with the resultant compound of Example 29D provided the desired compound.

EXAMPLE 30

A. 2-Isopropyl-4-(methanesulfonyloxymethyl)thiazole

A solution of 1.2 mmol of 4-(hydroxymethyl)-2-isopropylthiazole and 1.3 mmol of diisopropylethylamine in 20 ml of dichloromethane was cooled to $-20°$ C. and treated dropwise with 1.3 mmol of methanesulfonyl chloride. The resulting mixture was stirred for 1 h, quenched with aqueous citric acid, separated, dried over $Na_2SO_4$, and concentrated in vacuo to provide the desired compound.

B. 2-Isopropyl-4-(mercaptomethyl)thiazole

A mixture of 0.8 mmol of the resultant compound of Example 30A and 1.0 mmol of sodium hydrosulfide hydrate in 20 ml of THF was heated at reflux until analysis by thin layer chromatography indicated consumption of starting material. The resulting mixture was allowed to cool, concentrated in vacuo, partitioned between dichloromethane and water, dried over $Na_2SO_4$, and concentrated to provide the crude desired compound.

C. N-((2-Isopropyl-4-thiazolyl)methoxycarbonyl)valine Methyl Ester

Using the procedure of Example 5D, but replacing 4-(hydroxymethyl)-2-isopropylthiazole with the resultant compound of Example 30B provided, after chromatography on silica gel, the desired compound.

D. N-((2-Isopropyl-4-thiazolyl)thiomethoxycarbonyl)valine

Using the procedure of Example 1T, but replacing the resultant compound of Example 1S with the resultant compound of Example 30C provided the desired compound.

E. (2S,3S,5S)-5-(N-(N-((2-Isopropyl-4-thiazolyl)thiomethoxycarbonyl)valinyl)amino)-2-(N-((5-thiazolyl)methoxycarbonyl)amino)-1,6-diphenyl-3-hydroxyhexane Using the procedure of Example 1U but replacing N-((N-methyl-N-((2-isopropyl-4-thiazolyl)methyl)amino)carbonyl)-L-valine with the resultant compound of Example 30D provided, after purification by silica gel chromatography, the desired compound.

EXAMPLE 31

A. 2-Isopropylthiazole-4-carboxaldehyde

A solution of 3.1 g (15.6 mmol) of ethyl 2-isopropylthiazole-4-carboxylate in 50 ml of dichloromethane was cooled under $N_2$ atmosphere to −78° C. and treated dropwise with 15.6 ml (23.4 mmol) of a 1.5M solution of diisobutylaluminum hydride in toluene over a period of 1.5 h. After being stirred for an additional 0.5 h, the solution was quenched with 5 ml of methanol followed by 15 ml of aqueous Rochelle's salt. The resulting mixture was partitioned between chloroform and aqueous Rochelle's salt, dried over $Na_2SO_4$, and concentrated to provide 1.37 g (56%) of the crude desired compound, $R_f$ 0.47 (20% ethyl acetate in hexane). $^1$H NMR (CDCl$_3$) δ1.45 (d, J=7 Hz, 6H), 3.39 (heptet, J=7 Hz, 1H), 8.07 (s, 1H), 10.00 (s, 1H). Mass spectrum: (M+H)$^+$=156.

B. (E)-Ethyl-3-(2-Isopropyl-4-thiazolyl)propenoate

A slurry of 60% NaH (18 mmol) in mineral oil was washed with hexane, decante under $N_2$ atmosphere, and diluted with 25 ml of THF. The resulting mixture was cooled to 0° C., treated portionwise with 3.24 ml (16.4 mmol) of triethylphosphonoacetate. After addition, the solution was stirred for 10 min, treated with 1.37 g (8.84 mmol) of 2-isopropylthiazole-4-carboxaldehyde in 25 ml of THF, allowed to warm to ambient temperature for 25 min, and quenched with 100 ml of saturated aqueous NH$_4$Cl. The mixture was extracted with three 100 ml portions of ethyl acetate, dried over $Na_2SO_4$, and concentrated in vacuo. Silica gel chromatography of the residue using 5–10% ethyl acetate in hexane provided 1.61 g (81%) of the desired compound, $R_f$ 0.64 (20% ethyl acetate in hexane). $^1$H NMR (CDCl$_3$) δ1.33 (t, J=7 Hz, 3H), 1.42 (d, J=7 Hz, 6H), 3.32 (heptet, J=7 Hz, 1H), 4.26 (q, J=7 Hz, 2H), 6.75 (d, J=15 Hz, 1H), 7.29 (s, 1H), 7.57 (d, J=15 Hz, 1H).

C. Methyl 3-(2-Isopropyl-4-thiazolyl)propanoate

A solution of 225 mg (1 mmol) of (E)-ethyl 3-(2-isopropyl-4-thiazolyl)propenoate in 10 ml of freshly distilled (from calcium hydride) methanol and 1 ml of dry THF was treated with 49 mg (2 mmol) of magnesium turnings. The mixture was stirred for 20 min, during which the magnesium was consumed. The resulting solution was poured over cold aqueous HCl, basified to pH 8 with NaHCO$_3$, extracted with ethyl acetate, dried over $Na_2SO_4$, and concentrated. Silica gel chromatography using 10% ethyl acetate in hexane provided a mixture of the desired compound and methyl 3-(2-isopropyl-4-thiazolinyl)propanoate.

D. 3-(2-Isopropyl-4-thiazolyl)propanoic Acid

Using the procedure of Example 1T, but replacing the resultant compound of Example 1S with the resultant compound of Example 31C provided the desired compound.

E. (2S,3S,5S)-5-(N-(N-(tert-Butyloxycarbonyl)valinyl)amino)-2-(N-((5-thiazolyl)methoxycarbonyl)amino)-1,6-diphenyl-3-hydroxyhexane Using the procedure of Example 1U but replacing N-((N-methyl-N-((2- isopropyl-4-thiazolyl)methyl)amino)carbonyl)-L-valine with N-(tert-butyloxycarbonyl)-L-valine provided, after purification by silica gel chromatography, the desired compound.

F. (2S,3S,5S)-5-(N-(Valinyl)amino)-2-(N-((5-thiazolyl)methoxycarbonyl)amino)-1,6-diphenyl-3-hydroxyhexane A solution of 0.1 mmol of the resultant compound of Example 31E was treated with 10 ml of 4N HCl in dioxane, stirred at 0° C. for 1 h, concentrated in vacuo, partitioned between chloroform and aqueous NaHCO$_3$, dried over $Na_2SO_4$, and concentrated to provide the crude desired compound.

G. (2S,3S,5S)-5-(N-(N-(3-(2-Isopropyl-4-thiazolyl)propanoyl)valinyl)amino-2-(N-((5-thiazolyl)methoxycarbonyl)amino)-1,6-diphenyl-3-hydroxyhexane Using the procedure of Example 1U but replacing N-((N-methyl-N-((2-isopropyl-4-thiazolyl)methyl)amino)carbonyl)-L-valine with the resultant compound of Example 31D and replacing (2S,3S,5S)-5-amino-2-(N-((5-thiazolyl)methoxycarbonyl)amino)-1,6-diphenyl-3-hydroxyhexane with the resultant compound of Example 31F provided, after purification by silica gel chromatography, the desired compound.

EXAMPLE 32

A. Thiazole-5-carboxaldehyde

Using the procedure of Example 16A but replacing ethyl 2-isopropyl-4-thiazole carboxylate with ethyl thiazole-5-carboxylate provided the desired compound.

B. 5-(1-Hydroxyethyl)thiazole

Using the procedure of Example 16B but replacing the resultant compound of Example 16A with the resultant compound of Example 32A provided the desired compound.

C. (1-(5-Thiazolyl)ethyl)-(4-nitrophenyl)carbonate

Using the procedure of Example 1L but replacing 5-(hydroxymethyl)thiazole with the resultant compound of Example 32B provided the desired compound.

D. (2S,3S,5S)-5-Amino-2-(N-(1-(5-thiaz-olyl)ethoxycarbonyl)amino)-1,6-diphenyl-3-hydroxyhexane Using the procedure of Example 19F but replacing ((5-oxazolyl)methyl)-(4-nitrophenyl)carbonate with (1-(5-thiazolyl)ethyl)-(4-nitrophenyl)carbonate provided, after purification by silica gel chromatography, the desired compound.

E. (2S,3S,5S)-5-(N-(N-((N-Methyl-N-((2-isopropyl-4-thiazolyl)methyl)amino)carbonyl)valinyl)amino)-2-(N-(1-(5-thiazolyl)ethoxycarbonyl)amino)-1,6-diphenyl-3-hydroxyhexane Using the procedure of Example 1U but replacing (2S,3S,5S)-5-amino-2-(N-((5-thiazolyl)methoxycarbonyl)amino)-1,6-diphenyl-3-hydroxyhexane with the resultant compound of Example 32D provided, after purification by silica gel chromatography, the desired compound.

EXAMPLE 33

A. ((5-Isothiazolyl)methyl)-(4-nitrophenyl)carbonate

Using the procedure of Example 1L but replacing 5-(hydroxymethyl)thiazole with 5-(hydroxymethyl)isothiazole (Bennett, et. al., *J. Chem. Soc.*, 3834 (1965)) provided the desired compound.

B. (2S,3S,5S)-5-Amino-2-(N-((5-isothiazolyl)methoxycarbonyl)amino)-1,6-diphenyl-3-hydroxyhexane Using the procedure of Example 19F but replacing ((5-oxazolyl)methyl)-(4-nitrophenyl)carbonate with ((5-isothiazolyl)methyl)-(4-nitrophenyl)carbonate provided, after purification by silica gel chromatography, the desired compound.

C. (2S,3S,5S)-5-(N-(N-((N-Methyl-N-((2-isopropyl-4-thiazolyl)methyl)amino)carbonyl)valinyl)amino)-2-(N-((5-isothiazolyl)methoxycarbonyl)amino)-1,6-diphenyl-3-hydroxyhexane Using the procedure of Example 1U but replacing (2S,3S,5S)-5-amino-2-(N-((5-thiazolyl)methoxycarbonyl)amino)-1,6-diphenyl-3-hydroxyhexane with the resultant compound of Example 33B provided, after purification by silica gel chromatography, the desired compound.

EXAMPLE 34

A. (2S,3R,4R,5S)-2,5-Diamino-3,4-dihydroxy-1,6-diphenylhexane

Using the procedure of Example 1F but replacing the resultant compound of Example 1E with (2S,3R,4R,5S)-2,5-bis-(N-(((benzyl)oxy)carbonyl)amino)-3,4-dihydroxy-1,6-diphenylhexane provided the crude desired compound mixed with benzyl alcohol in 92% yield. Purification of a sample was achieved by silica gel chromatography using 2% isopropylamine in chloroform. $^1$H NMR (CDCl$_3$) δ2.71 (dd, J=13, 9 Hz, 2H), 2.92 (dd, J=13, 5 Hz, 2H), 3.03 (dd, J=9, 5 Hz, 2H), 3.68 (s, 2H), 7.15–7.35 (m, 10H). Mass spectrum: (M+H)$^+$=301.

B. (2S,3R,4R,5S)-2-Amino-5-(N-((5-thiazolyl)methoxy(carbonyl)amino)-3,4-dihydroxy-1,6-diphenylhexane Using the procedure of Example 1M but replacing (2S,3S,5S)-2,5-diamino-1,6-diphenyl-3-hydroxyhexane with (2S,3R,4R,5S)-2,5-diamino-3,4-dihydroxy-1,6-diphenylhexane provided, after silica gel chromatography, the desired compound.

C. (2S,3R,4R,5S)-5-(N-(N-((N-Methyl-N-((2-isoprOpyl-4-thiazolyl)methyl)amino)carbonyl)valinyl)amino)-2-(N-((5-thiazolyl)methoxycarbonyl)amino)-3,4-dihydroxy-1,6-diphenylhexane Using the procedure of Example 1U but replacing (2S,3S,5S)-5-amino-2-(N-((5-thiazolyl)methoxycarbonyl)amino)-1,6-diphenyl-3-hydroxyhexane with the resultant compound of Example 34B provided, after purification by silica gel chromatography, the desired compound.

EXAMPLE 35

A. (2S,3S,4S,5S)-2,5-Diamino-3,4-dihydroxy-1,6-diphenylhexane

Using the procedure of Example 1F but replacing the resultant compound of Example 1E with (2S,3S,4S,5S)-2,5-bis-(N-(((benzyl)oxy)carbonyl)amino)-3,4-dihydroxy-1,6-diphenylhexane provided the desired compound. $^1$H NMR (CDCl$_3$) δ2.63 (dd, J=14, 11 Hz, 2H), 2.85 (dd, J=14, 4 Hz, 2H), 3.60 (dt, J=11,4 Hz, 2H), 3.92 (d, J=3 Hz, 2H), 7.2–7.4 (m, 10H). Mass spectrum: (M+H)$^+$=301.

B. (2S,3S,4S,5S)-2-Amino-5-(N-((5-thiazolyl)methoxycarbonyl)amino)-3,4-dihydroxy-1,6-diphenylhexane Using the procedure of Example 1M but replacing (2S,3S,5S)-2,5-diamino-1,6-diphenyl-3-hydroxyhexane with (2S,3S,4S,5S)-2,5-diamino-3,4-dihydroxy-1,6-diphenylhexane provided, after silica gel chromatography, the desired compound.

C. (2S,3S,4S,5S)-5(N-(N-((N-Methyl-N-((2-isopropyl-4-thiazolyl)methyl)amino)carbonyl)valinyl)amino)-2-(N-((5-thiazolyl)methoxycarbonyl)amino)-3,4-dihydroxy-1,6-diphenylhexane Using the procedure of Example 1U but replacing (2S,3S,5S)-5-amino-2-(N-((5-thiazolyl)methoxycarbonyl)amino)-1,6-diphenyl-3-hydroxyhexane with the resultant compound of Example 35B provided, after purification by silica gel chromatography, the desired compound.

EXAMPLE 36

A. (4S,5S,1'R,2'S)-5-(1-Acetoxy-2-(N-((((benzyl)oxy)carbonyl)amino))-3-phenylpropyl)-4-benzyl-oxazolidin-2-one A suspension of 5.02 g (8.80 mmol) of (2S,3R,4R,5S)-2,5-bis-(N-(((benzyl)oxy)carbonyl)amino)-3,4-dihydroxy-1,6-diphenylhexane in 400 ml of acetonitrile was treated dropwise with 3 ml (20 mmol) of acetoxyisobutyryl bromide. The resulting solution was stirred under N$_2$ atmosphere at ambient temperature for 2 h, filtered to remove traces of solid starting material, quenched cautiously with 100 ml of aqueous NaHCO$_3$, and concentrated in vacuo to a volume of 100 ml. The resulting mixture was extracted with two 100 ml portions of dichloromethane, dried over Na$_2$SO$_4$, and concentrated in vacuo. The residue was purified by silica gel chromatography using first 10% then 25% ethyl acetate in dichloromethane to provide 3.15 g (71%) of the desired compound as a white foam. $^1$H NMR (CDCl$_3$) δ2.09 (s, 3H), 2.53 (br t, J=12 Hz, 1H), 2.72 (dd, J=13, 3 Hz, 1H), 2.83 (dd, J=14, 8 Hz, 1H), 2.95 (dd, J=14, 7 Hz, 1H), 3.95 (m, 1H), 4.45 (m, 1H), 4.8 (m, 2H), 5.0–5.1 (m, 3H), 5.29 (dd, J=9, 3 Hz, 1H), 7.0–7.4 (m, 10H). Mass spectrum: (M+NH$_4$)$^+$=520.

B. (2S,3R,4S,5S)-2,5-Diamino-3,4-dihydroxy-1,6-diphenylhexane

Using the procedure of Example 1F but replacing the resultant compound of Example 1E with (4S,5S,1'R,2'S)-5-(1-acetoxy-2-(N-(benzyloxycarbonylamino))-3-phenylpropyl)-4-benzyl-oxazolidin-2-one provided the desired compound mixed with benzyl alcohol. Purification of a small portion by silica gel chromatography using 5% methanol/2% isopropylamine in chloroform provided the pure desired compound., m.p. 115°–119° C. $^1$H NMR (CDCl$_3$) δ2.46 (dd, J=14, 9 Hz, 1H), 2.61 (dd, J=14, 11 Hz, 1H), 3.02 (td, J=9, 3 Hz, 1H), 3.19 (dd, J=14, 4 Hz, 1H), 3.35–3.4 (m, 2H), 3.51 (t, J=9 Hz, 1H), 3.76 (dd, J=9, 3 Hz, 1H), 7.2–7.4 (m, 10H).

C. (2S,3R,4S,5S)-5-Amino-2-(N-((5-thiazolyl)methoxycarbonyl)amino)-3,4-dihydroxy-1,6-diphenylhexane A solution of 0.133 mmol of (2S,3R,4S,5S)-2,5-diamino-3,4-dihydroxy-1,6-diphenylhexane and 0.147 mmol of ((5-thiazolyl)methyl)-(4-nitrophenyl)-carbonate in 10 ml of tetrahydrofuran was stirred at ambient temperature for 16 h. The resulting solution was diluted with 50 ml of chloroform, washed with several portions of 3N aqueous NaOH, dried over Na$_2$SO$_4$, and concentrated in vacuo. Silica gel chromatography of the residue provided the desired compound.

D. (2S,3R,4S,5S)-5-(N-(N-((N-Methyl-N-((2-isopropyl-4-thiazolyl)methyl)amino)carbonyl)valinyl)amino)-2-(N-((5-thiazolyl)methoxycarbonyl)amino)-3,4-dihydroxy-1,6-diphenylhexane Using the procedure of Example 1U but replacing (2S,3S,5S)-5-amino-2-(N-((5-thiazolyl)methoxycarbonyl)amino)-1,6-diphenyl-3-hydroxyhexane with the resultant compound of Example 36C provided, after purification by silica gel chromatography, the desired compound.

EXAMPLE 37

A. (2S,3R,4S,5S)-2-Amino-5-(N-((5-thiazolyl)methoxycarbonyl)amino)-3,4-dihydroxy-1,6-diphenylhexane Using the procedure of Example 1U but replacing (2S,3S,5S)-5-amino-2-(N-((5-thiazolyl)methoxycarbonyl)amino)-1,6-diphenyl-3-hydroxyhexane with (2S,3R,4S,5S)-2,5-diamino-3,4-dihydroxy-1,6-diphenylhexane provided, after purification by silica gel chromatography, the desired compound.

B. (2S,3R,4S,5S)-2(N-(N-((N-Methyl-N-((2-isopropyl-4-thiazolyl)methyl)amino)carbonyl)valinyl)amino)-5-(N-((5-thiazolyl)methoxycarbonyl)amino)-3,4-dihydroxy-1,6-diphenylhexane Using the procedure of Example 36C but replacing (2S,3R,4S,5S)-2,5-diamino-3,4-dihydroxy-1,6-diphenylhexane with the resultant compound of Example 37A provided, after purification by silica gel chromatography, the desired compound.

EXAMPLE 38

A. 5-(Hydroxymethyl)-3-isopropylisothiazole

The desired compound was prepared from the resultant compound of Example 29A using the procedure of Lucchesini, et. al. (Heterocycles, 29, 97 (1989)).

B. N-((3-Isopropyl-5-isothiazolyl)methoxycarbonyl)valine Methyl Ester

Using the procedure of Example 5D but replacing 4-(hydroxymethyl)-2-isopropylthiazole with 5-(hydroxymethyl)-3-isopropylisothiazole provided the desired compound.

C. N-((3-Isopropyl-5-isothiazolyl)methoxycarbonyl)valine

Using the procedure of Example 1T, but replacing the resultant compound of Example 1S with the resultant compound of Example 38B provided the desired compound.

D. (2S,3S,5S)-5-(N-(N-((3-Isopropyl-5-isothiazolyl)methoxycarbonyl)valinyl)amino)-2-(N-((5-thiazolyl)methoxycarbonyl)amino)-1,6-diphenyl-3-hydroxyhexane Using the procedure of Example 1U but replacing N-((N-methyl-N-((2-isopropyl-4-thiazolyl)methyl)amino)carbonyl)-L-valine with the resultant compound of Example 38C provided the desired compound.

EXAMPLE 39

(2S,3S,5S)-2-(N-(N-((N-Methyl-N-((2-isopropyl-4-thiazolyl)methyl)amino)carbonyl)valinyl)amino)-5-(N-((2-methyl-5-thiazolyl)methoxycarbonyl)amino)-1,6-diphenyl-3-hydroxyhexane Using the procedure of Example 1U but replacing (2S,3S,5S)-5-amino-2-(N-((5-thiazolyl)methoxycarbonyl)amino)-1,6-diphenyl-3-hydroxyhexane with (2S,3S,5S)-2-amino-5-(N-((2-methyl-5-thiazolyl)methoxycarbonyl)amino)-1,6-diphenyl-3-hydroxyhexane provided, after silica gel chromatography using 2% methanol in chloroform, 20 mg (80%) of the desired compound, R$_f$ 0.23, (4% methanol in chloroform). Mass spectrum: (M+H)$^+$=735. Anal. Calcd for C$_{38}$H$_{50}$N$_6$O$_5$S$_2$.2H$_2$O: C, 59.20; H, 7.06; N, 10.90. Found: C, 59.13; H, 6.42; N, 10.82.

EXAMPLE 40

Following the procedures of the above Examples, the following compounds can be prepared.

(2S,3R,4S,5S)-5-(N-(N-((N-Methyl-N-((2-isopropyl-4-thiazolyl)methyl)amino)carbonyl)alaninyl)amino)-2-(N-((5-thiazolyl)methoxycarbonyl)amino)-3,4-dihydroxy-1,6-diphenylhexane.

(2S,3R,4S,5S)-5-(N-(N-((2-Isopropyl-4-thiazolyl)methoxycarbonyl)valinyl)amino)-2-(N-((5-thiazolyl)methoxycarbonyl)amino)-3,4-dihydroxy-1,6-diphenylhexane.

(2S,3R,4S,5S)-5-(N-(N-((2-Isopropyl-4-thiazolyl)methoxycarbonyl)alaninyl)amino)-2-(N-((5-thiazolyl)methoxycarbonyl)amino)-3,4-dihydroxy-1,6-diphenylhexane.

(2S,3R,4S,5S)-5-(N-(N-((2-(1-Pyrrolidinyl)-4-thiazolyl)methoxycarbonyl)valinyl)amino)-2-(N-((5-thiazolyl)methoxycarbonyl)amino)-3,4-dihydroxy-1,6-diphenylhexane.
(2S,3R,4S,5S)-5-(N-(N-((N-Methyl-N-((2-isopropyl-4-oxazolyl)methyl)amino)carbonyl)valinyl)amino)-2-(N-((5-thiazolyl)methoxycarbonyl)amino)-3,4-dihydroxy-1,6-diphenylhexane.
(2S,3R,4S,5S)-5-(N-(N-((N-Methyl-N-((2-isopropyl-4-oxazolyl)methyl)amino)carbonyl)valinyl)amino)-2-(N-((5-oxazolyl)methoxycarbonyl)amino)-3,4-dihydroxy-1,6-diphenylhexane.
(2S,3R,4S,5S)-5-(N-(N-((N-Methyl-N-((2-isopropyl-4-thiazolyl)methyl)amino)carbonyl)valinyl)amino)-2-(N-((5-oxazolyl)methoxycarbonyl)amino)-3,4-dihydroxy-1,6-diphenylhexane.
(2S,3R,4S,5S)-5-(N-(N-((N-Methyl-N-((2-isopropyl-4-thiazolyl)methyl)amino)carbonyl)valinyl)amino)-2-(N-((5-isoxazolyl)methoxycarbonyl)amino)-3,4-dihydroxy-1,6-diphenylhexane.
(2S,3R,4S,5S)-5-(N-(N-((N-Methyl-N-((2-isopropyl-4-oxazolyl)methyl)amino)carbonyl)valinyl)amino)-2-(N-((5-isoxazolyl)methoxycarbonyl)amino)-3,4-dihydroxy-1,6-diphenylhexane.
(2S,3R,4S,5S)-5-(N-(N-((N-Methyl-N-((2-isopropyl-4-thiazolyl)methyl)amino)carbonyl)valinyl)amino)-2-(N-((5-isothiazolyl)methoxycarbonyl)amino)-3,4-dihydroxy-1,6-diphenylhexane.
(2S,3R,4S,5S)-2-(N-(N-((N-Methyl-N-((2-isopropyl-4-thiazolyl)methyl)amino)carbonyl)alaninyl)amino)-5-(N-((5-thiazolyl)methoxycarbonyl)amino)-3,4-dihydroxy-1,6-diphenylhexane.
(2S,3R,4S,5S)-2-(N-(N-((2-Isopropyl-4-thiazolyl)methoxycarbonyl)valinyl)amino)-5-(N-((5-thiazolyl)methoxycarbonyl)amino)-3,4-dihydroxy-1,6-diphenylhexane.
(2S,3R,4S,5S)-2-(N-(N-((2-Isopropyl-4-thiazolyl)methoxycarbonyl)alaninyl)amino)-5-(N-((5-thiazolyl)methoxycarbonyl)amino)-3,4-dihydroxy-1,6-diphenylhexane.
(2S,3R,4S,5S)-2-(N-(N-((2-(1-Pyrrolidinyl)-4-thiazolyl)methoxycarbonyl)valinyl)amino)-5-(N-((5-thiazolyl)methoxycarbonyl)amino)-3,4-dihydroxy-1,6-diphenylhexane.
(2S,3R,4S,5S)-2-(N-(N-((N-Methyl-N-((2-isopropyl-4-oxazolyl)methyl)amino)carbonyl)valinyl)amino)-5-(N-((5-thiazolyl)methoxycarbonyl)amino)-3,4-dihydroxy-1,6-diphenylhexane.
(2S,3R,4S,5S)-2-(N-(N-((N-Methyl-N-((2-isopropyl-4-oxazolyl)methyl)amino)carbonyl)valinyl)amino)-5-(N-((5-oxazolyl)methoxycarbonyl)amino)-3,4-dihydroxy-1,6-diphenylhexane.
(2S,3R,4S,5S)-2-(N-(N-((N-Methyl-N-((2-isopropyl-4-thiazolyl)methyl)amino)carbonyl)valinyl)amino)-5-(N-((5-oxazolyl)methoxycarbonyl)amino)-3,4-dihydroxy-1,6-diphenylhexane.
(2S,3R,4S,5S)-2-(N-(N-((N-Methyl-N-((2-isopropyl-4-thiazolyl)methyl)amino)carbonyl)valinyl)amino)-5-(N-((5-isoxazolyl)methoxycarbonyl)amino)-3,4-dihydroxy-1,6-diphenylhexane.
(2S,3R,4S,5S)-2-(N-(N-((N-Methyl-N-((2-isopropyl-4-oxazolyl)methyl)amino)carbonyl)valinyl)amino)-5-(N-((5-isoxazolyl)methoxycarbonyl)amino)-3,4-dihydroxy-1,6-diphenylhexane.
(2S,3R,4S,5S)-2-(N-(N-((N-Methyl-N-((2-isopropyl-4-thiazolyl)methyl)amino)carbonyl)valinyl)amino)-5-(N-((5-isothiazolyl)methoxycarbonyl)amino)-3,4-dihydroxy-1,6-diphenylhexane.
(2S,3R,4R,5S)-5-(N-(N-((N-Methyl-N-((2-isopropyl-4-thiazolyl)methyl)amino)carbonyl)alaninyl)amino)-2-(N-((5-thiazolyl)methoxycarbonyl)amino)-3,4-dihydroxy-1,6-diphenylhexane.
(2S,3R,4R,5S)-5-(N-(N-((2-Isopropyl-4-thiazolyl)methoxycarbonyl)valinyl)amino)-2-(N-((5-thiazolyl)methoxycarbonyl)amino)-3,4-dihydroxy-1,6-diphenylhexane.
(2S,3R,4R,5S)-5-(N-(N-((2-Isopropyl-4-thiazolyl)methoxycarbonyl)alaninyl)amino)-2-(N-((5-thiazolyl)methoxycarbonyl)amino)-3,4-dihydroxy-1,6-diphenylhexane.
(2S,3R,4R,5S)-5-(N-(N-((2-(1-Pyrrolidinyl)-4-thiazolyl)methoxycarbonyl)valinyl)amino)-2-(N-((5thiazolyl)methoxycarbonyl)amino)-3,4-dihydroxy-1,6-diphenylhexane.
(2S,3R,4R,5S)-5-(N-(N-((N-Methyl-N-((2-isopropyl-4-oxazolyl)methyl)amino)carbonyl)valinyl)amino)-2-(N-((5-thiazolyl)methoxycarbonyl)amino)-3,4-dihydroxy-1,6-diphenylhexane.
(2S,3R,4R,5S)-5-(N-(N-((N-Methyl-N-((2-isopropyl-4-oxazolyl)methyl)amino)carbonyl)valinyl)amino)-2-(N-((5-oxazolyl)methoxycarbonyl)amino)-3,4-dihydroxy-1,6-diphenylhexane.
(2S,3R,4R,5S)-5-(N-(N-((N-Methyl-N-((2-isopropyl-4-thiazolyl)methyl)amino)carbonyl)valinyl)amino)-2-(N-((5-oxazolyl)methoxycarbonyl)amino)-3,4-dihydroxy-1,6-diphenylhexane.
(2S,3R,4R,5S)-5-(N-(N-((N-Methyl-N-((2-isopropyl-4-thiazolyl)methyl)amino)carbonyl)valinyl)amino)-2-(N-((5-isoxazolyl)methoxycarbonyl)amino)-3,4-dihydroxy-1,6-diphenylhexane.
(2S,3R,4R,5S)-5-(N-(N-((N-Methyl-N-((2-isopropyl-4-oxazolyl)methyl)amino)carbonyl)valinyl)amino)-2-(N-((5-isoxazolyl)methoxycarbonyl)amino)-3,4-dihydroxy-1,6-diphenylhexane.
(2S,3R,4R,5S)-5-(N-(N-((N-Methyl-N-((2-isopropyl-4-thiazolyl)methyl)amino)carbonyl)valinyl)amino)-2-(N-((5-isothiazolyl)methoxycarbonyl)amino)-3,4-dihydroxy-1,6-diphenylhexane.
(2S,3S,4S,5S)-5-(N-(N-((N-Methyl-N-((2-isopropyl-4-thiazolyl)methyl)amino)carbonyl)alaninyl)amino)-2-(N-((5-thiazolyl)methoxycarbonyl)amino)-3,4-dihydroxy-1,6-diphenylhexane.
(2S,3S,4S,5S)-5-(N-(N-((2-Isopropyl-4-thiazolyl)methoxycarbonyl)valinyl)amino)-2-(N-((5-thiazolyl)methoxycarbonyl)amino)-3,4-dihydroxy-1,6-diphenylhexane.
(2S,3S,4S,5S)-5-(N-(N-((2-Isopropyl-4-thiazolyl)methoxycarbonyl)alaninyl)amino)-2-(N-((5-thiazolyl)methoxycarbonyl)amino)-3,4-dihydroxy-1,6-diphenylhexane.
(2S,3S,4S,5S)-5-(N-(N-((2-(1-Pyrrolidinyl)-4-thiazolyl)methoxycarbonyl)valinyl)amino)-2-(N-((5-thiazolyl)methoxycarbonyl)amino)-3,4-dihydroxy-1,6-diphenylhexane.
(2S,3S,4S,5S)-5-(N-(N-((N-Methyl-N-((2-isopropyl-4-oxazolyl)methyl)amino)carbonyl)valinyl)amino)-2-(N-((5-thiazolyl)methoxycarbonyl)amino)-3,4-dihydroxy-1,6-diphenylhexane.
(2S,3S,4S,5S)-5-(N-(N-((N-Methyl-N-((2-isopropyl-4-oxazolyl)methyl)amino)carbonyl)valinyl)amino)-2-(N-((5-oxazolyl)methoxycarbonyl)amino)-3,4-dihydroxy-1,6-diphenylhexane.
(2S,3S,4S,5S)-5-(N-(N-((N-Methyl-N-((2-isopropyl-4-thiazolyl)methyl)amino)carbonyl)valinyl)amino)-2-(N-((5-oxazolyl)methoxycarbonyl)amino)-3,4-dihydroxy-1,6-diphenylhexane.
(2S,3S,4S,5S)-5-(N-(N-((N-Methyl-N-((2-isopropyl-4-thiazolyl)methyl)amino)carbonyl)valinyl)amino)-2-(N-((5-isoxazolyl)methoxycarbonyl)amino)-3,4-dihydroxy-1,6-diphenylhexane.
(2S,3S,4S,5S)-5-(N-(N-((N-Methyl-N-((2-isopropyl-4-oxazolyl)methyl)amino)carbonyl)valinyl)amino)-2-(N-((5-isoxazolyl)methoxycarbonyl)amino)-3,4-dihydroxy-1,6-diphenylhexane.

(2S,3S,4S,5S)-5-(N-(N-((N-Methyl-N-((2-isopropyl-4-thiazolyl)methyl)amino)carbonyl)valinyl)amino)-2-(N-((5-isothiazolyl)methoxycarbonyl)amino)-3,4-dihydroxy-1,6-diphenylhexane.

(2S,3S,5S)-5-(N-(N-((N-Methyl-N-((2-cyclopentyl-4-thiazolyl)methyl)amino)carbonyl)valinyl)amino)-2-(N-((5-oxazolyl)methoxycarbonyl)amino)-1,6-diphenyl-3-hydroxyhexane.

(2S,3S,5S)-5-(N-(N-((N-Methyl-N-((2-cyclohexyl-4-thiazolyl)methyl)amino)carbonyl)valinyl)amino)-2-(N-((5-oxazolyl)methoxycarbonyl)amino)-1,6-diphenyl-3-hydroxyhexane.

(2S,3S,5S)-5-(N-(N-((N-Methyl-N-((2-(1,1-dimethyl)ethyl-4-thiazolyl)methyl)amino)carbonyl)-2-(N-((5-oxazolyl)methoxycarbonyl)amino)-1,6-diphenyl-3-hydroxyhexane.

(2S,3S,5S)-5-(N-(N-((N-Methyl-N-((2-cyclobutyl-4-thiazolyl)methyl)amino)carbonyl)valinyl)amino)-2-(N-((5-oxazolyl)methoxycarbonyl)amino)-1,6-diphenyl-3-hydroxyhexane.

(2S,3S,5S)-5-(N-(N-((N-Methyl-N-((2-cyclopropyl-4-thiazolyl)methyl)amino)carbonyl)valinyl)amino)-2-(N-((5-oxazolyl)methoxycarbonyl)amino)-1,6-diphenyl-3-hydroxyhexane.

(2S,3S,5S)-5-(N-(N-((N-Methyl-N-((2-ethyl-4-thiazolyl)methyl)amino)carbonyl)valinyl)amino)-2-(N-((5-oxazolyl)methoxycarbonyl)amino)-1,6-diphenyl-3-hydroxyhexane.

(2S,3S,5S)-5-(N-(N-((N-Methyl-N-((2-ethenyl-4-thiazolyl)methyl)amino)carbonyl)valinyl)amino)-2-(N-((5-oxazolyl)methoxycarbonyl)amino)-1,6-diphenyl-3-hydroxyhexane.

(2S,3S,5S)-5-(N-(N-((N-Methyl-N-((2-(2-propenyl)-4-thiazolyl)methyl)amino)-carbonyl)valinyl)amino)-2-(N-((5-oxazolyl)methoxycarbonyl)amino)-1,6-diphenyl-3-hydroxyhexane.

(2S,3S,5S)-5-(N-(N-((N-Methyl-N-((2-(1-cyclopentenyl)-4-thiazolyl)methyl)amino)carbonyl)valinyl)amino)-2-(N-((5-oxazolyl)methoxycarbonyl)amino)-1,6-diphenyl-3-hydroxyhexane.

(2S,3S,5S)-5-(N-(N-((N-Methyl-N-((2-(1-cyclohexenyl)-4-thiazolyl)methyl)amino)carbonyl)valinyl)amino)-2-(N-((5-oxazolyl)methoxycarbonyl)amino)-1,6-diphenyl-3-hydroxyhexane.

(2S,3S,5S)-5-(N-(N-((N-Methyl-N-((4-cyclopentenyl-4-thiazolyl)methyl)amino)-carbonyl)valinyl)amino)-2-(N-((5-oxazolyl)methoxycarbonyl)amino)-1,6-diphenyl-3-hydroxyhexane.

(2S,3S,5S)-5-(N-(N-((N-Methyl-N-((4-cyclohexenyl-4-thiazolyl)methyl)amino)-carbonyl)valinyl)amino)-2-(No((5-oxazolyl)methoxycarbonyl)amino)-1,6-diphenyl-3-hydroxyhexane.

(2S,3S,5S)-5-(N-(N-((N-Methyl-N-((2-(3-propenyl)-4-thiazolyl)methyl)amino)-carbonyl)valinyl)amino)-2-(N-((5-oxazolyl)methoxycarbonyl)amino)-1,6-diphenyl-3-hydroxyhexane.

(2S,3S,5S)-5-(N-(N-((N-Methyl-N-((2-(1-propenyl)-4-thiazolyl)methyl)amino)-carbonyl)valinyl)amino)-2-(N-((5-oxazolyl)methoxycarbonyl)amino)-1,6-diphenyl-3-hydroxyhexane.

(2S,3S,5S)-5-(N-(N-((N-Methyl-N-((2-(1-methyl-1-propenyl)-4-thiazolyl)methyl)-amino)carbonyl)valinyl)amino)-2-(N-((5-oxazolyl)methoxycarbonyl)amino)-1,6-diphenyl-3-hydroxyhexane.

(2S,3S,5S)-5-(N-(N-((N-Methyl-N-((2-(2-methyl-1-propenyl)-4-thiazolyl)methyl)amino)carbonyl)valinyl)amino)-2-(N-((5-oxazolyl)methoxycarbonyl)amino)-1,6-diphenyl-3-hydroxyhexane.

(2S,3S,5S)-5-(N-(N-((N-Methyl-N-((2-(1,2-dimethyl-1-propenyl)-4-thiazolyl)methyl)amino)carbonyl)valinyl)amino)-2-(N-((5-oxazolyl)methoxycarbonyl)amino)-1,6-diphenyl-3-hydroxyhexane.

(2S,3S,5S)-5-(N-(N-((N-Methyl-N-((2-(cyclopentyl)methyl-4-thiazolyl)methyl)-amino)carbonyl)valinyl)amino)-2-(N-((5-oxazolyl)methoxycarbonyl)amino)-1,6-diphenyl-3-hydroxyhexane.

(2S,3S,5S)-5-(N-(N-((N-Methyl-N-((2-(cyclohexyl)methyl-4-thiazolyl)methyl)amino)carbonyl)valinyl)amino)-2-(N-((5-oxazolyl)methoxycarbonyl)amino)-1,6-diphenyl-3-hydroxyhexane.

(2S,3S,5S)-5-(N-(N-((N-Methyl-N-((2-phenyl-4-thiazolyl)methyl)amino)carbonyl)valinyl)amino)-2-(N-((5-oxazolyl)methoxycarbonyl)amino)-1,6-diphenyl-3-hydroxyhexane.

(2S,3S,5S)-5-(N-(N-((N-Methyl-N-((2-benzyl-4-thiazolyl)methyl)amino)carbonyl)valinyl)amino)-2-(N-((5-oxazolyl)methoxycarbonyl)amino)-1,6-diphenyl-3-hydroxyhexane.

(2S,3S,5S)-5-(N-(N-((N-Methyl-N-((2-(2-phenyl)ethyl-4-thiazolyl)methyl)amino)-carbonyl)valinyl)amino)-2-(N-((5-oxazolyl)methoxycarbonyl)amino)-1,6-diphenyl-3-hydroxyhexane.

(2S,3S,5S)-5-(N-(N-((N-Methyl-N-((2-(2-phenyl-1-ethenyl)-4-thiazolyl)methyl)amino)carbonyl)valinyl)amino)-2-(N-((5-oxazolyl)methoxycarbonyl)amino)-1,6-diphenyl-3-hydroxyhexane.

(2S,3S,5S)-5-(N-(N-((N-Methyl-N-((2-(4-fluoro)phenyl-4-thiazolyl)methyl)amino)carbonyl)valinyl)amino)-2-(N-((5-oxazolyl)methoxycarbonyl)amino)-1,6-diphenyl-3-hydroxyhexane.

(2S,3S,5S)-5-(N-(N-((N-Methyl-N-((2-(2-chloro)phenyl-4-thiazolyl)methyl)amino)carbonyl)valinyl)amino)-2-(N-((5-oxazolyl) methoxycarbonyl)amino)-1,6-diphenyl-3-hydroxyhexane.

(2S,3S,5S)-5-(N-(N-((N-Methyl-N-((2-(3-methoxy)phenyl-4-thiazolyl)methyl)amino)carbonyl)valinyl)amino)-2-(N-((5-oxazolyl)methoxycarbonyl)amino)-1,6-diphenyl-3-hydroxyhexane.

(2S,3S,5S)-5-(N-(N-((N-Methyl-N-((2-(2-thiazolyl)-4-thiazolyl)methyl)amino)carbonyl)valinyl)amino)-2-(N-((5-oxazolyl)methoxycarbonyl)amino)-1,6-diphenyl-3-hydroxyhexane.

(2S,3S,5S)-5-(N-(N-((N-Methyl-N-((2-(2-thiazolyl)methyl-4-thiazolyl)methyl)amino)carbonyl)valinyl)amino)-2-(N-((5-oxazolyl)methoxycarbonyl)amino)-1,6-diphenyl-3-hydroxyhexane.

(2S,3S,5S)-5-(N-(N-((N-Methyl-N-((2-methoxy-4-thiazolyl)methyl)amino)carbonyl)valinyl)amino)-2-(N-((5-oxazolyl)methoxycarbonyl)amino)-1,6-diphenyl-3-hydroxyhexane.

(2S,3S,5S)-5-(N-(N-((N-Methyl-N-((2-ethoxy-4-thiazolyl)methyl)amino)carbonyl)valinyl)amino)-2-(N-((5-oxazolyl)methoxycarbonyl)amino)-1,6-diphenyl-3-hydroxyhexane.

(2S,3S,5S)-5-(N-(N-((N-Methyl-N-((2-isopropyloxy-4-thiazolyl)methyl)amino)-carbonyl)valinyl)amino)-2-(N-((5-oxazolyl)methoxycarbonyl)amino)-1,6-diphenyl-3-hydroxyhexane.

(2S,3S,5S)-5-(N-(N-((N-Methyl-N-((2-(N,N-dimethylamino)methyl-4-thiazolyl))-methyl)amino)carbonyl)valinyl)amino)-2-(N-((5-oxazolyl)methoxycarbonyl)-amino)-1,6-diphenyl-3-hydroxyhexane.

(2S,3S,5S)-5-(N-(N-((N-Methyl-N-((2-(1-pyrrolidinyl))methyl-4-thiazolyl)methyl)-amino)carbonyl)valinyl)amino)-2-(N-((5-oxazolyl)methoxycarbonyl)amino)-1,6-diphenyl-3-hydroxyhexane.

(2S,3S,5S)-5-(N-(N-((N-Methyl-N-((2-propyl-4-thiazolyl)methyl)amino)carbonyl)valinyl)amino)-2-(N-((5-oxazolyl)methoxycarbonyl)amino)-1,6-diphenyl-3-hydroxyhexane.

(2S,3S,5S)-5-(N-(N-((N-Methyl-N-((2-(2-methyl)propyl-4-thiazolyl)methyl)amino)carbonyl)valinyl)amino)-2-(N-((5-oxazolyl)methoxycarbonyl)amino)-1,6-diphenyl-3-hydroxyhexane.

(2S,3S,5S)-5-(N-(N-((N-Methyl-N-((2-(1-methyl)propyl-4-thiazolyl)methyl)amino)carbonyl)valinyl)amino)-2-(N-((5-oxazolyl)methoxycarbonyl)amino)-1,6-diphenyl-3-hydroxyhexane.

(2S,3S,5S)-5-(N-(N-((N-Methyl-N-((2-(1-ethyl)propyl-4-thiazolyl)methyl)amino-carbonyl)valinyl)amino)-2-(N-((5-oxazolyl)methoxycarbonyl)amino)-1,6-diphenyl-3-hydroxyhexane.

(2S,3S,5S)-5-(N-(N-((N-Methyl-N-((2-cyclopentyl-4-thiazolyl)methyl)amino)carbonyl)valinyl)amino)-2-(N-((5-isoxazolyl)methoxycarbonyl)amino)-1,6-diphenyl-3-hydroxyhexane.

(2S,3S,5S)-5-(N-(N-((N-Methyl-N-((2-cyclohexyl-4-thiazolyl)methyl)amino)carbonyl)valinyl)amino)-2-(N-((5-isoxazolyl)methoxycarbonyl)amino)-1,6-diphenyl-3-hydroxyhexane.

(2S,3S,5S)-5-(N-(N-((N-Methyl-N-((2-(1,1-dimethyl)ethyl-4-thiazolyl)methyl)amino)carbonyl)valinyl)amino)-2-(N-((5-isoxazolyl)methoxycarbonyl)amino)-1,6-diphenyl-3-hydroxyhexane.

(2S,3S,5S)-5-(N-(N-((N-Methyl-N-((2-cyclobutyl-4-thiazolyl)methyl)amino)carbonyl)valinyl)amino)-2-(N-((5-isoxazolyl)methoxycarbonyl)amino)-1,6-diphenyl-3-hydroxyhexane.

(2S,3S,5S)-5-(N-(N-((N-Methyl-N-((2-cyclopropyl-4-thiazolyl)methyl)amino)carbonyl)valinyl)amino)-2-(N-((5-isoxazolyl)methoxycarbonyl)amino)-1,6-diphenyl-3-hydroxyhexane.

(2S,3S,5S)-5-(N-(N-((N-Methyl-N-((2-ethyl-4-thiazolyl)methyl)amino)carbonyl)valinyl)amino)-2-(N-((5-isoxazolyl)methoxycarbonyl)amino)-1,6-diphenyl-3-hydroxyhexane.

(2S,3S,5S)-5-(N-(N-((N-Methyl-N-((2-ethenyl-4-thiazolyl)methyl)amino)carbonyl)valinyl)amino)-2-(N-((5-isoxazolyl)methoxycarbonyl)amino)-1,6-diphenyl-3-hydroxyhexane.

(2S,3S,5S)-5-(N-(N-((N-Methyl-N-((2-(2-propenyl)-4-thiazolyl)methyl)amino)carbonyl)valinyl)amino)-2-(N-((5-isoxazolyl)methoxycarbonyl)amino)-1,6-diphenyl-3-hydroxyhexane.

(2S,3S,5S)-5-(N-(N-((N-Methyl-N-((2-(1-cyclopentenyl)-4-thiazolyl)methyl)amino)carbonyl)valinyl)amino)-2-(N-((5-isoxazolyl)methoxycarbonyl)amino)-1,6-diphenyl-3-hydroxyhexane.

(2S,3S,5S)-5-(N-(N-((N-Methyl-N-((2-(1-cyclohexenyl)-4-thiazolyl)methyl)amino)carbonyl)valinyl)amino)-2-(N-((5-isoxazolyl)methoxycarbonyl)amino)-1,6-diphenyl-3-hydroxyhexane.

(2S,3S,5S)-5-(N-(N-((N-Methyl-N-((4-cyclopentenyl-4-thiazolyl)methyl)amino-carbonyl)valinyl)amino)-2-(N-((5-isoxazolyl)methoxycarbonyl)amino)-1,6-diphenyl-3-hydroxyhexane.

(2S,3S,5S)-5-(N-(N-((N-Methyl-N-((4-cyclohexenyl-4-thiazolyl)methyl)amino)carbonyl)valinyl)amino)-2-(N-((5-isoxazolyl)methoxycarbonyl)amino)-1,6-diphenyl-3-hydroxyhexane.

(2S,3S,5S)-5-(N-(N-((N-Methyl-N-((2-(3-propenyl)-4-thiazolyl)methyl)amino)carbonyl)valinyl)amino)-2-(N-((5-isoxazolyl)methoxycarbonyl)amino)-1,6-diphenyl-3-hydroxyhexane.

(2S,3S,5S)-5-(N-(N-((N-Methyl-N-((2-(1-propenyl)-4-thiazolyl)methyl)amino)-carbonyl)valinyl)amino)-2-(N-((5-isoxazolyl)methoxycarbonyl)amino)-1,6-diphenyl-3-hydroxyhexane.

(2S,3S,5S)-5-(N-(N-((N-Methyl-N-((2-(1-methyl-1-propenyl)-4-thiazolyl)methyl)-amino)carbonyl)valinyl)amino)-2-(N-((5-isoxazolyl)methoxycarbonyl)amino)-1,6-diphenyl-3-hydroxyhexane.

(2S,3S,5S)-5-(N-(N-((N-Methyl-N-((2-(2-methyl-1-propenyl)-4-thiazolyl)methyl)amino)carbonyl)valinyl)amino)-2-(N-((5-isoxazolyl)methoxycarbonyl)-amino)-1,6-diphenyl-3-hydroxyhexane.

(2S,3S,5S)-5-(N-(N-((N-Methyl-N-((2-(1,2-dimethyl-1-propenyl)-4-thiazolyl)methyl)amino)carbonyl)valinyl)amino)-2-(N-((5-isoxazolyl)methoxycarbonyl)amino)-1,6-diphenyl-3-hydroxyhexane.

(2S,3S,5S)-5-(N-(N-((N-Methyl-N-((2-(cyclopentyl)methyl-4-thiazolyl)methyl)-amino)carbonyl)valinyl)amino)-2-(N-((5-isoxazolyl)methoxycarbonyl)amino)-1,6-diphenyl-3-hydroxyhexane.

(2S,3S,5S)-5-(N-(N-((N-Methyl-N-((2-(cyclohexyl)methyl-4-thiazolyl)methyl)amino)carbonyl)valinyl)amino)-2-(N-((5-isoxazolyl)methoxycarbonyl)amino)-1,6-diphenyl-3-hydroxyhexane.

(2S,3S,5S)-5-(N-(N-((N-Methyl-N-((2-phenyl-4-thiazolyl)methyl)amino)-carbonyl)valinyl)amino)-2-(N-((5-isoxazolyl)methoxycarbonyl)amino)-1,6-diphenyl-3-hydroxyhexane.

(2S,3S,5S)-5-(N-(N-((N-Methyl-N-((2-benzyl-4-thiazolyl)methyl)amino)carbonyl)valinyl)amino)-2-(N-((5-isoxazolyl)methoxycarbonyl)amino)-1,6-diphenyl-3-hydroxyhexane.

(2S,3S,5S)-5-(N-(N-((N-Methyl-N-((2-(2-phenyl)ethyl-4-thiazolyl)methyl)amino)-carbonyl)valinyl)amino)-2-(N-((5-isoxazolyl)methoxycarbonyl)amino)-1,6-diphenyl-3-hydroxyhexane.

(2S,3S,5S)-5-(N-(N-((N-Methyl-N-((2-(2-phenyl-1-ethenyl)-4-thiazolyl)methyl)amino)carbonyl)valinyl)amino)-2-(N-((5-isoxazolyl)methoxycarbonyl)amino)-1,6-diphenyl-3-hydroxyhexane.

(2S,3S,5S)-5-(N-(N-((N-Methyl-N-((2-(4-fluoro)phenyl-4-thiazolyl)methyl)amino)carbonyl)valinyl)amino)-2-(N-((5-isoxazolyl)methoxycarbonyl)amino)-1,6-diphenyl-3-hydroxyhexane.

(2S,3S,5S)-5-(N-(N-((N-Methyl-N-((2-(2-chloro)phenyl-4-thiazolyl)methyl)amino)carbonyl)valinyl)amino)-2-(N-((5-isoxazolyl)methoxycarbonyl)amino)-1,6-diphenyl-3-hydroxyhexane.

(2S,3S,5S)-5-(N-(N-((N-Methyl-N-((2-(3-methoxy)phenyl-4-thiazolyl)methyl)amino)carbonyl)valinyl)amino)-2-(N-((5-isoxazolyl)methoxycarbonyl)amino)-1,6-diphenyl-3-hydroxyhexane.

(2S,3S,5S)-5-(N-(N-((N-Methyl-N-((2-(2-thiazolyl)-4-thiazolyl)methyl)amino)carbonyl)valinyl)amino)-2-(N-((5-isoxazolyl)methoxycarbonyl)amino)-1,6-diphenyl-3-hydroxyhexane.

(2S,3S,5S)-5-(N-(N-((N-Methyl-N-((2-(2-thiazolyl)methyl-4-thiazolyl)methyl)amino)carbonyl)valinyl)amino)-2-(N-((5-isoxazolyl)methoxycarbonyl)amino)-1,6-diphenyl-3-hydroxyhexane.

(2S,3S,5S)-5-(N-(N-((N-Methyl-N-((2-methoxy-4-thiazolyl)methyl)amino)carbonyl)valinyl)amino)-2-(N-((5-isoxazolyl)methoxycarbonyl)amino)-1,6-diphenyl-3-hydroxyhexane.

(2S,3S,5S)-5-(N-(N-((N-Methyl-N-((2-ethoxy-4-thiazolyl)methyl)amino)carbonyl)valinyl)amino)-2-(N-((5-isoxazolyl)methoxycarbonyl)amino)-1,6-diphenyl-3-hydroxyhexane.

(2S,3S,5S)-5-(N-(N-((N-Methyl-N-((2-isopropyloxy-4-thiazolyl)methyl)amino)-carbonyl)valinyl)amino)-2-(N-((5-isoxazolyl)methoxycarbonyl)amino)-1,6-diphenyl-3-hydroxyhexane.

(2S,3S,5S)-5-(N-(N-((N-Methyl-N-((2-(N,N-dimethylamino)methyl-4-thiazolyl)-methyl)amino)carbonyl)valinyl)amino)-2-(N-((5-isoxazolyl)methoxycarbonyl)-amino)-1,6-diphenyl-3-hydroxyhexane.

(2S,3S,5S)-5-(N-(N-((N-Methyl-N-((2-(1-pyrrolidinyl)methyl-4-thiazolyl)methyl)-amino)carbonyl)valinyl)amino)-2-(N-((5-isoxazolyl)methoxycarbonyl)amino)-1,6-diphenyl-3-hydroxyhexane.

(2S,3S,5S)-5-(N-(N-((N-Methyl-N-((2-propyl-4-thiazolyl)methyl)amino)carbonyl)valinyl)amino)-2-(N-((5-isoxazolyl)methoxycarbonyl)amino)-1,6-diphenyl-3-hydroxyhexane.

(2S,3S,5S)-5-(N-(N-((N-Methyl-N-((2-(2-methyl)propyl-4-thiazolyl)methyl)amino)carbonyl)valinyl)amino)-2-(N-((5-isoxazolyl)methoxycarbonyl)amino)-1,6-diphenyl-3-hydroxyhexane.

(2S,3S,5S)-5-(N-(N-((N-Methyl-N-((2-(1-methyl)propyl-4-thiazolyl)methyl)amino)carbonyl)valinyl)amino)-2-(N-((5-isoxazolyl)methoxycarbonyl)amino)-1,6-diphenyl-3-hydroxyhexane.

(2S,3S,5S)-5-(N-(N-((N-Methyl-N-((2-(1-ethyl)propyl-4-thiazolyl)methyl)amino)-carbonyl)valinyl)amino)-2-(N-((5-isoxazolyl)methoxycarbonyl)amino)-1,6-diphenyl-3-hydroxyhexane.

(2S,3S,5S)-5-(N-(N-((N-Methyl-N-((2-cyclopentyl-4-thiazolyl)methyl)amino)carbonyl)valinyl)amino)-2-(N-((5-isothiazolyl)methoxycarbonyl)amino)-1,6-diphenyl-3-hydroxyhexane.

(2S,3S,5S)-5-(N-(N-((N-Methyl-N-((2-cyclohexyl-4-thiazolyl)methyl)amino)carbonyl)valinyl)amino)-2-(N-((5-isothiazolyl)methoxycarbonyl)amino)-1,6-diphenyl-3-hydroxyhexane.

(2S,3S,5S)-5-(N-(N-((N-Methyl-N-((2-(1,1-dimethyl)ethyl-4-thiazolyl)methyl)amino)carbonyl)valinyl)amino)-2-(N-((5-isothiazolyl)methoxycarbonyl)amino)-1,6-diphenyl-3-hydroxyhexane.

(2S,3S,5S)-5-(N-(N-((N-Methyl-N-((2-cyclobutyl-4-thiazolyl)methyl)amino)carbonyl)valinyl)amino)-2-(N-((5-isothiazolyl)methoxycarbonyl)amino)-1,6-diphenyl-3-hydroxyhexane.

(2S,3S,5S)-5-(N-(N-((N-Methyl-N-((2-cyclopropyl-4-thiazolyl)methyl)amino)carbonyl)valinyl)amino)-2-(N-((5-isothiazolyl)methoxycarbonyl)amino)-1,6-diphenyl-3-hydroxyhexane.

(2S,3S,5S)-5-(N-(N-((N-Methyl-N-((2-ethyl-4-thiazolyl)methyl)amino)carbonyl)valinyl)amino)-2-(N-((5-isothiazolyl)methoxycarbonyl)amino)-1,6-diphenyl-3-hydroxyhexane.

(2S,3S,5S)-5-(N-(N-((N-Methyl-N-((2-ethenyl-4-thiazolyl)methyl)amino)carbonyl)valinyl)amino)-2-(N-((5-isothiazolyl)methoxycarbonyl)amino)-1,6-diphenyl-3-hydroxyhexane.

(2S,3S,5S)-5-(N-(N-((N-Methyl-N-((2-(2-propenyl)-4-thiazolyl)methyl)amino)-carbonyl)valinyl)amino)-2-(N-((5-isothiazolyl)methoxycarbonyl)amino)-1,6-diphenyl-3-hydroxyhexane.

(2S,3S,5S)-5-(N-(N-((N-Methyl-N-((2-(1-cyclopentenyl)-4-thiazolyl)methyl)amino)carbonyl)valinyl)amino)-2-(N-((5-isothiazolyl)methoxycarbonyl)amino)-1,6-diphenyl-3-hydroxyhexane.

(2S,3S,5S)-5-(N-(N-((N-Methyl-N-((2-(1-cyclohexenyl)-4-thiazolyl)methyl)amino)carbonyl)valinyl)amino)-2-(N-((5-isothiazolyl)methoxycarbonyl)amino)-1,6-diphenyl-3-hydroxyhexane.

(2S,3S,5S)-5-(N-(N-((N-Methyl-N-((4-cyclopentenyl-4-thiazolyl)methyl)amino)-carbonyl)valinyl)amino)-2-(N-((5-isothiazolyl)methoxycarbonyl)amino)-1,6-diphenyl-3-hydroxyhexane.

(2S,3S,5S)-5-(N-(N-((N-Methyl-N-((4-cyclohexenyl-4-thiazolyl)methyl)amino)-carbonyl)valinyl)amino)-2-(N-((5-isothiazolyl)methoxycarbonyl)amino)-1,6-diphenyl-3-hydroxyhexane.

(2S,3S,5S)-5-(N-(N-((N-Methyl-N-((2-(3-propenyl)-4-thiazolyl)methyl)amino)-carbonyl)valinyl)amino)-2-(N-((5-isothiazolyl)methoxycarbonyl)amino)-1,6-diphenyl-3-hydroxyhexane.

(2S,3S,5S)-5-(N-(N-((N-Methyl-N-((2-(1-propenyl)-4-thiazolyl)methyl)amino)-carbonyl)valinyl)amino)-2-(N-((5-isothiazolyl)methoxycarbonyl)amino)-1,6-diphenyl-3-hydroxyhexane.

(2S,3S,5S)-5-(N-(N-((N-Methyl-N-((2-(1-methyl-1-propenyl)-4-thiazolyl)methyl)-amino)carbonyl)valinyl)amino)-2-(N-((5-sothiazolyl)methoxycarbonyl)amino)-1,6-diphenyl-3-hydroxyhexane.

(2S,3S,5S)-5-(N-(N-((N-Methyl-N-((2-(2-methyl-1-propenyl)-4-thiazolyl)methyl)amino)carbonyl)valinyl)amino)-2-(N-((5-isothiazolyl)methoxycarbonyl)-amino)-1,6-diphenyl-3-hydroxyhexane.

(2S,3S,5S)-5-(N-(N-((N-Methyl-N-((2-(1,2-dimethyl-1-propenyl)-4-thiazolyl)methyl)amino)carbonyl)valinyl)amino)-2-(N-((5-isothiazolyl)methoxycarbonyl)amino)-1,6-diphenyl-3-hydroxyhexane.

(2S,3S,5S)-5-(N-(N-((N-Methyl-N-((2-(cyclopentyl)methyl-4-thiazolyl)methyl)-amino)carbonyl)valinyl)amino)-2-(N-((5-isothiazolyl)methoxycarbonyl)amino)-1,6-diphenyl-3-hydroxyhexane.

(2S,3S,5S)-5-(N-(N-((N-Methyl-N-((2-(cyclohexyl)methyl-4-thiazolyl)methyl)amino)carbonyl)valinyl)amino)-2-(N-((5-isothiazolyl)methoxycarbonyl)amino)-1,6-diphenyl-3-hydroxyhexane.

(2S,3S,5S)-5-(N-(N-((N-Methyl-N-((2-phenyl-4-thiazolyl)methyl)amino)carbonyl)valinyl)amino)-2-(N-((5-isothiazolyl)methoxycarbonyl)amino)-1,6-diphenyl-3-hydroxyhexane.

(2S,3S,5S)-5-(N-(N-((N-Methyl-N-((2-benzyl-4-thiazolyl)methyl)amino)carbonyl)valinyl)amino)-2-(N-((5-isothiazolyl)methoxycarbonyl)amino)-1,6-diphenyl-3-hydroxyhexane.

(2S,3S,5S)-5-(N-(N-((N-Methyl-N-((2-(2-phenyl)ethyl-4-thiazolyl)methyl)amino)-carbonyl)valinyl)amino)-2-(N-((5-isothiazolyl)methoxycarbonyl)amino)-1,6-diphenyl-3-hydroxyhexane.

(2S,3S,5S)-5-(N-(N-((N-Methyl-N-((2-(2-phenyl-1-ethenyl)-4-thiazolyl)methyl)amino)carbonyl)valinyl)amino)-2-(N-((5-isothiazolyl)methoxycarbonyl)amino)-1,6-diphenyl-3-hydroxyhexane.

(2S,3S,5S)-5-(N-(N-((N-Methyl-N-((2-(4-fluoro)phenyl-4-thiazolyl)methyl)amino)carbonyl)valinyl)amino)-2-(N-((5-isothiazolyl)methoxycarbonyl)amino)-1,6-diphenyl-3-hydroxyhexane.

(2S,3S,5S)-5-(N-(N-((N-Methyl-N-((2-(2-chloro)phenyl-4-thiazolyl)methyl)amino)carbonyl)valinyl)amino)-2-(N-((5-isothiazolyl)methoxycarbonyl)amino)-1,6-diphenyl-3-hydroxyhexane.

(2S,3S,5S)-5-(N-(N-((N-Methyl-N-((2-(3-methoxy)phenyl-4-thiazolyl)methyl)amino)carbonyl)valinyl)amino)-2-(N-((5-isothiazolyl)methoxycarbonyl)amino)-1,6-diphenyl-3-hydroxyhexane.

(2S,3S,5S)-5-(N-(N-((N-Methyl-N-((2-(2-thiazolyl)-4-thiazolyl)methyl)amino)carbonyl)valinyl)amino)-2-(N-((5-isothiazolyl)methoxycarbonyl)amino)-1,6-diphenyl-3-hydroxyhexane.

(2S,3S,5S)-5-(N-(N-((N-Methyl-N-((2-(2-thiazolyl)methyl-4-thiazolyl)methyl)amino)carbonyl)valinyl)amino)-2-(N-((5-isothiazolyl)methoxycarbonyl)amino)-1,6-diphenyl-3-hydroxyhexane.

(2S,3S,5S)-5-(N-(N-((N-Methyl-N-((2-methoxy-4-thiazolyl)methyl)amino)-carbonyl)valinyl)amino)-2-(N-((5-isothiazolyl)methoxycarbonyl)amino)-1,6-diphenyl-3-hydroxyhexane.

(2S,3S,5S)-5-(N-(N-((N-Methyl-N-((2-ethoxy-4-thiazolyl)methyl)amino)carbonyl)valinyl)amino)-2-(N-((5-isothiazolyl)methoxycarbonyl)amino)-1,6-diphenyl-3-hydroxyhexane.

(2S,3S,5S)-5-(N-(N-((N-Methyl-N-((2-isopropyloxy-4-thiazolyl)methyl)amino)-carbonyl)valinyl)amino)-2-(N-((5-isothiazolyl)methoxycarbonyl)amino)-1,6-diphenyl-3-hydroxyhexane.

(2S,3S,5S)-5-(N-(N-((N-Methyl-N-((2-(N,N-dimethylamino)methyl-4-thiazolyl)-methyl)amino)carbonyl)valinyl)amino)-2-(N-((5-isothiazolyl)methoxycarbonyl)-amino)-1,6-diphenyl-3-hydroxyhexane.

(2S,3S,5S)-5-(N-(N-((N-Methyl-N-((2-(1-pyrrolidinyl)methyl-4-thiazolyl)methyl)-amino)carbonyl)valinyl)amino)-2-(N-((5-isothiazolyl)methoxycarbonyl)amino)-1,6-diphenyl-3-hydroxyhexane.

(2S,3S,5S)-5-(N-(N-((N-Methyl-N-((2-propyl-4-thiazolyl)methyl)amino)carbonyl)valinyl)amino)-2-(N-((5-isothiazolyl)methoxycarbonyl)amino)-1,6-diphenyl-3-hydroxyhexane.

(2S,3S,5S)-5-(N-(N-((N-Methyl-N-((2-(2-methyl)propyl-4-thiazolyl)methyl)amino)carbonyl)valinyl)amino)-2-(N-((5-isothiazolyl)methoxycarbonyl)amino)-1,6-diphenyl-3-hydroxyhexane.

(2S,3S,5S)-5-(N-(N-((N-Methyl-N-((2-(1-methyl)propyl-4-thiazolyl)methyl)amino)carbonyl)valinyl)amino)-2-(N-((5-isothiazolyl)methoxycarbonyl)amino)-1,6-diphenyl-3-hydroxyhexane.

(2S,3S,5S)-5-(N-(N-((N-Methyl-N-((2-(1-ethyl)propyl-4-thiazolyl)methyl)amino)-carbonyl)valinyl)amino)-2-(N-((5-isothiazolyl)methoxycarbonyl)amino)-1,6-diphenyl-3-hydroxyhexane.

(2S,3S,5S)-5-(N-(N-((N-Methyl-N-((2-isopropyl-4-thiazolyl)methyl)amino)carbonyl)alaninyl)amino)-2-(N-((5-oxazolyl)methoxycarbonyl)amino)-1,6-diphenyl-3-hydroxyhexane.

(2S,3S,5S)-5-(N-(N-((N-Ethyl-N-((2-isopropyl-4-thiazolyl)methyl)amino)carbonyl)valinyl)amino)-2-(N-((5-oxazolyl)methoxycarbonyl)amino)-1,6-diphenyl-3-hydroxyhexane.

(2S,3S,5S)-5-(N-(N-((2-Isopropyl-4-thiazolyl)methoxycarbonyl)valinyl)amino)-2-(N-((5-oxazolyl)methoxycarbonyl)amino)-1,6-diphenyl-3-hydroxyhexane.

(2S,3S,5S)-2-(N-(N-((2-Isopropyl-4-thiazolyl)methoxycarbonyl)valinyl)amino)-5-(N-((5-oxazolyl)methoxycarbonyl)amino)-1,6-diphenyl-3-hydroxyhexane.

(2S,3S,5S)-5-(N-(N-((2-Isopropyl-4-thiazolyl)methoxycarbonyl)alaninyl)amino)-2-(N-((5-oxazolyl)methoxycarbonyl)amino)-1,6-diphenyl-3-hydroxyhexane.

(2S,3S,5S)-5-(N-(N-((2-(N,N-Dimethylamino)-4-thiazolyl)methoxycarbonyl)valinyl)amino)-2-(N-((5-oxazolyl)methoxycarbonyl)amino)-1,6-diphenyl-3-hydroxyhexane.

(2S,3S,5S)-2-(N-(N-((2-(N,N-Dimethylamino)-4-thiazolyl)methoxycarbonyl)valinyl)amino)-5-(N-((5-oxazolyl)methoxycarbonyl)amino)-1,6-diphenyl-3-hydroxyhexane.

(2S,3S,5S)-5-(N-(N-((2-(4-Morpholinyl)-4-thiazolyl)methoxycarbonyl)valinyl)amino)-2-(N-((5-oxazolyl)methoxycarbonyl)amino)-1,6-diphenyl-3-hydroxyhexane.

(2S,3S,5S)-2-(N-(N-((2-(4-Morpholinyl)-4-thiazolyl)methoxycarbonyl)valinyl)amino)-5-(N-((5-oxazolyl)methoxycarbonyl)amino)-1,6-diphenyl-3-hydroxyhexane.

(2S,3S,5S)-5-(N-(N-((2-(1-Pyrrolidinyl)-4-thiazolyl)methoxycarbonyl)valinyl)amino)-2-(N-((5-oxazolyl)methoxycarbonyl)amino)-1,6-diphenyl-3-hydroxyhexane.

(2S,3S,5S)-2-(N-(N-((2-(1-Pyrrolidinyl)-4-thiazolyl)methoxycarbonyl)valinyl)amino)-5-(N-((5-oxazolyl)methoxycarbonyl)amino)-1,6-diphenyl-3-hydroxyhexane.

(2S,3S,5S)-5-(N-(N-((3-Isopropyl-5-isoxazolyl)methoxycarbonyl)valinyl)amino)-2-(N-((5-oxazolyl)methoxycarbonyl)amino)-1,6-diphenyl-3-hydroxyhexane.

(2S,3S,5S)-5-(N-(N-((N-Methyl-N-((2-isopropyl-4-thiazolyl)methyl)amino)carbonyl)alaninyl)amino)-2-(N-((5-isoxazolyl)methoxycarbonyl)amino)-1,6-diphenyl-3-hydroxyhexane.

(2S,3S,5S)-5-(N-(N-((N-Ethyl-N-((2-isopropyl-4-thiazolyl)methyl)amino)carbonyl)valinyl)amino)-2-(N-((5-isoxazolyl)methoxycarbonyl)amino)-1,6-diphenyl-3-hydroxyhexane.

(2S,3S,5S)-5-(N-(N-((2-Isopropyl-4-thiazolyl)methoxycarbonyl)valinyl)amino)-2-(N-((5-isoxazolyl)methoxycarbonyl)amino)-1,6-diphenyl-3-hydroxyhexane.

(2S,3S,5S)-2-(N-(N-((2-Isopropyl-4-thiazolyl)methoxycarbonyl)valinyl)amino)-5-(N-((5-isoxazolyl)methoxycarbonyl)amino)-1,6-diphenyl-3-hydroxyhexane.

(2S,3S,5S)-5-(N-(N-((2-Isopropyl-4-thiazolyl)methoxycarbonyl)alaninyl)amino)-2-(N-((5-isoxazolyl)methoxycarbonyl)amino)-1,6-diphenyl-3-hydroxyhexane.

(2S,3S,5S)-5-(N-(N-((2-(N,N-Dimethylamino)-4-thiazolyl)methoxycarbonyl)valinyl)amino)-2-(N-((5-isoxazolyl)methoxycarbonyl)amino)-1,6-diphenyl-3-hydroxyhexane.

(2S,3S,5S)-2-(N-(N-((2-(N,N-Dimethylamino)-4-thiazolyl)methoxycarbonyl)valinyl)amino)-5-(N-((5-isoxazolyl)methoxycarbonyl)amino)-1,6-diphenyl-3-hydroxyhexane.

(2S,3S,5S)-5-(N-(N-((2-(4-Morpholinyl)-4-thiazolyl)methoxycarbonyl)valinyl)amino)-2-(N-((5-isoxazolyl)methoxycarbonyl)amino)-1,6-diphenyl-3-hydroxyhexane.

(2S,3S,5S)-2-(N-(N-((2-(4-Morpholinyl)-4-thiazolyl)methoxycarbonyl)valinyl)amino)-5-(N-((5-isoxazolyl)methoxycarbonyl)amino)-1,6-diphenyl-3-hydroxyhexane.

(2S,3S,5S)-5-(N-(N-((2-(1-Pyrrolidinyl)-4-thiazolyl)methoxycarbonyl)valinyl)amino)-2-(N-((5-isoxazolyl)methoxycarbonyl)amino)-1,6-diphenyl-3-hydroxyhexane.

(2S,3S,5S)-2-(N-(N-((2-(1-Pyrrolidinyl)-4-thiazolyl)methoxycarbonyl)valinyl)amino)-5-(N-((5-isoxazolyl)methoxycarbonyl)amino)-1,6-diphenyl-3-hydroxyhexane.

(2S,3S,5S)-5-(N-(N-((3-Isopropyl-5-isoxazolyl)methoxycarbonyl)valinyl)amino)-2-(N-((5-isoxazolyl)methoxycarbonyl)amino)-1,6-diphenyl-3-hydroxyhexane.

(2S,3S,5S)-5-(N-(N-((N-Methyl-N-((2-isopropyl-4-thiazolyl)methyl)amino)carbonyl)alaninyl)amino)-2-(N-((5-isothiazolyl)methoxycarbonyl)amino)-1,6-diphenyl-3-hydroxyhexane.

(2S,3S,5S)-5-(N-(N-((N-Ethyl-N-((2-isopropyl-4-thiazolyl)methyl)amino)carbonyl)valinyl)amino)-2-(N-((5-isothiazolyl)methoxycarbonyl)amino)-1,6-diphenyl-3-hydroxyhexane.

(2S,3S,5S)-5-(N-(N-((2-Isopropyl-4-thiazolyl)methoxycarbonyl)valinyl)amino)-2-(N-((5-isothiazolyl)methoxycarbonyl)amino)-1,6-diphenyl-3-hydroxyhexane.

(2S,3S,5S)-2-(N-(N-((2-Isopropyl-4-thiazolyl)methoxycarbonyl)valinyl)amino)-5-(N-((5-isothiazolyl)methoxycarbonyl)amino)-1,6-diphenyl-3-hydroxyhexane.

(2S,3S,5S)-5-(N-(N-((2-Isopropyl-4-thiazolyl)methoxycarbonyl)alaninyl)amino)-2-(N-((5-isothiazolyl)methoxycarbonyl)amino)-1,6-diphenyl-3-hydroxyhexane.

(2S,3S,5S)-5-(N-(N-((2-(N,N-Dimethylamino)-4-thiazolyl)methoxycarbonyl)valinyl)amino)-2-(N-((5-isothiazolyl)methoxycarbonyl)amino)-1,6-diphenyl-3-hydroxyhexane.

(2S,3S,5S)-2-(N-(N-((2-(N,N-Dimethylamino)-4-thiazolyl)methoxycarbonyl)valinyl)amino)-5-(N-((5-isothiazolyl)methoxycarbonyl)amino)-1,6-diphenyl-3-hydroxyhexane.

(2S,3S,5S)-5-(N-(N-((2-(4-Morpholinyl)-4-thiazolyl)methoxycarbonyl)valinyl)amino)-2-(N-((5-isothiazolyl)methoxycarbonyl)amino)-1,6-diphenyl-3-hydroxyhexane.

(2S,3S,5S)-2-(N-(N-((2-(4-Morpholinyl)-4-thiazolyl)methoxycarbonyl)valinyl)amino)-5-(N-((5-isothiazolyl)methoxycarbonyl)amino)-1,6-diphenyl-3-hydroxyhexane.

(2S,3S,5S)-5-(N-(N-((2-(1-Pyrrolidinyl)-4-thiazolyl)methoxycarbonyl)valinyl)amino)-2-(N-((5-isothiazolyl)methoxycarbonyl)amino)-1,6-diphenyl-3-hydroxyhexane.

(2S,3S,5S)-2-(N-(N-((2-(1-Pyrrolidinyl)-4-thiazolyl)methoxycarbonyl)valinyl)amino)-5-(N-((5-isothiazolyl)methoxycarbonyl)amino)-1,6-diphenyl-3-hydroxyhexane.

(2S,3S,5S)-5-(N-(N-((3-Isopropyl-5-isoxazolyl)methoxycarbonyl)valinyl)amino)-2-(N-((5-isothiazolyl)methoxycarbonyl)amino)-1,6-diphenyl-3-hydroxyhexane.

(2S,3S,5S)-5-(N-(N-((N-Methyl-N-((2-isopropyl-4-oxazolyl)methyl)amino)carbonyl)valinyl)amino)-2-(N-((5-isothiazolyl)methoxycarbonyl)amino)-1,6-diphenyl-3-hydroxyhexane.

EXAMPLE 41

(2S,3S,5S)-5-(N-(N-((N-Methyl-N-((2-ethyl-4-oxazolyl)methyl)amino)carbonyl)valinyl)amino)-2-(N-((5thiazolyl)methoxycarbonyl)amino)-1,6-diphenyl-3-hydroxyhexane Using the procedures of Example 18A–F, but replacing isobutyramide with propionamide, provided the desired compound. $^1$H NMR (DMSO-d$_6$) δ0.74 (d, J=6 Hz, 6H), 1.19 (t, J=7 Hz, 3H), 1.38–1.51 (m, 2H), 1.80–1.94 (m, 1H), 2.54–2.74 (m, 5H), 2.83 (s, 3H), 3.53–3.63 (m, 1H), 3.82 (br q, 1H), 3.92 (t, J=8 Hz, 1H), 4.13, (m, 1H), 4.26 (AA', 2H), 4.63 (d, J=6 Hz, 1H), 5.13 (AA', 2H), 5.90 (d, J=9 Hz, 1H), 6.89 (d, J=9 Hz, 1H), 7.07–7.25 (m, 12H), 7.68 (d, J=8.7 Hz, 1H), 7.77 (s, 1H), 7.86 (s, 1H), 9.05 (s, 1H). Mass spectrum: (M+H)$^+$=691. Anal. Calcd for C$_{36}$H$_{46}$N$_6$O$_6$S.0.3H$_2$O: C, 62.10; H, 6.75; N, 12.07. Found: C, 62.42; H, 6.68; N, 11.69.

EXAMPLE 42

(2S,3S,5S)-5-(N-(N-((N-Methyl-N-((2-methyl-4-oxazolyl)methyl)amino)carbonyl)valinyl)amino)-2-(N-((5-thiazolyl)methoxycarbonyl)amino)-1,6-diphenyl-3-hydroxyhexane Using the procedures of Example 18A–F, but replacing isobutyramide with acetamide, provided the desired compound. Mass spectrum: (M+H)$^+$=677.

EXAMPLE 43

(2S,3S,5S)-5-(N-(N-((N-Methyl-N-((2-isopropyl-4-thiazolyl)methyl)amino)carbonyl)valinyl)amino)-1-phenyl-2-(N-((5-thiazolyl)methoxycarbonyl)amino)-6-(5-oxazolyl)-3-hydroxyhexane Using the procedures of Example 8C–8K, but replacing 5-chloromethylthiazole hydrochloride with 5-chloromethyloxazole hydrochloride provided the desired compound.

EXAMPLE 44

A. 2-Ethylbutanamide

A solution of 21.5 ml of oxalyl chloride (2M, 43 mmol) in dichloromethane was treated with 5.0 g (43 mmol) of 2-ethylbutyric acid followed by 0.1 ml of dimethylformamide. The resulting solution was stirred at ambient temperature for 1 h, during which gas evolution was observed. After the termination of gas evolution, the solution was concentrated in vacuo to give crude 2-ethylbutyryl chloride. The crude acid chloride was taken up in 200 ml of acetone and treated with 4.6 g (60 mmol) of ammonium acetate. The resulting mixture was stirred at ambient temperature for 1 h, filtered, and concentrated in vacuo to provide 4.2 g (85%) of the desired compound. $^1$H NMR (d$_6$-DMSO) δ0.80 (t, J -7 Hz, 6H), 1.32 (m, 2H), 1.45 (m, 2H), 1.93 (m, 1H), 6.71 (br, 1H), 7.23 (br, 1H).

B. 2-Ethylbutane-thioamide

Using the procedure of Example 10, but replacing isobutyramide with 2-ethylbutanamide provided 1.6 g (25%) of the crude desired compound.

C. 4-(Chloromethyl)-2-(3-pentyl)thiazole hydrochloride

Using the procedure of Example 1P, but replacing 2-methylpropanethioamide with 2-ethylbutane-thioamide provided the crude desired compound as a yellow oil.

D. 2-(3-Pentyl)-4-(((N-methyl)amino)methyl)thiazole

Using the procedure of Example 1Q, but replacing 4-(chloromethyl)-2-isopropylthiazole hydrochloride with 4-(chloromethyl)-2-(3-pentyl)thiazole hydrochloride provided, after purification of the residue by silica gel chromatography using 5% methanol in chloroform, 1.5 g (71%) of the desired compound.

E. N-((N-Methyl-N-((2-(3-pentyl)-4-thiazolyl)methyl)amino)carbonyl)-L-valine Methyl Ester Using the procedure of Example 1S, but replacing 2-isopropyl-4-(((N-methyl)amino)methyl)thiazole with 2-(3-pentyl)-4-(((N-methyl)amino)methyl)thiazole provided, after purification by silica gel chromatography using 3% methanol in chloroform as an eluent, 1.6 g (61%) of the desired compound.

F. N-((N-Methyl-N-((2-(3-pentyl)-4-thiazolyl)methyl)amino)carbonyl)-L-valine Using the procedure of Example 1T, but replacing the resultant compound of Example 1S with the resultant compound of Example 44E provided 0.4 g (52%) of the desired compound.

G. (2S,3S,5S)-5-(N-(N-((N-Methyl-N-((2-(3-pentyl)-4-thiazolyl)methyl)amino)carbonyl)valinyl)amino)-2-(N-((5-thiazolyl)methoxycarbonyl)amino)-1,6-diphenyl-3-hydroxyhexane Using the procedure of Example 1U, but replacing N-((N-methyl-N-((2-isopropyl-4-thiazolyl)methyl)amino)carbonyl)-L-valine with N-((N-methyl-N-((2-(3-pentyl)-4-thiazolyl)methyl)amino)carbonyl)-L-valine provided, after purification by silica gel chromatography using 99:1 $CHCl_3:CH_3OH$, 72 mg (41%) of the desired compound ($R_f$ 0.3, 95:5 $CHCl_3:CH_3OH$) as a solid, mp 64°–66° C. Mass spectrum: $(M+H)^+=749$. Anal. Calcd for $C_{39}H_{52}N_6O_5S_2$: C, 62.54; H, 7.00; N, 11.22; S, 8.56. Found: C, 62.67; H, 6.85; N, 11.06; S, 8.45.

EXAMPLE 45

A. (((2-Isopropyl)-5-thiazolyl)methyl)-(4-nitrophenyl)carbonate

Using the procedure of Example 1L, but replacing 5-(hydroxymethyl)thiazole with 5-(hydroxymethyl)-2-isopropylthiazole provided, after purification by silica gel chromatography using 1% $MeOH/CHCl_3$, 0.7 g (78%) of the desired compound, Rf=0.8 (5% $MeOH/CHCl_3$).

B. (2S,3S,5S)-5-Amino-2-(N-(((2-isopropyl)-5-thiazolyl)methoxycarbonyl)amino)-1,6-diphenyl-3-hydroxyhexane Using the procedure of Example 1N, but replacing ((5-thiazolyl)methyl)-(4-nitrophenyl)carbonate with (((2-isopropyl)-5-thiazolyl)methyl)-(4-nitrophenyl)carbonate provided, after purification by silica gel chromatography using 99:2:1 $CHCl_3$:isopropylamine:$CH_3OH$, Rf=0.2, 0.17 g (18%) of the desired compound, (1% isopropylamine in $CHCl_3$). $^1H$ NMR ($d_6$-DMSO) δ1.38 (d, J=7 Hz, 6H), 1.43 (m, 1H), 1.64 (m, 1H), 2.46 (dd, J=14, 8 Hz, 1H), 2.63 (m, 2H), 2.80 (dd, J=14, 5 Hz, 1H), 2.94 (m, 1H), 3.21 (m, 1H), 3.64 (m, 2H), 5.09 (AA', 2H), 6.98 (d, J=9 Hz, 1H), 7.1–7.3 (m, 10H), 7.60 (s, 1H). Mass spectrum: $(M+H)^+=468$.

C. (2S,3S,5)-5-(N-(N-((N-Methyl-N-((2-isopropyl-4-thiazolyl)methy)amino)carbonyl)valinyl)amino)-2-(N-(((2-isopropyl)-5-thiazolyl)methoxycarbonyl)amino)-1,6-diphenyl-3-hydroxyhexane Using the procedure of Example 1U, but replacing (2S,3S,5S)-5-amino-2-(N-((5-thiazolyl)methoxycarbonyl)amino)-1,6-diphenyl-3-hydroxyhexane with (2S,3S,5S)-5-amino-2-(N-(((2-isopropyl)-5-thiazolyl)methoxycarbonyl)amino)-1,6-diphenyl-3-hydroxyhexane provided, after purification by silica gel chromatography using 99:1 $CHCl_3:CH_3OH$, 50 mg (61%) of the desired compound ($R_f$ 0.28, 95:5 $CHCl_3:CH_3OH$) as a solid, mp 64°–66° C. Mass spectrum: $(M+H)^+=764$. Anal. Calcd for $C_{40}H_{54}N_6O_5S_2$: C, 62.97; H, 7.13; N, 11.01. Found: C, 62.91; H, 7.11; N, 10.81.

EXAMPLE 46

A. 1-(Aminothiocarbonyl)pyrrolidine

A solution of 1.0 g (14 mmol) of pyrrolidine in 70 ml of tetrahydrofuran was treated dropwise with 2.0 ml of trimethylsilylisocyanate. The resulting solution was stirred at ambient temperature for two days, and concentrated in vacuo. Purification of the residue by silica gel chromatography using 4% methanol in chloroform provided the desired compound ($R_f$ 0.5, 10% methanol in chloroform).

B. 4-(Chloromethyl)-2-(1-pyrrolidinyl)thiazole hydrochloride

Using the procedure of Example 1P, but replacing 2-methylpropanethioamide with 1-(aminothiocarbonyl)pyrrolidine provided the crude desired compound.

C. 2-(1-Pyrrolidinyl)-4-(((N-methyl)amino)methyl)thiazole

Using the procedure of Example 1Q, but replacing 4-(chloromethyl)-2-isopropylthiazole hydrochloride with 4-(chloromethyl)-2-(1-pyrrolidinyl)thiazole hydrochloride provided, after purification of the residue by silica gel chromatography using 2% isopropylamine/2% methanol in chloroform, 0.89 g (30%) of the desired compound. $^1H$ NMR ($CDCl_3$) δ2.02 (m, 4H), 2.61 (s, 3H), 3.44 (m, 4H), 3.90 (s, 2H), 4.84 (br, 1H), 6.51 (s, 1H). Mass spectrum: $(M+H)^+=198$.

D. N-((N-Methyl-N-((2-(1-pyrrolidinyl)-4-thiazolyl)methyl)amino)carbonyl)-L-valine Methyl Ester Using the procedure of Example 1S, but replacing 2-isopropyl-4-(((N-methyl)amino)methyl)thiazole with 2-(1-pyrrolidinyl)-4-(((N-methyl)amino)methyl)thiazole provided, after purification by silica gel chromatography using 4% methanol in chloroform as an eluent, 0.63 g (39%) of the desired compound. $^1H$ NMR ($CDCl_3$) δ0.96 (t, J=7 Hz, 3H), 0.98 (t, J=7 Hz, 3H), 2.04 (m, 4H), 2.14 (heptet, J=7 Hz, 1H), 2.97 (s, 3H), 3.45 (m, 4H), 3.71 (s, 3H), 4.10 (m, 1H), 4.33 (dd, J=9, 6 Hz, 1H), 4.42 (br d, J=16 Hz, 1H), 6.26 (s, 1H), 6.45 (br, 1H). Mass spectrum: $(M+H)^+=355$.

E. N-((N-Methyl-N-((2-(1-pyrrolidinyl)-4-thiazolyl)methyl)amino)carbonyl)-L-valine Using the procedure of Example 1T, but replacing the resultant compound of Example 1S with the resultant compound of Example 46D provided 0.24 g (96%) of the desired compound.

F. (2S,3S,5S)-5-(N-(N-((N-Methyl-N-((2-(1-pyrrolidinyl)-4-thiazolyl)methyl)amino)carbonyl)valinyl)amino)-2-(N-((5-thiazolyl)methoxycarbonyl)amino)-1,6-diphenyl-3-hydroxyhexane Using the procedure of Example 1U, but replacing N-((N-methyl-N-((2-isopropyl-4-thiazolyl)methyl)amino)carbonyl)-L-valine with N-((N-methyl-N-((2-(1-pyrrolidinyl)-4-thiazolyl)methyliamino)carbonyl)-L-valine provided, after purification by silica gel chromatography using 2% methanol in chloroform, the desired compound ($R_f$ 0.29, 4% methanol in chloroform). Mass spectrum: $(M+H)^+=748$.

EXAMPLE 47

A. Ethyl 2-(2-Isopropyl-4-thiazolyl)acetate

Using the procedure of Example 1P, but replacing 1,3-dichloroacetone with ethyl 4-chloroacetoacetate provided, after purification by silica gel chromatography using $CHCl_3$, the desired compound in 34% yield. $^1H$ NMR ($d_6$-DMSO) δ1.18 (t, J=7 Hz, 3H), 1.30 (d, J=7 Hz, 6H), 3.24 (heptet, J=7 Hz, 1H), 3.76 (s, 2H), 4.09 (q, J=7 Hz, 2H), 7.31 (s, 1H). Mass spectrum: $(M+H)^+=214$.

B. 4-(2-Hydroxyethyl)-2-isopropylthiazole

Using the procedure of Example 5B, but replacing ethyl 2-isopropyl-4-thiazolecarboxylate with ethyl 2-(2-isopropyl-4-thiazolyl)acetate provided, after purification of the residue by silica gel chromatography using 2% methanol in chloroform, 0.9 g (47%) of the desired compound. $^1$H NMR (CDCl$_3$) δ1.40 (d, J=7 Hz, 6H), 2.95 (t, J=6 Hz, 2H), 3.30 (heptet, J=7 Hz, 1H), 3.92 (t, J=6 Hz, 2H), 6.83 (s, 1H). Mass spectrum: (M+H)$^+$=172.

C. N-((2-(2-Isopropyl-4-thiazolyl)ethoxy)carbonyl)valine Methyl Ester

Using the procedure of Example 5D, but replacing 4-(hydroxymethyl)-2-isopropylthiazole with 4-(2-hydroxyethyl)-2-isopropylthiazole provided, after purification by silica gel chromatography using 3% methanol in chloroform as an eluent, 0.8 g (52%) of the desired compound.

D. N-((2-(2-Isopropyl-4-thiazolyl)ethoxy)carbonyl)valine

Using the procedure of Example 1T, but replacing the resultant compound of Example 1S with the resultant compound of Example 47C provided 0.17 g (82%) of the desired compound.

E. (2S,3S,5S)-5-(N-(N-((2-(2-Isopropyl-4-thiazolyl)ethoxy)carbonyl)valinyl)amino)-2-(N-((5-thiazolyl)methoxycarbonyl)amino)-1,6-diphenyl-3-hydroxyhexane Using the procedure of Example 1U, but replacing N-((N-methyl-N-((2-isopropyl-4-thiazolyl)methyl)amino)carbonyl)-L-valine with N-((2-(2-isopropyl-4-thiazolyl)ethoxy)carbonyl)valine provided, after purification by silica gel chromatography using 99:1 CHCl$_3$:CH$_3$OH, 80 mg (47%) of the desired compound (R$_f$ 0.3, 95:5 CHCl$_3$:CH$_3$OH) as a solid, mp 146°–147° C. Mass spectrum: (M+H)$^+$=722. Anal. Calcd for C$_{37}$H$_{47}$N$_5$O$_6$S$_2$: C, 61.56; H, 6.56; N, 9.70. Found: C, 61.24; H, 6.48; N, 9.53.

EXAMPLE 48

E. (2S,3S,5S)-2-(N-(N-((2-(2-Isopropyl-4-thiazolyl)ethoxy)carbonyl)valinyl)amino)-5-(N-((5-thiazolyl)methoxycarbonyl)amino)-1,6-diphenyl-3-hydroxyhexane Using the procedure of Example 1U, but replacing N-((N-methyl-N-((2-isopropyl-4-thiazolyl)methyl)amino)carbonyl)-L-valine with N-((2-(2-isopropyl-4-thiazolyl)ethoxy)carbonyl)valine and replacing (2S,3S,5S)-5-amino-2-(N-((5-thiazolyl)methoxycarbonyl)amino)-1,6-diphenyl-3-hydroxyhexane with (2S,3S,5S)-2-amino-5-(N-((5-thiazolyl)methoxycarbonyl)amino)-1,6-diphenyl-3-hydroxyhexane provided, after purification by silica gel chromatography using 99:1 CHCl$_3$:CH$_3$OH, 50 mg (30%) of the desired compound (R$_f$ 0.3, 95:5 CHCl$_3$:CH$_3$OH) as a solid, mp 159°–160° C. Mass spectrum: (M+H)$^+$=722 HRMS. Exact mass calcd for C$_{37}$H$_{47}$N$_5$O$_6$S$_2$: 722.3046. Found: 722.3036.

EXAMPLE 49

(2S,3S,5S)-5-(N-(N-((N-Methyl-N-((2-(1-pyrrolidinyl)-4-thiazolyl)methyl)amino)carbonyl)valinyl)amino)-2-(N-((5-isoxazolyl)methoxycarbonyl)amino)-1,6-diphenyl-3-hydroxyhexane Using the procedure of Example 1U, but replacing N-((N-methyl-N-((2-isopropyl-4-thiazolyl)methyl)amino)carbonyl)-L-valine with N-((N-methyl-N-((2-(1-pyrrolidinyl))-4-thiazolyl)methyl)amino)carbonyl)-L-valine and replacing (2S,3S,5S)-5-amino-2-(N-((5-thiazolyl)methoxycarbonyl)amino)-1,6-diphenyl-3-hydroxyhexane with (2S,3S,5S)-5-amino-2-(N-((5-isoxazolyl)methoxy-carbonyl)amino)-1,6-diphenyl-3-hydroxyhexane provided, after purification by silica gel chromatography using 2% methanol in chloroform, the desired compound (R$_f$ 0.30, 4% methanol in chloroform).

EXAMPLE 50

A. (2S,3S,5S)-5-(N-(N-(t-Butyloxycarbonyl)valinyl)amino)-2-(N-((5-thiazolyl)methoxycarbonyl)amino)-1,6-diphenyl-3-hydroxyhexane Using the procedure of Example 1U, but replacing N-((N-methyl-N-((2-isopropyl-4-thiazolyl)methyl)amino)carbonyl)-L-valine with N-(t-butyloxycarbonyl)valine provided, after silica gel chromatography using 1% methanol in chloroform, the desired compound (R$_f$ 0.31, 4% methanol in chloroform).

B. (2S,3S,5S)-5-(N-(Valinyl)amino)-2-(N-((5-thiazolyl)methoxycarbonyl)amino)-1,6-diphenyl-3-hydroxyhexane Hydrochloride To 135 mg (0.27 mmol) of (2S,3S,5S)-5-(N-(N-(t-butyloxycarbonyl)valinyl)amino)-2-(N-((5-thiazolyl)methoxycarbonyl)amino)-1,6-diphenyl-3-hydroxyhexane was added 8 ml of 4M HCl in dioxane. The resulting mixture was stirred at ambient temperature for 1 h and concentrated in vacuo to provide the crude desired compound.

C. 2-(2-Isopropyl-4-thiazolyl)acetic Acid

Using the procedure of Example 1T, but replacing the resultant compound of Example 1S with the resultant compound of Example 47A provided 0.24 g (55%) of the desired compound. $^1$H NMR (CDCl$_3$) δ1.93 (d, a =7 Hz, 6H), 3.35 (heptet, J=7 Hz, 1H), 3.85 (s, 2H), 7.00 (s, 1H). Mass spectrum: (M+H)$^+$=186.

D. (2S,3S,5S)-5-(N-(N-(2-Isopropyl-4-thiazolyl)acetyl)valinyl)amino)-2-(N-((5-thiazolyl)methoxycarbonyl)amino)-1,6-diphenyl-3-hydroxyhexane Using the procedure of Example 1U, but replacing N-((N-methyl-N-((2-isopropyl-4-thiazolyl)methyl)amino)carbonyl)-L-valine with 2-(2-isopropyl-4-thiazolyl)acetic acid provided, after purification by silica gel chromatography using 99:1 CHCl$_3$:CH$_3$OH, 120 mg (80%) of the desired compound (R$_f$ 0.6, 95:5 CHCl$_3$:CH$_3$OH) as a solid, mp 153°–155° C. Mass spectrum: (M+H)$^+$=692. Anal. Calcd for C$_{36}$H$_{45}$N$_5$O$_5$S$_2$.0.5H$_2$O: C, 61.69; H, 6.62; N, 9.99; S, 9.15. Found: C, 61.92; H, 6.49; N, 10.06; S, 8.81.

EXAMPLE 51

A. Cyclopropanecarboxamide

Using the procedure of Example 44A but replacing 2-ethylbutyric acid with cyclopropanecarboxylic acid provided 6.4 g (50%) of the crude desired compound.

B. Cyclopropanethiocarboxamide

Using the procedure of Example 1O, but replacing isobutyramide with cyclopropanecarboxamide provided 7.2 g (96%) of the crude desired compound.

C. 4-(Chloromethyl)-2-cyclopropylthiazole hydrochloride

Using the procedure of Example 1P, but replacing 2-methylpropanethioamide with cyclopropanethiocarboxamide provided the crude desired compound as a yellow oil.

D. 2-Cyclopropyl-4-(((N-methyl)amino)methyl)thiazole

Using the procedure of Example 1Q, but replacing 4-(chloromethyl)-2-isopropylthiazole hydrochloride With 4-(chloromethyl)-2-cyclopropylthiazole hydrochloride provided, after purification of the residue by silica gel chromatography using 5% methanol in chloroform, 0.5 g (25%) of the desired compound.

E. N-((N-Methyl-N-((2-cyclopropyl-4-thiazolyl)methyl)amino)carbonyl)-L-valine Methyl Ester Using the procedure of Example 1S, but replacing 2-isopropyl-4-(((N-methyl)amino)methyl)thiazole with 2-cyclopropyl-4-(((N-methyl)amino)methyl)thiazole provided, after purification by silica gel chromatography using 1% methanol/chloroform as an eluent, 0.4 g (48%) of the desired compound.

F. N-((N-Methyl-N-((2-cyclopropyl-4-thiazolyl)methyl)amino)carbonyl)-L-valine Using the procedure of Example 1T, but replacing the resultant compound of Example 1S with the resultant compound of Example 51E provided 0.16 g (70%) of the desired compound.

G. (2S,3S,5S)-5-(N-(N-((N-Methyl-N-((2-cyclopropyl-4-thiazolyl)methy)amino)carbonyl)valinyl)amino)-2-(N-((5-thiazolyl)methoxycarbonyl)amino)-1,6-diphenyl-3-hydroxyhexane Using the procedure of Example 1U, but replacing N-((N-methyl-N-((2-isopropyl-4-thiazolyl)methyl)amino)carbonyl)-L-valine with N-((N-methyl-N-((2-cyclopropyl-4-thiazolyl)methyl)amino)carbonyl)-L-valine provided, after purification by silica gel chromatography using 1% methanol in chloroform, 90 mg (54%) of the desired compound ($R_f$ 0.2, 95:5 CHCl$_3$:CH$_3$OH) as a solid, mp 70°–71° C. Mass spectrum: (M+H)$^+$=719. Anal. Calcd for C$_{37}$H$_{46}$N$_6$O$_5$S$_2$: C, 61.82; H, 6.45; N, 11.69. Found: C, 61.50; H, 6.46; N, 11.41.

EXAMPLE 52

A. Cyclobutanecarboxamide

Using the procedure of Example 44A but replacing 2-ethylbutyric acid with cyclobutanecarboxylic acid provided 7.5 g (76%) of the crude desired compound.

B. Cyclobutanethiocarboxamide

Using the procedure of Example 1O, but replacing isobutyramide with cyclobutanecarboxamide provided 6.9 g (80%) of the crude desired compound.

C. 4-(Chloromethyl)-2-cyclobutylthiazole hydrochloride

Using the procedure of Example 1P, but replacing 2-methylpropanethioamide with cyclobutanethiocarboxamide provided the crude desired compound as a yellow oil.

D. 2-Cyclobutyl-4-(((N-methyl)amino)methyl)thiazole

Using the procedure of Example 1Q, but replacing 4-(chloromethyl)-2-isopropylthiazole hydrochloride with 4-(chloromethyl)-2-cyclobutylthiazole hydrochloride provided, after purification of the residue by silica gel chromatography using 5% methanol in chloroform, 1.0 g (36%) of the desired compound.

E. N-((N-Methyl-N-((2-cyclobutyl-4-thiazolyl)methyl)amino)carbonyl)-L-valine Methyl Ester Using the procedure of Example 1S, but replacing 2-isopropyl-4-(((N-methyl)amino)methyl)thiazole with 2-cyclobutyl-4-(((N-methyl)amino)methyl)-thiazole provided, after purification by silica gel chromatography using 1% methanol in chloroform as an eluent, 0.54 g (31%) of the desired compound. Mass spectrum: (M+H)$^+$=340.

F. N-((N-Methyl-N-((2-cyclobutyl-4-thiazolyl)methyl)amino)carbonyl)-L-valine Using the procedure of Example 1T, but replacing the resultant compound of Example 1S with the resultant compound of Example 52E provided 0.2 g (42%) of the desired compound.

G. (2S,3S,5S)-5-(N-(N-((N-Methyl-N-((2-cyclobutyl-4-thiazolyl)methyl)amino)carbonyl)valinyl)amino)-2-(N-((5-thiazolyl)methoxycarbonyl)amino)-1,6-diphenyl-3-hydroxyhexane Using the procedure of Example 1U, but replacing N-((N-methyl-N-((2-isopropyl-4-thiazolyl)methyl)amino)carbonyl)-L-valine with N-((N-methyl-N-((2-cyclobutyl-4-thiazolyl)methyl)amino)carbonyl)-L-valine provided, after purification by silica gel chromatography using 1% methanol in chloroform, 110 mg (64%) of the desired compound ($R_f$ 0.17, 95:5 CH$_2$Cl$_2$:CH$_3$OH) as a solid, mp 74°–76° C. Mass spectrum: (M+H)$^+$=733. Anal. Calcd for C$_{38}$H$_{48}$N$_6$O$_5$S$_2$: C, 62.27; H, 6.60; N, 11.47; S, 8.75. Found, C, 62.02; H, 6.73; N, 11.33; S, 8.51.

EXAMPLE 53

A. Propanethioamide

Using the procedure of Example 1O, but replacing isobutyramide with propionamide provided 4.6 g (38%) of the crude desired compound. $^1$H NMR (CDCl$_3$) δ1.33 (t, J=7 Hz, 3H), 2.70 (q, J=7 Hz, 2H), 6.9 (br, 1H), 7.6 (br, 1H). Mass spectrum: (M+H)$^+$=90.

B. 4-(Chloromethyl)-2-ethylthiazole hydrochloride

Using the procedure of Example 1P, but replacing 2-methylpropanethioamide with propanethioamide provided the crude desired compound as a yellow oil.

C. 2-Ethyl-4-(((N-methyl)amino)methyl)thiazole

Using the procedure of Example 1Q, but replacing 4-(chloromethyl)-2-isopropylthiazole hydrochloride with 4-(chloromethyl)-2-ethylthiazole hydrochloride provided 1.0 g (52%) of the desired compound.

D. N-((N-Methyl-N-((2-ethyl-4-thiazolyl)methyl)amino)carbonyl)-L-valine Methyl Ester Using the procedure of Example 1S, but replacing 2-isopropyl-4-(((N-methyl)amino)methyl)thiazole with 2-ethyl-4-(((N-methyl)amino)methyl)thiazole provided, after purification by silica gel chromatography using 1% methanol in chloroform as an eluent, 0.7 g (35%) of the desired compound.

E. N-((N-Methyl-N-((2-ethyl-4-thiazolyl)methyl)amino)carbonyl)-L-valine

Using the procedure of Example 1T, but replacing the resultant compound of Example 1S with the resultant compound of Example 53D provided 0.28 g (43%) of the desired compound.

F. (2S,3S,5S)-5-(N-(N-((N-Methyl-N-((2-ethyl-4-thiazolyl)methyl)amino)carbonyl)valinyl)amino)-2-(N-((5thiazolyl)methoxycarbonyl)amino)-1,6-diphenyl-3-hydroxyhexane Using the procedure of Example 1U, but replacing N-((N-methyl-N-((2-isopropyl-4-thiazolyl)methyl)amino)carbonyl)-L-valine with N-((N-methyl-N-((2-ethyl-4-thiazolyl)methyl)amino)carbonyl)-L-valine provided, after purification by silica gel chromatography using 1% methanol in chloroform, 60 mg (40%) of the desired compound ($R_f$ 0.14, 95:5 $CH_2Cl_2$:$CH_3OH$) as a solid, mp 70°–71° C. Mass spectrum: $(M+H)^+$=707. Anal. Calcd for $C_{36}H_{46}N_6O_5S_2 \cdot H_2O$: C, 59.65; H, 6.67; N, 11.59. Found: C, 59.64; H, 6.59; N, 11.88.

EXAMPLE 54

A. 2-Isopropyl-4-(((N-(1-propyl))amino)methyl)thiazole

Using the procedure of Example 1Q, but replacing 40% aqueous methylamine with 1-aminopropane provided the crude desired compound. $^1H$ NMR ($CDCl_3$) δ0.94 (t, J=7 Hz, 3H), 1.39 (d, J=7 Hz, 6H), 1.54 (sextet, J=7 Hz, 2H), 2.62 (t, J=7 Hz, 2H), 3.30 (heptet, J=7 Hz, 1H), 3.87 (d, J=1 Hz, 2H), 6.93 (s, 1H). Mass spectrum: $(M+H)^+$=199.

B. N-((N-(1-Propyl)-N-((2-isooropyl-4-thiazolyl)methyl)amino)carbonyl)-L-valine Methyl Ester Using the procedure of Example 1S, but replacing 2-isopropyl-4-(((N-methyl)amino)methyl)thiazole with 2-isopropyl-4-(((N-(1-propyl))amino)methyl)thiazole provided, after silica gel chromatography using 1% methanol in chloroform as an eluent, 1.55 g (63%) of the desired compound. $^1H$ NMR ($CDCl_3$) δ0.86 (t, J=7 Hz, 3H), 1.38 (d, J=7 Hz, 6H), 1.41 (d, J=7 Hz, 6H), 1.56 (m, 1H), 1.57 (sextet, J=7 Hz, 2H), 3.27 (heptet, J=7 Hz, 1H), 3.29 (t, J=7 Hz, 2H), 3.71 (s, 3H), 4.45 (m, 3H), 6.31 (br, 1H), 6.98 (s, 1H). Mass spectrum: $(M+H)^+$=328.

C. N-((N-(1-Propyl)-N-((2-isopropyl-4-thiazolyl)methyl)amino)carbonyl)-L-valine Using the procedure of Example 1T, but replacing the resultant compound of Example 1S with the resultant compound of Example 54B provided the desired compound.

D. (2S,3S,5S)-5-(N-(N-((N-(1-Propyl)-N-((2-isopropyl-4-thiazolyl)methyl)amino)carbonyl)valinyl)amino)-2-(N-(5-thiazolyl)methoxycarbonyl)amino)-1,6-diphenyl-3-hydroxyhexane Using the procedure of Example 1U but replacing N-((N-methyl-N-((2-isopropyl-4-thiazolyl)methyl)amino)carbonyl)-L-valine with N-((N-(1-propyl)-N-((2-isopropyl-4-thiazolyl)methyl)amino)carbonyl)-L-valine provided, after silica gel chromatography using 1% methanol in chloroform, 60 mg (44%) of the desired compound ($R_f$ 0.3, 95:5 $CHCl_3$:$CH_3OH$) as a solid, mp 62°–64° C. Mass spectrum: $(M+H)^+$=721. Anal. Calcd for $C_{37}H_{48}N_6O_5S_2 \cdot 0.5H_2O$: C, 60.88; H, 6.77: N, 11.51. Found: C, 60.66; H, 6.95; N, 11.45

EXAMPLE 55

A. 2-Isopropyl-4-((N-isobutyl)amino)methyl)thiazole

Using the procedure of Example 1Q, but replacing 40% aqueous methylamine with isobutylamine provided the crude desired compound. Mass spectrum: $(M+H)^+$=213.

B. N-((N-(Isobutyl)-N-((2-isopropyl-4-thiazolyl)methyl)amino)carbonyl)-L-valine Methyl Ester Using the procedure of Example 1S, but replacing 2-isopropyl-4-(((N-methyl)amino)methyl)thiazole with 2-isopropyl-4-(((N-(isobutyl))amino)methyl)thiazole provided, after silica gel chromatography using 1% methanol in chloroform as an eluent, 0.7 g (41%) of the desired compound. $^1H$ NMR (DMSO-$d_6$) δ0.78 (d, J=7 Hz, 3H), 0.79 (d, J=7 Hz, 3H), 1.30 (m, 12H), 1.89 (m, 2H), 3.05 (d, J=8 Hz, 2H), 3.22 (m, 1H), 3.58 (s, 3H), 4.13 (m, 1H), 4.44 (AA', 2H), 6.87 (br d, 1H), 7.23 (s, 1H). Mass spectrum: $(M+H)^+$=3.42.

C. N-((N-(Isobutyl)-N-((2-isopropyl-4-thiazolyl)methyl)amino)carbonyl)-L-valine Using the procedure of Example 1T, but replacing the resultant compound of Example 1S with the resultant compound of Example 55B provided the desired compound.

D. (2S,3S,5S)-5-(N-(N-((N-(Isobutyl)-N-((2-isopropyl-4-thiazolyl)methyl)amino)carbonyl)valinyl)amino)-2-(N-((5-thiazolyl)methoxycarbonyl)amino)-1,6-diphenyl-3-hydroxyhexane Using the procedure of Example 1U but replacing N-((N-methyl-N-((2-isopropyl-4-thiazolyl)methyl)amino)carbonyl)-L-valine with N-((N-(isobutyl)-N-((2-isopropyl-4-thiazolyl)methyl)amino)carbonyl)-L-valine provided, after silica gel chromatography using 1% methanol in chloroform, 70 mg (50%) of the desired compound ($R_f$ 0.3, 5% methanol in chloroform) as a solid, mp 60°–61° C. Mass spectrum: $(M+H)+$=735. Anal. Calcd for $C_{38}H_{50}N_6O_5S_2$: C, 62.10; H, 6.86; N, 11.43; S, 8.72. Found: C, 61.74; H, 7.16; N, 11.36; S, 8.48.

EXAMPLE 56

A. N-((N-Methyl-N-((2-isopropyl-4-oxazolyl)methyl)amino)carbonyl)-L-alanine Methyl Ester Using the procedure of Example 1S, but replacing 2-isopropyl-4-(((N-methyl)amino)methyl)thiazole with 2-isopropyl-4-(((N-methyl)amino)methyl)-oxazole and relacing N-(((4-nitrophenyl)oxy)carbonyl)-L-valine methyl ester with N-(((4-nitrophenyl)oxy)carbonyl)-L-alanine methyl ester provided the desired compound in 66% yield. $^1$H NMR (CDCl$_3$) δ1.32 (d, 6H), 1.42 (d, 3H), 2.96 (s, 3H), 3.05 (m, 1H), 3.75 (s, 3H), 4.30 (s, 2H), 4.47 (m, 1H), 5.80 (br d, 1H), 7.46 (s, 1H). Mass spectrum: (M+H)$^+$=284.

B. N-((N-Methyl-N-((2-isopropyl-4-oxazolyl)methyl)amino)carbonyl)-L-alanine

Using the procedure of Example 1T, but replacing the resultant compound of Example 1S with the resultant compound of Example 56A provided the desired compound.

C. (2S,3S,5S)-5-(N-(N-((N-Methyl-N-((2-isopropyl-4-oxazolyl)methyl)amino)carbonyl)-L-alaninyl)amino)-2-(N-((5-thiazolyl)methoxycarbonyl)amino)-1,6-diphenyl-3-hydroxyhexane Using the procedure of Example 1U but replacing N-((N-methyl-N-((2-isopropyl-4-thiazolyl)methyl)amino)carbonyl)-L-valine with N-((N-methyl-N-((2-isopropyl-4-oxazolyl)methyl)amino)carbonyl)-L-alanine provided, after silica gel chromatography using 92:8 CH$_2$Cl$_2$:CH$_3$OH, the desired compound (R$_f$ 0.49, 92:8 CH$_2$Cl$_2$:CH$_3$OH) in 75% yield. Mass spectrum: (M+H)$^+$=677.

EXAMPLE 57

(2S,3S,5S)-5-(N-(N-((N-Methyl-N-((2-isopropyl-4-oxazolyl)methyl)amino)carbonyl)-L-alaninyl)amino)-2-(N-((5-isoxazolyl)methoxycarbonyl)amino)-1,6-diphenyl-3-hydroxyhexane Using the procedure of Example 1U but replacing N-((N-methyl-N-((2-isopropyl-4-thiazolyl)methyl)amino)carbonyl)-L-valine with N-((N-methyl-N-((2-isopropyl-4-oxazolyl)methyl)amino)carbonyl)-L-alanine and replacing (2S,3S,5S)-5-amino-2-(N-((5-thiazolyl)methoxycarbonyl)amino)-1,6-diphenyl-3-hydroxyhexane with (2S,3S,5S)-5-amino-2-(N-((5-isoxazolyl)methoxy-carbonyl)amino)-1,6-diphenyl-3-hydroxyhexane provided, after silica gel chromatography using 92:8 CH$_2$Cl$_2$:CH$_3$OH, the desired compound (R$_f$ 0.48, 92:8 CH$_2$Cl$_2$:CH$_3$OH) in 64% yield. $^1$H NMR (DMSO-d$_6$) δ1.08 (d, 3H), 1.24 (d, 6H), 1.50 (m, 2H), 2.82 (s, 3H), 3.0 (m, 1H), 4.25 (s, 2H), 4.60 (d, 1H), 5.05 (s, 2H), 6.20 (br d, 1H), 6.32 (d, 1H), 7.20 (m, 11H), 7.50 (br d, 1H), 7.78 (s, 1H), 8.51 (d, 1H). Mass spectrum: (M+H)$^+$=661.

EXAMPLE 58

A. Cyclopentanecarboxamide

Using the procedure of Example 44A but replacing 2-ethylbutyric acid with cyclopentanecarboxylic acid provided 2.6 g (100%) of the crude desired compound.

B. Cyclopentanethiocarboxamide

Using the procedure of Example 1O, but replacing isobutyramide with cyclopentanecarboxamide provided 2.4 g (83%) of the crude desired compound.

C. 4-(Chloromethyl)-2-cyclopentylthiazole hydrochloride

Using the procedure of Example 1P, but replacing 2-methylpropanethioamide with cyclopentanethiocarboxamide provided the crude desired compound as a yellow oil.

D. 2-Cyclopentyl-4-(((N-methyl)amino)methyl)thiazole

Using the procedure of Example 1Q, but replacing 4-(chloromethyl)-2-isopropylthiazole hydrochloride with 4-(chloromethyl)-2-cyclopentylthiazole hydrochloride provided, after purification of the residue by silica gel chromatography using 3% methanol in chloroform, 0.83 g (43%) of the desired compound.

E. N-((N-Methyl-N-((2-cyclopentyl-4-thiazolyl)methyl)amino)carbonyl)-L-valine Methyl Ester Using the procedure of Example 1S, but replacing 2-isopropyl-4-(((N-methyl)amino)-methyl)thiazole with 2-cyclopentyl-4-(((N-methyl)amino)methyl)-thiazole provided, after purification by silica gel chromatography using 1% methanol in chloroform as an eluent, 0.77 g (51%) of the desired compound. $^1$H NMR (CDCl$_3$) δ0.93 (d, J=7 Hz, 3H), 0.97 (d, J=7 Hz, 3H), 1.6–1.9 (m, 6H), 2.2 (m, 3H), 2.99 (s, 3H), 3.40 (m, 1H), 3.71 (s, 3H), 4.37 (dd, J=9, 5 Hz, 1H), 4.45 (AA', 2H), 5.99 (br d, 1H), 6.95 (s, 1H). Mass spectrum: (M+H)$^+$=354.

F. N-((N-Methyl-N-((2-cyclopentyl-4-thiazolyl)methyl)amino)carbonyl)-L-valine Using the procedure of Example 1T, but replacing the resultant compound of Example 1S with the resultant compound of Example 58E provided 0.64 g (87%) of the desired compound.

G. (2S,3S,5S)-5-(N-(N-((N-Methyl-N-((2-cyclopentyl-4-thiazolyl)methyl)amino)carbonyl)valinyl)amino)-2-(N-((5-thiazolyl)methoxycarbonyl)amino)-1,6-diphenyl-3-hydroxyhexane Using the procedure of Example 1U, but replacing N-((N-methyl-N-((2-isopropyl-4-thiazolyl)methyl)amino)carbonyl)-L-valine with N-((N-methyl-N-((2-cyclopentyl-4-thiazolyl)methyl)amino)carbonyl)-L-valine provided, after purification by silica gel chromatography using 1% methanol in chloroform, 50 mg (36%) of the desired compound (R$_f$ 0.40, 5% methanol in chloroform) as a solid, mp 70°–71° C. Mass spectrum: (M+H)$^+$=747. Anal. Calcd for C$_{39}$H$_{50}$N$_6$O$_5$S$_2$: C, 62.71; H, 6.75; N, 11.25. Found: C, 63.16; H, 6.80; N, 10.84.

EXAMPLE 59

A. 3-Methylbutanamide

Using the procedure of Example 44A but replacing 2-ethylbutyric acid with 3-methylbutyric acid provided 4.2 g (100%) of the crude desired compound.

B. 3Methylpropanethiocarboxamide

Using the procedure of Example 1O, but replacing isobutyramide with 3-methylbutanamide provided the crude desired compound.

C. 4-(Chloromethyl)-2-isobutylthiazole hydrochloride

Using the procedure of Example 1P, but replacing 2-methylpropanethioamide with 3-methylpropanethiocarboxamide provided the crude desired compound as a yellow oil.

D. 2-Isobutyl-4-(((N-methyl)amino)methyl)thiazole

Using the procedure of Example 1Q, but replacing 4-(chloromethyl)-2-isopropylthiazole hydrochloride with 4-(chloromethyl)-2-isobutylthiazole hydrochloride provided, after purification of the residue by silica gel chromatography using 10% methanol in chloroform, 0.61 g (31%) of the desired compound.

E. N-((N-Methyl-N-((2-isobutyl-4-thiazolyl)methyl)amino)carbonyl)-L-valine Methyl Ester Using the procedure of Example 1S, but replacing 2-isopropyl-4-(((N-methyl)amino)methyl)thiazole with 2-isobutyl-4-(((N-methyl)amino)methyl)thiazole provided, after purification by silica gel chromatography using 1% methanon in chloroform as an eluent, 0.40 g (32%) of the desired compound. Mass spectrum: $(M+H)^+=342$.

F. N-((N-Methyl-N-((2-isobutyl-4-thiazolyl)methyl)amino)carbonyl)-L-valine

Using the procedure of Example 1T, but replacing the resultant compound of Example 1S with the resultant compound of Example 59E provided 0.13 g (70%) of the desired compound.

G. (2S,3S,5S)-5-(N-(N-((N-Methyl-N-((2-isobutyl-4-thiazolyl)methyl)amino)carbonyl)valinyl)amino)-2-(N-((5-thiazolyl)methoxycarbonyl)amino)-1,6-diphenyl-3-hydroxyhexane Using the procedure of Example 1U, but replacing N-((N-methyl-N-((2-isopropyl-4-thiazolyl)methyl)amino)carbonyl)-L-valine with N-((N-methyl-N-((2-isobutyl-4-thiazolyl)methyl)amino)carbonyl)-L-valine provided, after purification by silica gel chromatography using 1% methanol in chloroform, 50 mg (33%) of the desired compound ($R_f$ 0.65, 10% methanol in chloroform). Mass spectrum: $(M+H)^+=735$.

EXAMPLE 60

A. 2-Cyclopentyl-4-(((N-ethyl)amino)methyl)thiazole

Using the procedure of Example 1Q, but replacing 4-(chloromethyl)-2-isopropylthiazole hydrochloride with 4-(chloromethyl)-2-cyclopentylthiazole hydrochloride and replacing 40% aqueous methylamine with 70% aqueous ethylamine provided, after purification of the residue by silica gel chromatography using 5% methanol in chloroform, 1.08 g (50%) of the desired compound.

B. N-((N-Ethyl-N-((2-cyclopentyl-4-thiazolyl)methyl)amino)carbonyl)-L-valine Methyl Ester Using the procedure of Example 1S, but replacing 2-isopropyl-4-(((N-methyl)amino)methyl)thiazole with 2-cyclopentyl-4-(((N-ethyl)amino)methyl)-thiazole provided, after purification by silica gel chromatography using 1% methanol in chloroform as an eluent, 0.40 g (46%) of the desired compound. $^{11}$H NMR (DMSO-d$_6$) $\delta 1.00$ (t, J=7Hz, 3H), 1.29 (d, J=7 Hz, 3H), 1.6–1.8 (m, 9H), 2.1 (m, 3H), 3.27 (m, 2H), 3.37 (m, 1H), 3.60 (s, 3H), 4.17 (pentet, J=7 Hz, 1H), 4.41 (AA', 2H), 6.80 (d, J=7 Hz, 1H), 7.20 (s, 1H). Mass spectrum: $(M+H)^+=340$.

C. N-((N-Ethyl-N-((2-cyclopentyl-4-thiazolyl)methyl)amino)carbonyl)-L-valine Using the procedure of Example 1T, but replacing the resultant compound of Example 1S with the resultant compound of Example 60B provided 0.13 g (69%) of the desired compound.

D. (2S,3S,5S)-5-(N-(N-((N-Ethyl-N-((2-cyclopentyl-4-thiazolyl)methyl)amino)carbonyl)valinyl)amino)-2-(N-((5-thiazolyl)methoxycarbonyl)amino)-1,6-diphenyl-3-hydroxyhexane Using the procedure of Example 1U, but replacing N-((N-methyl-N-((2-isopropyl-4-thiazolyl)methyl)amino)carbonyl)-L-valine with N-((N-ethyl-N-((2-cyclopentyl-4-thiazolyl)methyl)amino)carbonyl)-L-valine provided, after purification by silica gel chromatography using 1.5% methanol in chloroform, 50 mg (34%) of the desired compound ($R_f$ 0.63, 10% methanol in chloroform) as a solid, mp 67°–69° C. Mass spectrum: $(M+H)^+=733$. Anal. Calcd for $C_{38}H_{48}N_6O_5S_2$: C, 62.27; H, 6.60; N, 11.47. Found: C, 62.02; H, 6.74; N, 10.98.

EXAMPLE 61

A. 2-Isopropyl-4-(2-((N-methyl)amino)ethyl)thiazole

A solution of 2.0 g (12 mmol) of 2-isopropyl-4-(hydroxyethyl)thiazole in 50 ml of tetrahydrofuran was treated with 1.34 g (12 mmol) of methanesulfonyl chloride. The resulting solution was treated dropwise with 3.4 ml (24 mmol) of triethylamine and stirred at ambient temperature for 1 h. A portion (25 ml) of the resulting solution was added to 50 ml of aqueous ethylamine (70% in H$_2$O) with rapid stirring. After addition, the mixture was heated to reflux for 2 h, allowed to cool, diluted with ethyl acetate, washed with aqueous NaHCO$_3$ and saturated brine, dried over Na$_2$SO$_4$, and concentrated in vacuo to provide the crude desired compound. Purification of the residue by silica gel chromatography using 5% methanol in chloroform, 0.52 g (48%) of the desired compound. $^1$H NMR (CDCl$_3$) $\delta 1.38$ (d, J=7 Hz, 3H), 2.46 (s, 3H), 2.93 (s, 4H), 3.30 (heptet, J=7 Hz, 1H), 6.79 (s, 1H). Mass spectrum: $(M+H)^+=185$.

B. N-((N-Methyl-N-(2-(2-isopropyl-4-thiazolyl)ethyl)amino)carbonyl)-L-valine Methyl Ester Using the procedure of Example 1S, but replacing 2-isopropyl-4-(((N-methyl)amino)methyl)thiazole with 2-isopropyl-4-(2-((N-methyl)amino)ethyl)-thiazole provided, after purification by silica gel chromatography using 1% methanol in chloroform as an eluent, 0.16 g (35%) of the desired compound. $^{11}$H NMR (CDCl$_3$) $\delta 0.91$ (d, J=7 Hz, 3H), 0.98

(d, J=7 Hz, 3H), 1.48 (d, J=7 Hz, 3H), 1.49 (d, J=7 Hz, 3H), 2.11 (heptet of doublets, J=7, 5 Hz, 1H), 2.85 (s, 3H), 2.99 (t, J=7 Hz, 2H), 3.30 (heptet, J=7 Hz, 1H), 3.63 (t, J=7 Hz, 2H), 3.73 (s, 3H), 4.42 (dd, J=8, 5 Hz, 1H), 4.93 (br d, J=8 Hz, 1H), 6.83 (s, 1H). Mass spectrum: $(M+H)^+=342$.

C. N-((N-Methyl-N-(2-(2-isopropyl-4-thiazolyl)ethyl)amino)carbonyl)-L-valine Using the procedure of Example 1T, but replacing the resultant compound of Example 1S with the resultant compound of Example 61B provided 0.074 g (64%) of the desired compound.

D. (2S,3S,5S)-5-(N-(N-((N-Methyl-N-(2-(2-isopropyl-4-thiazolyl)ethyl)amino)carbonyl)valinyl)amino)-2-(N-((5-thiazolyl)methoxycarbonyl)amino)-1,6-diphenyl-3-hydroxyhexane Using the procedure of Example 1U, but replacing N-((N-methyl-N-((2-isopropyl-4-thiazolyl)methyl)amino)carbonyl)-L-valine with N-((N-methyl-N-(2-(2-isopropyl-4-thiazolyl)ethyl)amino)carbonyl)-L-valine provided, after purification by silica gel chromatography using 1% methanol in chloroform, 90 mg (54%) of the desired compound ($R_f$ 0.44, 10% methanol in chloroform) as a solid, mp 62°–63° C. Mass spectrum: $(M+H)^+=735$. Anal. Calcd for $C_{38}H_{50}N_6O_5S_2$: C, 62.10; H, 6.86; N, 11.43; S, 8.72. Found: C, 61.72; H, 6.78;, N, 11.34; S, 8.89.

EXAMPLE 62

A. 2-Isopropyl-4-((N-(tert-butyloxycarbonylamino)amino)methyl)thiazole

A solution of 7.5 g (57 mmol) to t-butylcarbazate in 200 ml of isopropyl alcohol was treated with a solution of 1.0 g (57 mmol) of 4-(chloromethyl)-2-isopropylthiazole hydrochloride in 10 ml of isopropyl alcohol. The resulting solution was heated at reflux for 16 h, allowed to cool, and concentrated in vacuo. The residue was diluted with 1N HCl, washed with three portions of ethyl acetate, basified to pH 12 with aqueous NaOH, and extracted with three portion of ethyl acetate. The combined organic layers were dried over $MgSO_4$ and concentrated in vacuo. Purification of the residue by silica gel chromatography using 20% ethyl acetate in hexane provided 0.32 g (21%) of the desired compound ($R_f$ 0.4, 5% methanol in chloroform). $^1H$ NMR (CDCl$_3$) δ1.40 (d, J=7 Hz, 6H), 1.47 (s, 9H), 2.53 (br, 1H), 3.33 (heptet, J= 7 Hz, 1H), 4.11 (s, 2H), 6.22 (br, 1H), 7.01 (s, 1H). Mass spectrum: $(M+H)^+=272$.

B. N-((N-(tert-Butyloxycarbonylamino)-N-((2-isopropyl-4-thiazolyl)methyl)amino)carbonyl)-L-valine Methyl Ester Using the procedure of Example 1S, but replacing 2-isopropyl-4-(((N-methyl)amino)methyl)thiazole with 2-isopropyl-4-((N-(tert-butyloxycarbonylamino)amino)methyl)thiazole provided, after silica gel chromatography using 1% methanol in chloroform as an eluent, 0.30 g (95%) of the desired compound. $^1H$ NMR (DMSO-d$_6$) δ0.84 (d, J=7 Hz, 3H), 0.87 (d, J=7 Hz, 3H), 1.31 (d, J=7 Hz, 6H), 1.39 (s, 9H), 2.05 (m, 1H), 3.24 (m, 1H), 3.64 (s, 3H), 4.09 (dd, J=9, 6 Hz, 1H), 6.35 (br, 1H), 7.24 (s, 1H). Mass spectrum: $(M+H)^+=429$.

C. N-((N-(tert-Butyloxycarbonylamino)-N-((2-isopropyl-4-thiazolyl)methyl)amino)carbonyl)-L-valine Using the procedure of Example 1T, but replacing the resultant compound of Example 1S with the resultant compound of Example 62B provided the desired compound.

D. (2S,3S,5S)-5-(N-(N-((N-(tert-Butyloxycarbonylamino)-N-((2-isopropyl-4-thiazolyl)methyl)amino)carbonyl)valinyl)amino)-2-(N-((5-thiazolyl)methoxycarbonyl)amino)-1,6-diphenyl-3-hydroxyhexane Using the procedure of Example 1U but replacing N-((N-methyl-N-((2-isopropyl-4-thiazolyl)methyl)amino)carbonyl)-L-valine with N-((N-(tert-butyloxycarbonylamino)-N-((2-isopropyl-4-thiazolyl)methyl)amino)carbonyl)-L-valine provided, after silica gel chromatography using 1% methanol in chloroform, 80 mg (41%) of the desired compound ($R_f$ 0.35, 5% methanol in chloroform). Mass spectrum: $(M+H)^+=822$. HRMS. Exact mass calcd for $C_{41}H_{56}N_7O_7S_2$: 822.3683. Found: 822.3682.

EXAMPLE 63

(2S,3S,5S)-5-(N-(N-((N-(Amino)-N-((2-isopropyl-4-thiazolyl)methyl)amino)carbonyl)valinyl)amino)-2-(N-((5-thiazolyl)methoxycarbonyl)amino)-1,6-diphenyl-3-hydroxyhexane Hydrochloride To 60 mg (0.073 mmol) of (2S,3S,5S)-5-(N-(N-((N-(tert-butyloxycarbonyl-amino)-N-((2-isopropyl-4-thiazolyl)methyl)amino)carbonyl)valinyl)amino)-2-(N-((5-thiazolyl)methoxycarbonyl)amino)-1,6-diphenyl-3-hydroxyhexane was added 5 ml of 4M HCl in dioxane. The resulting solution was stirred at ambient temperature for 2 h. After concentration of the solution in vacuo, the residue was taken up in 0.5 ml of methanol, added to 20 ml of diethyl ether, and filtered to provide 40 mg (77%) of the desired compound ($R_f$ 0.60, 10% methanol in chloroform). Mass spectrum: $(M+H)^+=722$.

EXAMPLE 64

(2S,3S,5S)-5-(N-(N-((2-Isopropyl-4-thiazolyl)methoxycarbonyl)valinyl)amino)-1-phenyl-2-(N-((5-thiazolyl)methoxycarbonyl)amino)-6-(5-thiazolyl)-3-hydroxyhexane Using the procedure of Example 1U but replacing (2S, 3S,5S)-5-amino-2-(N-((5-thiazolyl)methoxycarbonyl)amino)-1,6-diphenyl-3-hydroxyhexane with (2S,3S,5S)-5-amino-1-phenyl-2-(N-((5-thiazolyl)methoxycarbonyl)amino)-6-(5-thiazolyl)-3-hydroxyhexane and replacing N-((N-methyl-N-((2-isopropyl-4-thiazolyl)methyl)amino)carbonyl)-L-valine with N-((2-isopropyl-4-thiazolyl)methoxycarbonyl)valine provided, after silica gel chromatography using 10% methanol in dichloromethane, 25 mg (76%) of the desired compound ($R_f$ 0.47, 10% methanol in dichloromethane). Mass spectrum: $(M+H)^+=715$.

EXAMPLE 65

A. (2S,3S,5S)-3-(tert-Butyldimethylsilyloxy)-2-(tert-butyloxycarbonylamino)-1-phenyl-5-(N-((5-thiazolyl)methoxycarbonyl)amino)-6-(5-thiazolyl)hexane Using the procedure of Example 8F, but replacing benzyl alcohol with 5-(hydroxymethyl)thiazole provided, after silica gel chromatography using 10% methanol in dichloromethane, 261 mg (67%) of the desired compound. $^1$H NMR (CDCl$_3$) δ0.05 (s, 6H), 0.91 (s, 9H), 1.34 (s, 9H), 1.70 (m, 2H), 2.72 (m, 2H), 3.03 (m, 2H), 3.74 (m, 1H), 3.91 (m, 1H), 4.02 (m, 1H), 4.63 (br d, 1H), 5.24 (s, 2H), 7.19–7.35 (m, 5H), 7.52 (s, 1H), 7.86 (s, 1H), 8.66 (s, 1H), 8.79 (s, 1H). Mass spectrum: (M+H)$^+$=647.

B. (2S,3S,5S)-2-(tert-Butyloxycarbonylamino)-1-phenyl-5-(N-((5-thiazolyl)methoxycarbonyl)amino)-6-(5-thiazolyl)-3-hydroxyhexane Using the procedure of Example 8G, but replacing the resultant compound of Example 8F with the resultant compound of Example 65A provided, after silica gel chromatography using 10% methanol in dichloromethane, 74 mg (35%) of the desired compound. $^1$H NMR (CDCl$_3$) δ1.39 (s, 9H), 1.65 (m, 2H), 2.87 (m, 2H), 3.09 (m, 2H), 3.68 (m, 2H), 3.96 (m, 2H), 4.74 (br d, 1H), 5.26 (dd, 2H), 7.17–7.32 (m, 5H), 7.52 (s, 1H), 7.86 (s, 1H), 8.66 (s, 1H), 8.81 (s, 1H). Mass spectrum: (M+H)$^+$=533.

C. (2S,3S,5S)-2-Amino-1-phenyl-5-(N-((5-thiazolyl)methoxycarbonyl)amino)-6-(5-thiazolyl)-3-hydroxyhexane A solution of 70 mg (0.13 mmol) of the resultant compound of Example 65B in 2.1 ml of CH$_2$Cl$_2$ was treated with 0.7 ml of trifluoroacetic acid, stirred for 1.5 h, and concentrated in vacuo. The residue was treated with 3 ml of aqueous NaHCO$_3$, extracted with three portions of 95:5 CH$_2$Cl$_2$:CHCl$_3$, dried over Na$_2$SO$_4$, and concentrated in vacuo to provide 55 mg (97%) of the desired compound as a white foamy solid. $^1$H NMR (CDCl$_3$) δ1.72 (m, 2H), 1.86 (br, 2H), 2.46 (dd, 1H), 2.84 (m, 2H), 3.20 (m, 2H), 3.45 (m, 1H), 4.02 (m, 1H), 5.30 (dd, 2H), 5.52 (br d, 1H), 7.14–7.34 (m, 5H), 7.59 (s, 1H), 7.88 (s, 1H), 8.67 (s, 1H), 8.80 (s, H). Mass spectrum: (M+H)$^+$=433.

D. (2S,3S,5S)-2-(N-(N-((2-Isopropyl-4-thiazolyl)methoxycarbonyl)valinyl)amino)-1-phenyl-5-(N-((5-thiazolyl)methoxycarbonyl)amino)-6-(5-thiazolyl)-3-hydroxyhexane Using the procedure of Example 1U but replacing N-((N-methyl-N-((2-isopropyl-4-thiazolyl)methyl)amino)carbonyl)-L-valine with N-((2-isopropyl-4-thiazolyl)methoxycarbonyl)valine and replacing (2S,3S,5S)-5-amino-2-(N-((5-thiazolyl)methoxycarbonyl)amino)-1,6-diphenyl-3-hydroxyhexane with (2S,3S,5S)-2-amino-1-phenyl-5-(N-((5-thiazolyl)methoxycarbonyl)amino)-6-(5-thiazolyl)-3-hydroxyhexane provided, after silica gel chromatography using 1% methanol in chloroform, 54 mg (66%) of the desired compound (R$_f$ 0.6, 10% methanol in CH$_2$Cl$_2$). $^1$H NMR (DMSO-d$_6$) δ0.69 (d, 3H), 0.74 (d, 3H), 1.31 (d, 6H), 1.47 (m, 2H), 1.85 (m, 1H), 2.75 (m, 4H), 2.95 (m, 1H), 3.57 (m, 1H), 3.80 (m, 2H), 4.08 (m, 1H), 4.95 (d, 1H), 5.03 (s, 2H), 5.19 (s, 2H), 7.12–7.29 (m), 7.45 (s, 1H), 7.47 (s, 1H). Mass spectrum: (M+H)$^+$=715.

EXAMPLE 66

(2S,3S,5S)-2,5-Diamino-3-hydroxy-1,6-diphenylhexane dihydrochloride

EXAMPLE 66A (L)-N,N-Dibenzylphenylalanine benzyl ester

A solution containing L-phenylalanine (11 kg, 66.7 moles), potassium carbonate (29 kg, 210 moles), and water (66 L), and benzyl chloride (27 kg, 213 moles) was heated to 90°±15° C. for 10–24 hours. The reaction mixture was cooled to room temperature and heptane (29 L) and tap water (27 L) was added. The layers were separated and the organics washed one to two times with 22 L of a methanol/water solution (1/2 v/v). The organics were then stripped to give the desired product as an oil. IR (neat) 3090, 3050, 3030, 1730, 1495, 1450, 1160 cm$^{-1}$, $^1$H NMR (300 MHz, CDCl$_3$) δ7.5–7.0 (m, 20H), 5.3 (d, 1H, J=13.5 Hz), 5.2 (d, 1H, J=13.5 Hz), 4.0 (d, 2H, J=15 Hz), 3.8 (t, 2H, J=8.4 Hz), 3.6 (d, 2H, J=15 Hz), 3.2 (dd, 1H, J=8.4, 14.4 Hz), $^{13}$C NMR (300 MHz, CDCl$_3$) δ172.0, 139.2, 138.0, 135.9, 129.4, 128.6, 128.5, 128.4, 128.2, 128.1, 128.1, 126.9, 126.2, 66.0, 62.3, 54.3, 35.6. [α]$_D$ −79° (C=0.9, DMF).

EXAMPLE 66B (4S)-4-(N,N-Dibenzylamino)-3-oxo-5-phenyl-pentanonitrile

A solution containing the product of Example 66A (i.e., benzyl ester) (approx. 0.45 moles) in 520 mL tetrahydrofuran and 420 mL acetonitrile was cooled to −40° C. under nitrogen. A second solution containing sodium amide (48.7g, 1.25 moles) in 850 mL tetrahydrofuran was cooled to −40° C. To the sodium amide solution was slowly added 75 mL acetonitrile and the resulting solution was stirred at −40° C. for more than 15 minutes. The sodium amide/acetonitrile solution was then slowly added to the benzyl ester solution at −40° C. The combined solution was stirred at −40° C. for one hour and then quenched with 1150 mL of a 25% (w/v) citric acid solution. The resulting slurry was warmed to ambient temperature and the organics separated. The organics were then washed with 350 mL of a 25% (w/v) sodium chloride solution, then diluted with 900 mL heptane. The organics were then washed three times with 900 mL of a 5% (w/v) sodium chloride solution, two times with 900 mL of a 10% methanolic water solution, one time with 900 mL of a 15% methanolic water solution, and then one time with 900 mL of a 20% methanolic water solution. The organic solvent was removed in vacuo and the resulting material dissolved into 700 mL of hot ethanol. Upon cooling to room temperature, the desired product precipitated. Filtration gave the desired product in 59% yield from the L-phenylalanine. IR (CHCl$_3$) 3090, 3050, 3030, 2250, 1735, 1600, 1490, 1450, 1370, 1300, 1215 cm$^{-1}$, $^1$H NMR (CDCl$_3$) δ7.3 (m, 15H), 3.9 (d, 1H, J=19.5 Hz), 3.8 (d, 2H, J=13.5 Hz), 3.6 (d, 2H, J=13.5 Hz), 3.5 (dd, 1H, J=4.0, 10.5 Hz), 3.2 (dd, 1H, J=10.5, 13.5 Hz), 3.0 (dd, 1H, J=4.0, 13.5 Hz), 3.0 (d, 1H, J=19.5 Hz), $^{13}$C NMR (300 MHz, CDCl$_3$) δ197.0, 138.4, 138.0, 129.5, 129.0, 128.8, 128.6, 127.8, 126.4, 68.6, 54.8, 30.0, 28.4. [α]$_D$ −95° (C=0.5, DMF).

Alternate preparation of (4S)-4-(N,N-Dibenzylamino)-3-oxo-5-phenylpentanonitrile To a flask was charged sodium amide (5.8 g, 134 mmol) under nitrogen followed by 100 mL of methyl t-butyl ether (MTBE). The stirred solution was cooled to 0° C. Acetonitrile (8.6 mL, 165 mmol) was added over 1 minute. This solution was stirred at 5°±5° C. for 30 minutes. A solution of (L)-N,N-dibenzylphenylalanine benzyl ester (25 g, 90% pure, 51.6 mmol) in 125 mL of MTBE was added over 15 minutes and the resulting heterogeneous mixture was stirred at 5°±5° C. until the reaction was complete (approx. 3 hours). The reaction was quenched with 100 mL of 25% w/v aqueous citric acid and warmed to 25° C. before separating the layers. The organics were then washed with 100 mL of H$_2$O. The aqueous layer was separated and the organics filtered and concentrated in vacuo. The residue was crystallized from 50 mL of ethanol to afford 13.8 g of the desired product as a white solid.

EXAMPLE 66D (5S)-2-Amino-5-(N,N-dibenzylamino)-4-oxo-1,6-diphenylhex-2-ene

To a 5° C. solution of the product of Example 66B (20 Kg, 29 moles) in 29 L tetrahydrofuran was added benzylmagnesium chloride (45 Kg, 2M in THF, 84.5 moles). The solution was warmed to ambient temperature and stirred until analysis showed no starting material. The solution was then recooled to 5° C. and 54 L of a 15% citric acid solution was slowly added to quench excess benzylmagnesium chloride. The organics were separated and washed with 27 L 10% sodium chloride and stripped to a solid. The product was stripped again from 27 L ethanol (200 proof) and then dissolved in 67 L hot ethanol (200 proof). After cooling to room temperature and stirring for 12 hours, the resulting product was filtered and dried in a vacuum oven at 30° C. to give 24 kg of the desired product. mp 101°–102° C., IR (CDCl$_3$) 3630, 3500, 3110, 3060, 3030, 2230, 1620, 1595, 1520, 1495, 1450 cm$^{-1}$, $^1$H NMR (300 MHZ, CDCl$_3$) d 9.8 (br s, 1H), 7.2 (m, 20H), 5.1 (s, 1H), 4.9 (br s, 1H), 3.8 (d, 2H, J=14.7 Hz), 3.6 (d, 2H, J=14.7 Hz), 3.5 (m, 3H), 3.2 (dd, 1H, J=7.5, 14.4 Hz), 3.0 (dd, 1H, J=6.6, 14.4 Hz), $^{13}$C NMR (CDCl$_3$) d 198.0, 162.8, 140.2, 140.1, 136.0, 129.5, 129.3, 128.9, 128.7, 128.1, 128.0, 127.3, 126.7, 125.6, 96.9, 66.5, 54.3, 42.3, 32.4. [α]$_D$ –147° (c=0.5, DMF).

EXAMPLE 66E (2S,3S,5S)-5-Amino-2-(N,N-dibenzylamino)-3-hydroxy-1,6-diphenylhexane (i). A suspension of sodium borohydride (6.6 kg, 175 moles) in tetrahydrofuran (157 L) was cooled to less than –10°±5° C. Methanesulfonic acid (41.6 kg, 433 moles) was slowly added and the temperature kept below 0° C. during the addition. Once the addition was complete, a solution of water (6 L, 333 moles), the product of Example 66D (20 kg, 43 moles) and tetrahydrofuran (61 L) was slowly added while maintaining the temperature below 0° C. during the addition. The mixture was stirred for not less than 19 h at 0°±5° C.

(ii). To a separate flask was added sodium borohydride (6.6 kg, 175 moles) and tetrahydrofuran (157 L). After cooling to –5°±5° C., trifluoroacetic acid (24.8 kg, 218 moles) was added while maintaining the temperature below 15° C. The solution was stirred 30 min at 15°±5° C. and was then added to the reaction mixture resulting from step (i), keeping the temperature at less than 20° C. This was stirred at 20°±5° C. until reaction was complete. The solution was then cooled to 10°±5° C. and quenched with 3N NaOH (195 kg). After agitating with tert-butyl methyl ether (162 L), the organic layer was separated and washed one time with 0.5 N NaOH (200 kg), one time with 20% w/v aqueous ammonium chloride (195 kg), and two times with 25% aqueous sodium chloride (160 kg). The organics were stripped to give the desired product as an oil which was used directly in the next step.

IR (CHCl$_3$) 3510, 3400, 3110, 3060, 3030, 1630, $^1$H NMR (300 MHz, CDCl$_3$) δ7.2 (m, 20H), 4.1 (d, 2H, J=13.5 Hz), 3.65 (m, 1H), 3.5 (d, 2H, J=13.5 Hz), 3.1 (m, 2H), 2.8 (m, 1H), 2.65 (m, 3H), 1.55 (m, 1H), 1.30 (m, 1H), $^{13}$C NMR (300 MHz, CDCl$_3$) δ140.8, 140.1, 138.2, 129.4, 129.4, 128.6, 128.4, 128.3, 128.2, 126.8, 126.3, 125.7, 72.0, 63.6, 54.9, 53.3, 46.2, 40.1, 30.2.

EXAMPLE 66F (2S,3S,5S)-2,5-Diamino-3-hydroxy-1,6-diphenylhexane Dihydrochloride To a stirred solution of [2S,3S,5S]-2-(N,N-dibenzylamino)-3-hydroxy-5-amino-1,6-diphenylhexane (20 kg, 43.1 mol) in methanol (250 kg) was added an aqueous solution of ammonium formate (13.6 kg, 215 mol) in water (23 kg) and an aqueous suspension of 5% wet palladium on carbon (4.0 kg, Degussa catalyst, E101 NE/W, approximately 50–60% water by weight). The suspension which resulted was heated to reflux (70±10° C.) for 6 hours and then cooled to room temperature. The suspension was filtered through a bed of diatomaceous earth and the cake was washed with methanol (2×30 kg). The filtrate was concentrated via vacuum distillation to an aqueous oil. The aqueous residue was taken up in 1N NaOH (200 liters) and extracted with ethyl acetate (155 kg). The organic product layer was washed with a 20% aqueous sodium chloride solution (194 kg) and then with water (97 kg). The ethyl acetate product solution was then concentrated to an oil under vacuum distillation. Isopropanol (40 kg) was then charged to the residue and again the solution was concentrated to an oil with vacuum distillation. To the oil was charged isopropanol (160 kg) and concentrated aqueous hydrochloric acid (20.0 kg). The suspension/solution was then heated to reflux for 1 hour and then slowly cooled to room temperature. The slurry was then stirred for 12–16 hours. The slurry was filtered and the cake was washed with ethyl acetate (30 kg). The wet cake was resuspended in isopropanol (93 kg) and water (6.25 kg) and heated to reflux for 1 hour with stirring. The reaction mixture was then slowly cooled to room temperature and stirred for 12–16 hours. The reaction mixture was filtered and the wet cake was washed with isopropanol (12 kg). The solid was dried in a vacuum oven at 45° C. for approximately 24 hours to provide 7.5 kg of the desired product. $^1$H NMR (300 MHz, CD$_3$OD) δ7.40–7.15 (m, 10H), 3.8 (ddd, 1H, J=11.4, 3.7, 3.7 Hz), 3.68–3.58 (m, 1H), 3.37 (ddd, 1H, J=7.5, 7.5, 3.5 Hz), 3.05–2.80 (m, 4H), 1.95–1.70 (m, 2H), $^{13}$C NMR (300 MHz, CD$_3$OD) δ135.3, 135.1, 129.0, 128.9,128.7, 128.7, 127.12, 127.07, 67.4, 57.1, 51.6, 38.4, 35.5, 35.2.

EXAMPLE 67

(2S,3S,5S)-2-Amino-3-hydroxy-5-(t-butyloxycarbonylamino)-1,6-diphenylhexane

EXAMPLE 67A (2S,3S,5S)-2-(N,N-dibenzylamino)-3-hydroxy-5-(t-butyloxycarbonylamino)-1,6-diphenylhexane To a stirred solution of (2S,3S,5S)-2-(N,N-dibenzylamino)-3-hydroxy-5-amino-1,6-diphenylhexane (10.0 g, 21.6 mmol) in tetrahydrofuran (200 mL) was added potassium carbonate (6.0 g, 43.2 mmol) in H$_2$O (200 mL). To this solution was added di-t-butyldicarbonate (5.64 g, 25.9 mmol) in tetrahydrofuran (10 mL). The solution which resulted was stirred at room temperature for 3 hours. N,N-dimethylethylenediamine (1 mL, 8.6 mmol) was added and the reaction mixture was stirred at room temperature for an additional hour. Ethyl acetate (400 mL) was added and the organic layer was separated and washed with 5% KH$_2$PO$_4$ (2'200 mL), water (1'200 mL), saturated NaHCO$_3$ (2×200 mL) and water (1×200 mL). The organic solution was then dried over sodium sulfate and concentrated under reduced pressure to provide the desired product as a light yellow oil. 300 MHz $^1$H NMR (CDCl$_3$) δ1.40 (s,9H), 1.58 (s, 2H), 2.45–2.85 (m, 4H), 3.05 (m, 1H), 3.38 (d, 2H), 3.6 (m, 1H), 3.79 (m, 1H), 3.87 (d, 2H), 4.35 (s, 1H), 4.85 (s, broad, 1H), 7.0–7.38 (m, 20H).

EXAMPLE 67B (2S,3S,5S)-2-amino-3-hydroxy-5-(t-butyloxycarbonylamino)-1,6-diphenylhexane To a stirred solution of (2S,3S,5S)-2-(N,N-dibenzylamino)-3-hydroxy-5-(t-butyloxycarbonylamino)-1,6-diphenylhexane (12 g, 21.3 mmol) in methanol (350 mL) was charged ammonium formate (8.05 g, 128 mmol, 6.0 eq) and 10% palladium on carbon (2.4 g). The solution was stirred under nitrogen at 60° C. for three hours and then at 75° C. for 12 hours. An additional amount of ammonium formate (6 g) and 10% palladium on carbon (1.5 g) was added as well as 1 mL of glacial acetic acid. The reaction was driven to completion within 2 hours at a reflux temperature. The reaction mixture was then cooled to room temperature and then filtered through a bed of celite. The filter cake was washed with methanol (75 mL) and the combined filtrates were concentrated under reduced pressure. The residue was taken up in 1N NaOH (300 mL) and extracted into methylene chloride (2×200 mL). The combined organic layers were washed with brine (250 mL) and dried over sodium sulfate. Concentration of the solution under reduced pressure provided the desired product as a light colored oil which slowly crystallized upon standing (5 g). Further purification of the product could be accomplished by flash chromatography (silica gel, 5% methanol in methylene chloride). 300 MHz $^1$H NMR (CDCl$_3$) δ1.42 (s, 9H), 1.58 (m, 1H), 1.70 (m, 1H), 2.20 (s, broad, 2H), 2.52 (m, 1H), 2.76–2.95 (m, 4H), 3.50 (m, 1H), 3.95 (m, 1H), 4.80 (d, broad, 1H), 7.15–7.30 (m, 10H).

EXAMPLE 68

Alternative Preparation of (2S,3S,5S)-2-Amino-3-hydroxy-5-(t-butyloxycarbonylamino)-1,6-diphenylhexane

EXAMPLE 68A (5S)-2-(t-Butyloxycarbonylamino)-5-(N,N-dibenzylamino)-1,6-diphenyl-4-oxo-2-hexene To 9.21 gm (20 mmol) of the resultant compound of Example 66D and 0.37 gm (3 mmol) 4-N,N-dimethylaminopyridine in 100 ml of methyl tert-butylether butylether was added via syringe pump a solution containing 4.80 gm (22 mmol) di-tert-butyl dicarbonate in the same solvent (25 ml) over a period of 6 h. An additional amount (3 ml) of methyl tert-butylether was then added to complete the addition. After stirring at room temperature for 18 h the reaction mixture was cooled with the aid of an ice water bath. The resultant solid was collected by suction filtration and washed with cold (0° C.) methyl tert-butylether and hexane and dried under vacuum to give 9.9 gm of crude material as a white solid. The material thus isolated was disolved in a minimal amount of dichloromethane and purified by flash chromatography on silica gel. Elution of the column with a mixture of hexane-ethyl acetate-dichloromethane (8:1:1) gave, after concentration of the appropriate fractions, 8.1 gm (72%) of the desired compound. Mp. 191°–193° C. [α]$_D$ –183.7° (C=1.05, CHCl$_3$). $^1$H NMR (CDCl$_3$, δ): 11.68 (bs, 1H), 7.05–7.47 (m, 20H), 5.28 (s, 1H), 4.27 (d, J=16 Hz, 1H), 4.02 (d, J=16Hz, 1H), 3.58 (m, 4H), 3.40 (m, 1H), 3.11 (m, 1H), 2.90 (m, 1H), 1.48 (s, 9H).

EXAMPLE 68B

Alternate preparation of (5S)-2-(t-Butyloxycarbonylamino)-5-(N,N-dibenzylamino)-1,6-diphenyl-4-oxo-2-hexene A suspension of (S)-2-amino-5-(N,N-dibenzylamino)-1,6-diphenyl-4-oxo-2-hexene (100.0 g, 0.217 mol) in 15% ethyl acetate/hexanes (2 liters) under N$_2$ was warmed to about 40° C. The resulting solution was cooled to room temperature before adding 4.0 g (33 mmol) of N,N-dimethyl-4-aminopyridine and 49.7 g (0.228 mol) of di-tert-butyl dicarbonate. The reaction mixture was allowed to stir overnight at room temperature. (After approximately one hour, a white precipitate began to form.) The suspension was filtered and the precipitate was washed with hexanes to afford the desired product as colorless crystals. TLC: 25% ethyl acetate/hexanes R$_f$ 0.38.

EXAMPLE 68C (2S,3S,5S)-2-(N,N-Dibenzylamino)-5-(t-butyloxycarbonylamino)-3-hydroxy-1,6-diphenylhexane A solution of the product of Example 68A (5 g, 8.9 mmol) in dichloromethane (100 ml) and 1,4-dioxolane (100 ml) was cooled to between –10° and –15° C. and treated dropwise with 1M BH$_3$THF (26.7ml, 26.7mmol). The solution was stirred at this temperature for 3 hr. The clear solution was quenched with excess methanol (20 ml) and stirred at room temperature for 30 min. The solvent was removed in vacuo.

The resulting white foam was dissolved in THF (75 ml) and cooled to –40° C. A solution of LAH (9 ml, 1M in THF, 9 mmol) was added dropwise. After 10 min. the solution was quenched with water followed by dilute aqueous HCl. The organics were removed and the aqueous layer extracted with ethyl acetate (3×20 ml). The combined organics were washed (saturated aqueous bicarbonate followed by brine), dried (Na$_2$SO$_4$), filtered and evaporated to afford 4.9 g (99%) of the desired product as a white foam.

Alternatively, the white foam resulting from the BH$_3$THF reaction step was dissolved in MeOH (45 ml), cooled to +3° C. and treated portionwise with KBH$_4$ (1.44 g, 26.7 mmol). After addition of the last portion of KBH$_4$ the reaction was stirred for an additional 4 hours at +4° to +5° C. The solution was concentrated by 1/2 the volume in vacuo, diluted with 1/1 hexane-EtOAc (70 ml) and quenched (with cooling, maintain temp. <30° C.) by adding a 10% solution of KHSO$_4$ to pH=about 5. NaOH (15% aqueous) was added to pH=12–13. The insoluble salts were removed by filtration, and the filter cake washed 3 times with 7 ml 1/1 hexane/EtOAc. The filtrate and washes were transferred to a separatory funnel, diluted with 15 ml hexane and 15 ml H$_2$O. The organics were removed and the aqueous layer was extracted once with 20 ml (1/1) hexane-EtOAc. The combined organics were washed (saturated brine), dried (Na$_2$SO$_4$), filtered, and evaporated to afford 5.2 g of the desired product which was used without further purification in subsequent reactions.

R$_f$ 0.5 (25% EtOAc/hexane) $^1$H NMR (CDCl$_3$) δ7.37–7.10 (m 20H); 6.78 (br. s, 1H); 4.62 (d, 1H); 4.50 (s, 1H); 4.18 (dd, 1H); 3.9 (d, 2H); 3.65 (dd, 2H); 3.40 (d, 2H); 3.00 (m, 2H); 2.77 (m, 1H);1.39 (s, 9H). MS (EI) m/e565 (M+H).

EXAMPLE 68D (2S,3S,5S)-2-Amino-3-hydroxy-5-(t-butyloxycarbonylamino)-1,6-diphenylhexane A solution of the product from Example 68C (150 gm, 250 mmol) dissolved in absolute EtOH (2 liters) was treated with 10% Pd/C (18 gm, pre-wetted), followed by addition of ammonium formate (78.6 gms, 1.25 moles) dissolved in H$_2$O (200 ml). The resulting mixture was stirred at reflux for 2.5 hours. The mixture was cooled to room temperature and filtered through a pad of infusorial earth (20 g). The filter cake was washed 3 times with EtOH (70 ml each). The filtrate was concentrated in vacuo. The residue was dissolved into EtOAc (1 L) and washed (1N NaOH, followed by H$_2$O, followed by brine), dried (Na$_2$SO$_4$), filtered and concentrated in vacuo, to a constant weight of 95 gms. (99.2% of theory). The light yellow solid (91.5 gm of the 95 gm) was slurried in hot heptane (600 ml) (steam bath) and treated with isopropanol (45 ml), and swirled to effect solution. The solution was allowed to slowly cool to room temperature over 3 hours, kept at room temperature for 2 more hours and filtered. The filter cake was washed 10 times with 9/1 hexane-isopropanol (30 ml each) to give the desired product as an off-white finely crystalline solid which was dried to constant weight of 57.5 gm.

The crude product (20 gm) was recrystallized from hot 140 ml heptane/17 ml isopropanol. After letting the solution cool slowly to room temperature, the mixture was let stand at room temperature for 2 hours and then filtered. The filter cake was rinsed (5×15 ml (8/1) heptane/isopropanol) and dried to a constant weight of 18.5 gm.

EXAMPLE 69

Alternative Preparation of (2S,3S,5S)-5-(N-(N-((N-Methyl-N-((2-isopropyl-4-thiazolyl)methyl)amino)carbonyl)valinyl)amino)-2-(N-((5-thiazolyl)methoxycarbonyl)amino)-1,6-diphenyl-3-hydroxyhexane

EXAMPLE 69A (2S,3S,5S)-5-(t-Butyloxycarbonylamino)-2-(N-((5-thiazolyl)methoxycarbonyl)amino)-1,6-diphenyl-3-hydroxyhexane The product of Example 68D (6.0 g, 15.6 mmoles) was dissolved in 60 mL of DMF under nitrogen atmosphere. To this stirred solution at room temperature was added 5-(p-nitrophenyloxycarbonyloxymethyl)thiazole (4.67g, 15.6 mmole) and the resulting solution was stirred for 4 h. The solvent was removed under reduced pressure by rotary evaporation and the residue dissolved in 150 mL EtOAc. This solution was washed with 5×75 mL 1N NaoH solution, 100 mL brine, dried over Na$_2$SO$_4$. The solvent was removed to afford 8.02 g of a sligthly yellowish oil. This material was crystallized from 30 mL EtOAc and 40 mL hexane to afford 6.53 g (80%) of the desired product as a white solid. mp 118°–120° C. H $^1$NMR (CDCl$_3$) δ8.79 (s, 1H), 7.83 (s, 1H), 7.30–7.15 (m, 8H), 7.08 (m, 2H), 5.23 (s, 2H), 5.14 (d, 1H, J=9 Hz), 4.52 (m, 1H), 3.92–3.72 (m, 3H), 3.65 (m, 1H), 2.85 (d-apparent, 2H, J=7.5 Hz), 2.72 (d-apparent, 2H, J=7 Hz), 1.61 (m, 2H), 1.38 (s, 9H). CIMS m/z (526) (M+H)$^+$, 543 (M+18)$^+$.

EXAMPLE 69B (2S,3S,5S)-5-Amino-2-(N-((5-thiazolyl)methoxycarbonyl)amino)-1,6-diphenyl-3-hydroxyhexane The product of Example 69A (6.43 g, 12.23 mmoles) was dissolved in 25 mL dioxane at room temperature under nitrogen atmosphere. To this stirred solution was added 20.25 mL of 4N HCl in dioxane, and after approximately 10 min thick precipitate formed. An additional 10 mL of dioxane was added to loosen up the slurry. This mixture was stirred for 1 h and then filtered. The filter cake of the product bis-HCl salt was washed with 20 mL dioxane, air dried, and then dissolved in 175 mL water. To this solution was added 175 mL ethyl acetate and the two phase mixture rapidly stirred. The pH of this mixture was adjusted to pH=10 by the dropwise addition of 3N NaoH to the rapidly stirred mixture. The organic layer was isolated, washed with brine (150 mL), and dried over Na$_2$SO$_4$. The solvent was removed to afford 5.18 g (99%) of the desired product as a clear oil. H$^1$ NMR (CDCl$_3$) δ8.81 (s, 1H), 7.87 (s, 1H), 7.35–7.05 (m, 10H), 5.33 (d, 1H, J=9.3 Hz), 5.28 (m,2H), 3.81 (m, 1H), 3.72 (m, 1H), 3.01 (m, 1H), 2.88 (m, 2H), 2.78 (dd, 1H, J=13.5, 5.1 Hz), 2.39 (dd, 1H, J=9.0, 4.5 Hz), 1.57–1.30 (m, 2H). CIMS m/z 426 (M+H)$^+$.

EXAMPLE 69C (2S,3S,5S)-5-(N-(N-((N-Methyl-N-((2-isopropyl-4-thiazolyl)methyl)amino)carbonyl)valinyl)amino)-2-(N-((5-thiazolyl)methoxycarbonyl)amino)-1,6-diphenyl-3-hydroxyhexane N-((N-Methyl-N-((2-isopropyl-4-thiazolyl)methyl)amino)carbonyl)-L-valine (4.13 g, 13.18 mmole) and hydroxybenztriazole (2.23 g, 16.48 mmoles) were dissolved in 70 mL THF and then dicyclohexyl-carbodiimide (2.71 g, 13.18 mmoles) was added in one portion to the stirred solution under nitrogen atmosphere. This mixture was stirred for 4 h at room temperature and then filtered to remove dicyclohexylurea precipitate. The product of Example 69B (5.1 g, 11.99 mmoles) was dissolved in 100 mL THF under nitrogen atmosphere. To this stirred solution was added the filtrate of HOBT-active ester and the resulting solution was stirred at room temperature for 4 h, and the solvent removed via rotary evaporation. The residue was dissolved in 150 mL ethyl acetate and washed with 2×100 mL 1N NaOH, 100 mL brine, 100 mL of 1% w/w aqueous KHSO$_4$ and the solvent was removed by rotary evaporation to afford a residue. The residue was dissolved in 175 mL 1N HCL, and the solution filtered to remove the small quantity of dicyclohexylurea. The filtrate solution was added to 175 mL ethyl acetate and the two phase mixture rapidly mixed. The pH of this rapidly stirred mixture was adjusted to pH=7 by dropwise addition of cold 3N NaOH. The organic layer was isolated, washed with 100 mL brine, dried over Na$_2$SO$_4$, filtered, and the solvent was removed to afford 8.6 g of a colorless foam. This material was crystallized from 42 mL EtOAc and 21 mL hexane to give 7.85 g of the desired product as a white solid. mp=122°–123° C. CIMS m/z 721 (M+H)$^+$.

EXAMPLE 70

Alternative Preparation of (2S,3S,5S)-5-Amino-2-(N-((5-thiazolyl)methoxycarbonyl)amino)-1,6-diphenyl-3-hydroxyhexane Alternative A The product of Example 66F (9.5 g, 33.4 mmol) and phenylboronic acid (4.1 g, 33.6 mmol) were combined in toluene (150 mL) and refluxed for 2.5 hours with azeotropic water removal (Dean-Stark trap). Toluene (100 mL) was distilled out at atmospheric pressure, then the remaining toluene was removed under vacuum, to provide a yellow syrup which was dissolved in DMF (50 mL) and cooled to −60° C. A solution of 5-(p-nitrophenyloxycarbonyloxy-methyl)thiazole (9.5 g, 33.5 mmol)in DMF (50 mL) was added over 45 minutes. The resulting mixture was stirred for 8 hours at −55°±5° C., then 14 hours at −25° C., then was allowed to warm to room temperature. The reaction mixture was diluted with 1N HCl (250 mL) and washed with $CH_2Cl_2$ (2×80 mL). The combined organic layers were back-extracted with 1N HCl (60 mL). The combined aqueous HCl layers were cooled in an ice-bath to 2° C., and conc. (37%) HCL (30 mL) was added over 5 minutes. The desired product (bis HCl salt) began to precipitate within 30 minutes. The slurry was stirred 3 hours at 2°–5° C., then the product (bis HCl salt) was collected by filtration and dried in a vacuum oven at 55°–60° C. Yield 11.4 g (68%).

Second crop recovery:

The HCl mother liquors were stirred with ethyl acetate (190 mL) and neutralized to pH 9–10 with aqueous $K_2CO_3$ (200–300 g of 25% w/w $K_2CO_3$ was required). The ethyl acetate layer was concentrated under vacuum to an oil which was redissolved in 1N HCl (90 mL) and washed with methylene chloride (45 mL). The aqueous layer was cooled to 2° C. Conc. (37%) HCl (9.0 mL) was added to precipitate a second crop. After stirring for 1–3 hours at 2°–5° C., the solid was collected by filtration and dried in a vacuum oven at 55°–60° C. Yield 2.1 g (12.6%).

Neutralization of Bis HCl Salt:

The bis HCl salt (10.66 g, 21.4 mmol, mixture of first and second crops) was stirred with $CH_2Cl_2$ (110 mL) and 5% aqueous $NaHCO_3$ (110 mL) until all solids dissolved (2 hours). The aqueous layer was separated and extracted with another 50 mL $CH_2Cl_2$. The combined organic extracts were dried with $Na_2SO_4$ (10 g), filtered and concentrated under vacuum at ≦40° C. to an oil. The oil was dried on a vacuum pump to give the title compound as a yellow foam, 9.1 g (100%).

Alternative B

The product of Example 66F (15.0 g, 0.053 mole) was dissolved in DMF (75 mL). Triisopropylborate (24.4 mL, 0.105 mole) was added and stirred at ambient temperature for approximately 1.5 hours. The solution was cooled to −10° C. and a solution of 5-(p-nitrophenyloxycarbonyloxymethyl)thiazole (15.0 g, 0.054 mole)in DMF (75 mL) was added over 80 minutes. The reaction was stirred for approximately 1 hour at −10° C., then was diluted with methylene chloride (250 mL) and quenched with a mixture of triethanolamine (24.8 g) and 5% aqueous sodium bicarbonate (300 mL). The biphasic mixture was stirred for 1 hour, then the layers were separated and the aqueous layer was extracted with another portion of methylene chloride (50 mL). The combined organic layers were extracted with 1N HCl (1×390 mL, then 1×95 mL). The acid layers were combined, cooled in an ice-bath, and further acidified with conc. HCl (50 mL) which produced a white slurry of product. The slurry was stirred for approximately 1 hour at 2° C. The desired product bis HCl salt was collected by filtration and dried at 55° C. in a vacuum oven. Yield 18.5 g (70%).

EXAMPLE 71

Alternative Preparation of (2S,3S,5S)-5-(N-(N-((N-Methyl-N-((2-isopropyl-4-thiazolyl)methyl)amino)carbonyl)valinyl)amino)-2-(N-((5-thiazolyl)methoxycarbonyl)amino)-1,6-diphenyl-3-hydroxyhexane To a solution of the product of Example 70 (9.1 g, 21.4 mmol), HOBT (3.6 g, 23.5 mmol) and N-((N-Methyl-N-((2-isopropyl-4-thiazolyl)methyl)amino)-carbonyl)-L-valine (7.37 g, 23.5 mmol)in THF (170 mL) was added DCC (4.85 g, 23.5 mmol). The solution was stirred at ambient temperature for 16 hours (DCU precipitates). THF was removed under vacuum and the resulting paste was stirred with cold 1N HCl (106 mL at 5° C.) for 3 hours to dissolve the crude product. The DCU was removed by filtration and the filter cake was washed with 1N HCl (30 mL). $KH_2PO_4$ (3.2 g) was dissolved in the combined HCl filtrates. The solution was mixed with ethyl acetate (80 mL) and neutralized to pH 7 with aqueous NaOH (60.3 g of 10% w/w NaOH). The aqueous layer was extrated with another 25 mL ethyl acetate and the combined ethyl acetate extracts were washed with aqueous $NaHCO_3$ (2×37 mL of 5% w/w $NaHCO_3$). The organic layer was dried with $Na_2SO_4$ (13 g), filtered, and concentrated under vacuum at ≦45° C. The residue was dissolved in a 1:1 ethyl acetate/heptane mixture (200 mL) at 70° C. The solution was allowed to cool slowly and stirred overnight at room temperature to provide a thick slurry. The product was collected by filtration and washed with 1:1 ethyl acetate/heptane (20 mL). The product was dried briefly at 55° C. in a vacuum oven to obtain an approximate weight prior to the second crystallization (12.85 g, 83%).

A second crystallization from 144 mL of 2:1 ethyl acetate/heptane (dissolved at ~70° C., then stirred at room temperature 10 hours) produced a thick slurry of fine white solid. The product was collected by filtration and washed with 15 mL 2:1 ethyl acetate/heptane, then dried in a vacuum oven at 55° C. for 2 days to give the desired product. Yield 11.9 g (77%).

EXAMPLE 72

Alternate Preparation of ((5-Thiazolyl)methyl)-(4-nitrophenyl)carbonate

EXAMPLE 72A

2-Amino-5-(ethoxycarbonyl)thiazole Hydrochloride

To a −10° C. solution of potassium tert-butoxide (110 g, 0.98 mol) in THF (1.9 L) was added a solution of ethyl chloroacetate (100 mL, 0.934 mol) and ethyl formate (75 mL, 0.928 mol) in THF (400 mL) dropwise over 2 hours, with good mechanical stirring. The thick solution was stirred another 2 hours at ca. −1° C. then the reaction was quenched by addition of a solution of NaCl (150 g) in 1N HCL (750 mL). The mixture was allowed to warm to 20° C. and the lower aqueous layer (containing some precipitated salt) was separated. The organic layer was stripped under vacuum on a rotary evaporator. The oil was redissolved in 500 mL ethyl acetate, dried with 75 g $Na_2SO_4$ for 1 hour, filtered and concentrated under vacuum (40°–50° C. bath temperature)

to an oil. The resulting crude chloroaldehyde (161 g) and thiourea (70 g, 0.92 mol) were dissolved in THF (2 L) and warmed to gentle reflux (60° C.). The thiourea dissolved during warming, and within 20 minutes, product precipitated from solution. After 100 minutes the suspension was allowed to cool to room temperature, then was cooled in an ice-bath for 1 hour. The product was collected on a fritted Buchner funnel and washed with 2×100 mL cold THF, then dried overnight in a vacuum oven at 50° C. Yield: 122 g of title compound as a tan-colored solid, m.p. 182°–185° C. (dec.). $^1$H NMR (DMSO-$d_6$) $\delta$7.86 (s, 1H), 4.19 (q, 2H), 1.21 (t, 3H). $^{13}$C NMR (DMSO-$d_6$) $\delta$171.9, 160.4, 140.4, 114.4, 61.1, 14.2.

EXAMPLE 72B

2-Amino-5-(ethoxycarbonyl)thiazole

To a −10° C. solution of potassium tert-butoxide (150 g, 1.3 mol) in THF (1.35 L) was added a solution of ethyl chloroacetate (139 mL, 1.3 mol) and ethyl formate (103 mL, 1.27 mol) in THF (150 mL) dropwise over 75 minutes, with good mechanical stirring. A THF rinse (25 mL) was added over 5 minutes. The thick solution was stirred another 3 hours at ca. −5° to 0° C., then the reaction was quenched by addition of a solution of NaCl (240 g) and conc. HCl (90 mL) in water (960 mL). The mixture was allowed to warm to 15° C. and the lower aqueous layer was discarded. Thiourea (97 g, 1.27 mol) was dissolved in the crude THF solution of chloroaldehyde. The solution was warmed to 65° C. and refluxed for 1 hour, then cooled to 30° C. Addition of a solution of $K_2CO_3$ (88 g, 0.64 mol) in 1500 mL water produced two layers (aqueous pH=7). The THF was removed under vacuum at ≦45° C., causing the product to precipitate as a yellow solid. The slurry was cooled to 15° C., and the product was collected on a fritted Buchner funnel and washed with 3×200 mL water, then dried 24 hours in a vacuum oven at 55° C. to provide 151 g of title compound as a yellow solid, m.p. 155°–158° C. $^1$H NMR (DMSO-$d_6$) $\delta$7.8 (br s, 2H, $NH_2$), 7.62 (s, 1H), 4.13 (q, 2H), 1.18 (t, 3H). $^{13}$C NMR (DMSO-$d_6$) $\delta$173.4, 161.3, 147.9, 114.5, 60.1, 14.3.

EXAMPLE 72C.

5-(Ethoxycarbonyl)thiazole

A solution of 2-amino-5-(ethoxycarbonyl)thiazole (50 g, 0.29 mmol) in a mixture of DMF (83 mL) and THF (317 mL) was added dropwise over 87 minutes to a stirred 41° C. solution of isoamyl nitrite (59 mL, 0.44 mol) in DMF (130 mL). A maximum temperature of 60° C. was observed during the exothermic addition. After another 40 minutes the THF was removed under vacuum at 45° C. The concentrated DMF solution was cooled to 25° C. and diluted with toluene (420 mL) and water (440 mL). The toluene layer was extracted with 3×120 mL water, then dried with $Na_2SO_4$ (50 g) for 1 hour. After filtration the toluene layer was stripped on a rotary evaporator at 50° C. bath temperature, then on a vacuum pump at 21° C. The crude residue containing the title compound weighed 65.6 g. This material was used directly in the next step. A sample of similarly prepared material was purified by column chromatography to give a yellow oil. $^1$H NMR (CDCl$_3$) $\delta$8.95 (s, 1H), 8.51 (s, 1H), 4.39 (q, 2H), 1.40 (t, 3H). $^{13}$C NMR (CDCl$_3$) $\delta$161.0, 157.9 148.6, 129.8, 61.6, 14.1.

EXAMPLE 72D 5-(Hydroxymethyl)thiazole

To a slurry of lithium aluminum hydride (9.0 g) in THF (633 mL) was added a solution of crude 5-(ethoxycarbonyl)thiazole (65.6 g from Example 72C) in THF (540 mL) over 95 minutes at 0°–5° C. After an additional 25 minutes, the reaction was quenched at 5° C. by sequential addition of water (8.1 mL), 15% NaOH (8.1 mL), and water (24.3 mL). After drying with $Na_2SO_4$ (44 g) for 2 hours, the slurry was filtered, and the filter cake was washed with 100 mL THF. The combined filtrates were concentrated under vacuum at 45° C. to a brown oil (39 g). The oil was fractionally distilled through a short-path apparatus. The product fractions distilled at 97°–104° C. vapor temperature at 3–5 mm, providing 20.5 g of the title compound as a turbid orange oil. $^1$H NMR (CDCl$_3$) $\delta$8.74 (s, 1H), 7.72 (s, 1H), 4.89 (s, 2H), 3.4 (br s, 1H, OH). $^{13}$C NMR (CDCl$_3$) $\delta$153.4, 140.0, 139.5, 56.6.

EXAMPLE 72E 5-(p-Nitrophenyoxycarbonyloxymethyl)thiazole Hydrochloride

Distilled 5-(hydroxymethyl)thiazole (14.1 g, 123 mmol) and triethylamine (17.9 mL, 129 mmol) were dissolved in ethyl acetate (141 mL) and cooled to −1° C. (ice/salt bath). A solution of 4-nitrophenyl chloroformate (26.0 g, 129 mmol) dissolved in ethyl acetate (106 mL) was added dropwise over 50 minutes at an internal temperature of 0°–4° C. An ethyl acetate flask rinse (20 mL) was also added. Salts precipitated from solution throughout the addition. The yellow mixture was stirred another 1 hour 45 minutes at 0°–2° C., then a solution of dilute HCl (3.1 g, 31 mmol of conc. HCl in 103 mL water) was added at once. The mixture was stirred for 0.5 hours while warming to 15° C., then stirring was stopped. The organic layer was washed twice with aqueous 5% $K_2CO_3$ solution (2×70 mL), then dried with $Na_2SO_4$ (30 g). After filtration the solution was concentrated under vacuum on a rotary evaporator (bath temperature of 41° C.) to a brown oil (38 g). The crude 5-(p-nitrophenyoxycarbonyloxymethyl)-thiazole was dissolved in ethyl acetate (282 mL), then cooled in an ice bath to 2° C. Dry HCl gas (7.1 g, 195 mmol) was bubbled in slowly over 50 minutes (temperature 2°–4° C.). After stirring for another 1 hour 45 minutes at 2°–4° C., the solid precipitate was collected on a sintered glass funnel under a nitrogen blanket and the flask was washed out with 50 mL cold ethyl acetate which was used to rinse the filter cake. The cake was dried on the funnel under strong nitrogen purge for 15 minutes then dried in a vacuum oven at 50° C. with a nitrogen purge to provide 29.05 g of the title compound as tan powder, m.p. 131°–135° C. (dec.). $^1$H NMR (DMSO-$d_6$) $\delta$9.21 (d, 1H), 8.27 (m, 2H), 8.06 (d, 1H), 7.52 (m, 2H), 5.54 (s, 2H). $^{13}$C NMR (DMSO-$d_6$) $\delta$157.3, 155.2, 151.8, 145.3, 143.7, 131.9, 125.5, 122.7, 62.1.

EXAMPLE 72E 5-(D-Nitrophenoxycarbonyloxymethyl)thiazole 5-(p-Nitrophenoxycarbonyloxymethyl)thiazole hydrochloride (3.0 g) was slurried in ethyl acetate (30 mL) and cooled to 10°–15° C. A solution of 5% aqueous potassium carbonate (30 mL) was added with rapid stirring. After 15 minutes, stirring was stopped and the aqueous layer was separated. The organic layer was dried with $Na_2SO_4$ (3 g), filtered, and solvent was distilled under vacuum to give 2.49 g of the title compound as a brown syrup which slowly solidified, m.p. 62°–64° C. $^1H$ NMR ($CDCl_3$) δ8.90 (d, 1H), 8.29 (m, 2H), 8.01 (d, 1H), 7.39 (m, 2H), 5.52 (s, 2H). $^{13}C$ NMR ($CDCl_3$) δ155.4, 155.2, 152.2, 145.4, 144.9, 130.6, 125.3, 121.6, 61.9.

EXAMPLE 73

Alternative Preparation of N-((N-Methyl-N-((2-isopropyl-4-thiazolyl)methyl)amino)carbonyl)-L-valine

EXAMPLE 73A

Thioisobutyramide

To a 1 liter three neck round bottom flask equipped with mechanical stirrer, nitrogen atmosphere, condensor, thermocouple and 15° C. water bath was charged (26.0 g, 0.298 mols) isobutyramide followed by (19.9 g, 0.045 mols) phosphorous pentasulfide and 375 mls THF. This solution was stirred at 20°±5° C. for 3 hours, then was warmed to 60° C. and stirred an additional 3 hours. The THF was removed under vacuum with a 50° C. bath temperature to afford a yellow oil. This oil was neutralized with a solution of 5 g NaOH, 10 g NaCl and 90 g water. Next the product was extracted into EtOAc (2×250 mls) and the combined organics reduced under vacuum to an oil. The oil was dissolved in 50 mls THF and again the solvent was removed under vacuum to give the desired product as a yellow oil. (yield approx. 27 grams, 88%).

EXAMPLE 73B

2-Isopropyl-4-(((N-methyl)amino)methyl)thiazole

The thioisobutyramide resulting from Example 73A was dissolved in 70 mls THF and added slowly to a solution of (34.1 g, 0.27 mole) 1,3-dichloracetone in 40 mls THF. A 10 ml rinse of THF was used to completely transfer the thioamide. The reaction was carried out in a 250 ml flask with mechanical stirring under nitrogen atmosphere. The reaction temperature was maintained below 25° C. during addition with a 15°±5° C. bath. The bath was kept in place for 1 hour after which it was removed and the reaction stirred for 18 hours. Next this stirred chloromethyl-thiazole solution was added to 376 mls (4.37 mole) 40% aqueous methylamine solution at 15° C. in a 1 liter flask. The temperature was maintained below 25° C. during addition. After half an hour the bath was removed and the reaction stirred for 3 hours at ambient temperature. The solvent was removed under vacuum with a 50° C. bath to an end volume of 310 mls. The residue was then basified with 50 g 10% NaOH to pH 12 and extracted into methylene chloride (2×160 mls). The combined organics were then washed with 1×150 g of 20% ammonium chloride followed by 1×90 g of 20% ammonium chloride. The combined aqueous washes were then back extracted with 150 mls methylene chloride. The combined product methylene chloride layers were then extracted with 100 g of a solution of 25 g conc. HCl and 75 g water. This acidic product solution was then washed with 135 mls methylene chloride. Next the acidic product solution was cooled, then neutralized with 100 g 20% NaOH solution. The product was extracted from this mixture with methylene chloride (2×135 mls). The solvent was removed under vacuum to afford the desired product as an amber oil. (yield approx. 28 grams)

EXAMPLE 73C

N-((N-Methyl-N-((2-isopropyl-4-thiazolyl)methyl)amino)carbonyl)-L-valine Methyl Ester Into a 500 ml 3-neck round bottom flask equipped with mechanical stirrer, nitrogen atmosphere, thermocouple, heating mantle and condensor was charged the product of Example 73B (28.1 g, 0.165 mole), phenoxycarbonyl-(L)-valine (41.5 g, 0.165 mol) and 155 ml toluene. This solution was warmed to reflux (110° C.) and stirred for three hours, then cooled to 20°±5° C. and washed with 2×69 ml 10% citric acid followed by 1×69 ml water, 1×116 mls 4% sodium hydroxide, 1×58 ml 4% sodium hydroxide and finally 1×58 ml water. The organic product solution was then treated with 3 grams of activated carbon at reflux for 15 minutes, filtered through infusorial earth to remove carbon, and the carbon/infusorial earth cake was washed with 25 ml hot toluene. Next the solvent was removed to afford a brown oil which solidired upon cooling. This brown solid was dissolved with warming in 31 ml EtOAc and 257 ml heptane at 60°±5° C. This solution was slowly cooled to 25° C., stirred 12 hours, cooled further to 0° C., and stirred 3 hours. The crystals were collected by filtration and washed with 50 ml 1:9 EtOAc/Heptane. The solid was dried in a 50° C. vacuum oven for 12 hours to afford 41.5 grams of the desired product as a tan-colored solid (76.9%).

EXAMPLE 73D

N-((N-Methyl-N-((2-isopropyl-4-thiazolyl)methyl)amino)carbonyl)-L-valine

To a one liter three neck flask was charged the product of Example 73C (50 g, 0.153 mol), lithium hydroxide monohydrate (13 g, 0.310 mol), 200 ml THF and 190 ml water. This hazy solution was stirred for 2 hours. The reaction was quenched with a solution of conc. HCl (32.4 g, 0.329 mol) in 65 mL water, the THF was removed under vacuum and the product extracted into methylene chlodde (3×210 ml). (NOTE: If necessary, the pH of the aqueous layer should be adjusted to maintain pH 1–4 during the extractions.) The combined organics were then dried with 50 g sodium sulfate, filtered with a 150 ml methylene chloride rinse of the sodium sulfate, and the solvent was removed under vacuum. The product was dissolved in 450 ml THF and again the solvent was removed. Next the product was dissolved in 475 ml THF containing 0.12 g butylated hydroxytoluene (BHT) for storage. If desired, the solvent can be removed under vacuum and the residual syrup dried in a vacuum oven at 55° C. to provide a glassy solid.

Flurogenic Assay for Screening Inhibitors of HIV Protease

The inhibitory potency of the compounds of the invention can be determined by the following method.

A compound of the invention is dissolved in DMSO and a small aliquot further diluted with DMSO to 100 times the final concentration desired for testing. The reaction is carried out in a 6×50 mm tube in a total volume of 300 microliters. The final concentrations of the components in the reaction buffer are: 125 mM sodium acetate, 1M sodium chloride, 5 mM dithiothreitol, 0.5 mg/ml bovine serum albumin, 1.3 µM fluorogenic substrate, 2% (v/v) dimethylsulfoxide, pH 4.5. After addition of inhibitor, the reaction mixture is placed in the fluorometer cell holder and incubated at 30° C. for several minutes. The reaction is initiated by the addition of a small aliquot of cold HIV protease. The fluorescence intensity excitation 340 nM, emmision 490 nM) is recorded as a function of time. The reaction rate is determined for the first six to eight minutes. The observed rate is directly proportional to the moles of substrate cleaved per unit time. The percent inhibition is 100×(1−(rate in presence of inhibitor)/(rate in absence of inhibitor)).

Fluorogenic substrate: Dabcyl-Ser-Gln-Asn-Tyr-Pro-Ile-Val-Gln-EDANS wherein DABCYL=4-(4-dimethylaminophenyl)azobenzoic acid and EDANS=5-((2-aminoethyl)amino)-naphthalene-1-sulfonic acid.

Table 1 shows the inhibitory potencies of compounds of the invention against HIV-1 protease.

TABLE 1

| Compound of Example | Percent Inhibition | Inhibitor Concentration (nanomolar) |
|---|---|---|
| 1 | 79 | 0.5 |
| 3 | 70 | 0.5 |
| 4 | 72 | 0.5 |
| 5 | 79 | 0.5 |
| 6 | 75 | 0.5 |
| 7 | 74 | 0.5 |
| 9 | 64 | 0.5 |
| 10 | 56 | 0.5 |
| 11 | 71 | 0.5 |
| 12 | 72 | 0.5 |
| 13 | 46 | 0.5 |
| 14 | 61 | 0.5 |
| 15 | 57 | 0.5 |
| 17 | 66 | 0.5 |
| 18 | 80 | 0.5 |
| 19 | 70 | 0.5 |
| 20 | 86 | 0.5 |
| 26 | 71 | 0.5 |
| 27 | 82 | 0.5 |
| 28 | 68 | 0.5 |
| 39 | 63 | 0.5 |
| 41 | 75 | 0.5 |
| 42 | 70 | 0.5 |
| 44 | 68 | 0.5 |
| 45 | 50 | 0.5 |
| 46 | 46 | 0.5 |
| 47 | 73 | 0.5 |
| 48 | 69 | 0.5 |
| 49 | 55 | 0.5 |
| 50 | 61 | 0.5 |
| 51 | 69 | 0.5 |
| 52 | 71 | 0.5 |
| 53 | 75 | 0.5 |
| 54 | 50 | 0.5 |
| 55 | 54 | 0.5 |
| 56 | 66 | 0.5 |
| 57 | 64 | 0.5 |
| 58 | 49 | 0.5 |
| 59 | 39 | 0.5 |
| 60 | 44 | 0.5 |
| 61 | 69 | 0.5 |
| 62 | 54 | 0.5 |
| 63 | 61 | 0.5 |
| 64 | 52 | 0.5 |
| 65 | 70 | 0.5 |

Antiviral Activity

The anti-HIV activity of the compounds of the invention can be determined in MT4 cells according to the procedure of Kempf, et. al. (*Antimicrob. Agents Chemother.* 1991, 35, 2209). The $IC_{50}$ is the concentration of compound that gives 50% inhibition of the cytopathic effect of HIV. The $LC_{50}$ is the concentration of compound at which 50% of the cells remain viable.

Table 2 shows the inhibitory potencies of compounds of the invention against HIV-$1_{3B}$ in MT4 cells.

TABLE 2

| Compound of Example | $IC_{50}$ (micromolar) | $LC_{50}$ (micromolar) |
|---|---|---|
| 1 | 0.025–0.040 | 55 |
| 3 | 0.041–0.075 | 52 |
| 4 | 0.17–0.32 | 29 |
| 5 | 0.003–0.009 | 51 |
| 6 | 0.006–0.014 | 100 |
| 7 | 0.076–0.131 | 56 |
| 8 | 0.057–0.095 | 97 |
| 9 | 0.080–0.10 | 62 |
| 10 | 0.054–0.071 | 55 |
| 11 | 0.017–0.132 | 60 |
| 12 | 0.053–0.106 | >100 |
| 13 | 0.056–0.088 | 56 |
| 14 | 0.14–0.22 | >100 |
| 15 | 0..43–0.67 | 41 |
| 17 | 0.23–0.31 | 19 |
| 18 | 0.039–0.046 | 62 |
| 19 | 0.022–0.048 | 87 |
| 20 | 0.011–0.014 | 55 |
| 26 | 0.007–0.011 | 28 |
| 27 | 0.011–0.012 | 57 |
| 28 | 0.11–0.12 | 18 |
| 39 | 0.073–0.077 | 22 |
| 41 | 0.015–0.02 | 100 |
| 42 | 0.073–0.08 | >100 |
| 44 | 0.12–0.16 | 19 |
| 45 | 0.036–0.040 | 19 |
| 46 | 0.10–0.17 | 61 |
| 47 | 0.009–0.024 | 25 |
| 48 | 0.09–0.11 | >100 |
| 49 | 0.081–0.13 | 38 |
| 50 | 0.15–0.27 | >100 |
| 51 | 0.045–0.049 | 48 |
| 52 | 0.035–0.042 | 26 |
| 53 | 0.032–0.073 | 59 |
| 54 | 0.11–0.17 | 19 |
| 55 | 0.14–0.22 | 17 |
| 56 | 0.05–0.067 | 100 |
| 57 | 0.035–0.048 | >100 |
| 58 | 0.03–0.046 | 18 |
| 59 | 0.11–0.13 | 18 |
| 60 | 0.34–0.51 | 17 |
| 61 | 0.15–0.22 | 25 |
| 62 | 0.69–1.0 | 17 |
| 63 | 0.13–0.18 | 45 |
| 64 | 0.10–0.13 | >100 |
| 65 | 0.12–0.20 | >100 |

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other salts include salts with alkali metals or alkaline earth metals, such as sodium, potassium, calcium or magnesium or with organic bases.

Preferred salts of the compounds of the invention include hydrochloride, methanesulfonate, sulfonate, phosphonate and isethionate.

The compounds of the present invention can also be used in the form of esters. Examples of such esters include a hydroxyl-substituted compound of formula A or A1 or A2 which has been acylated with a blocked or unblocked amino acid residue, a phosphate function, a hemisuccinate residue, an acyl residue of the formula R*C(O)— or R*C(S)— wherein R* is hydrogen, loweralkyl, haloalkyl, alkoxy, thioalkoxy, alkoxyalkyl, thioalkoxyalkyl or haloalkoxy, or an acyl residue of the formula $R_a$—$C(R_b)(R_d)$—C(O)— or $R_a$—$C(R_b)(R_d)$—C(S)— wherein $R_b$ and $R_d$ are independently selected from hydrogen or loweralkyl and $R_a$ is —$N(R_e)(R_f)$, $OR_e$ or —$SR_e$ wherein $R_e$ and $R_f$ are independently selected from hydrogen, loweralkyl and haloalkyl, or an amino-acyl residue of the formula $R_{180}NH(CH_2)_2NHCH_2C(O)$— or $R_{180}NH(CH_2)_2OCH_2C(O)$— wherein $R_{180}$ is hydrogen, loweralkyl, arylalkyl, cycloalkylalkyl, alkanoyl, benzoyl or an a-amino acyl group. The amino acid esters of particular interest are glycine and lysine; however, other amino acid residues can also be used, including those wherein the amino acyl group is —$C(O)CH_2NR_{200}R_{201}$ wherein $R_{200}$ and $R_{201}$ are independently selected from hydrogen and loweralkyl or the group —$NR_{200}R_{201}$ forms a nitrogen containing heterocyclic ring. These esters serve as pro-drugs of the compounds of the present invention and serve to increase the solubility of these substances in the gastrointestinal tract. These esters also serve to increase solubility for intravenous administration of the compounds. Other prodrugs include a hydroxyl-substituted compound of formula A or A1 or A2 wherein the hydroxyl group is functionalized with a substituent of the formula —$CH(R_g)OC(O)R_{181}$ or —$CH(R_g)OC(S)R_{181}$ wherein $R_{181}$ is loweralkyl, haloalkyl, alkoxy, thioalkoxy or haloalkoxy and $R_g$ is hydrogen, loweralkyl, haloalkyl, alkoxycarbonyl, aminocarbonyl, alkylaminocarbonyl or dialkylaminocarbonyl. Such prodrugs can be prepared according to the procedure of Schreiber (Tetrahedron Lett. 1983, 24, 2363) by ozonolysis of the corresponding methallyl ether in methanol followed by treatment with acetic anhydride.

The prodrugs of this invention are metabolized in vivo to provide the hydroxyl-substituted compound of formula A or A1 or A2. The preparation of the prodrug esters is carried out by reacting a hydroxyl-substituted compound of formula A or A1 or A2 with an activated amino acyl, phosphoryl, hemisuccinyl or acyl derivative as defined above. The resulting product is then deprotected to provide the desired pro-drug ester. Prodrugs of the invention can also be prepared by alkylation of the hydroxyl group with (haloalkyl)esters, transacetalization with bis-(alkanoyl)acetals or condensation of the hydroxyl group with an activated aldehyde followed by acylation of the intermediate hemiacetal.

The compounds of the invention are useful for inhibiting retroviral protease, in particular HIV protease, in vitro or in vivo (especially in mammals and in particular in humans). The compounds of the present invention are also useful for the inhibition of retroviruses in vivo, especially human immunodeficiency virus (HIV). The compounds of the present invention are also useful for the treatment or prophylaxis of diseases caused by retroviruses, especially acquired immune deficiency syndrome or an HIV infection in a human or other mammal.

Total daily dose administered to a human or other mammal host in single or divided doses may be in amounts, for example, from 0.001 to 300 mg/kg body weight daily and more usually 0.1 to 10 mg. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend Upon a variety of factors including the activity of the specific compound employed, the age, body weight, general health, sex, diet, time of administration, route of administration, rate of excretion, drug combination, and the severity of the particular disease undergoing therapy.

The compounds of the present invention may be administered orally, parenterally, sublingually, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable inonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically aceptable and metabolizable lipid capabale of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natureal and synthetic.

Methods to form liposomes are known in the art. See, for example, Prescott, Ed., *Methods in Cell Biology*, Volume XIV, Academic Press, New York, N.Y. (1976), p. 33 et seq.

One preferred dosage form for the compounds of the invention comprises a solid dosage form for oral administration comprising a pharmaceutically acceptable adsorbent to which is adsorbed a mixture of (1) a pharmaceutically acceptable organic solvent or a mixture of two or more pharmaceutically acceptable organic solvents, (2) a compound of the invention in the amount of from about 10% to about 40% by weight and (3) a total of from about 0.2 molar equivalents to about 2 molar equivalents (based on the compound of the invention) of a pharmaceutically acceptable acid. This composition is filled into hard gelatin capsules for administration. The preparation of a specific example of this type of dosage form is described below.

Solid-filled Capsule Dosage Form Preparation

Propylene glycol (USP, 139 mL) and ethanol (dehydrated, USP, 200 proof, 139 mL) were mixed in a stainless steel or glass container. Hydrochloric acid (reagent grade, 20 mL) was added and mixed well. To this solution was added ascorbic acid (21 g) and the mixture was stirred until it was clear. The product of Example 1U (200 g) was slowly added to the solution and mixing was continued until the solution was clear. Cremophore® EL (polyoxyethyleneglycerol oxystearate, 41 g) and polysorbate 80, NF (41 g) were added with mixing.

Microcrystalline cellulose, NF (139 g) and silicon dioxide, NF (Syloid 244, pharmaceutical grade, 209 g) were charged into a Hobart mixer and mixed for 3–5 minutes. The above solution was added dropwise to the dry mixture in the Hobart mixer while mixing at slow speed. This mixture was massed until granular.

The wet granulation was screened through an 8 mesh screen. The screened granulation was spread on paper-lined trays and dried in a tray dryer or a fluidbed dryer (20°–35° C.) until the loss on drying was not more than 12%.

The concentration of the product of Example 1U (mg/g of granulation) in the granulation was determined by HPLC analysis. Capsules (gelatin, No. 00, iron gray opaque) were filled with the appropriate amount of the dried granulation to provide the desired dose per capsule.

While the compounds of the invention can be administered as the sole active pharmaceutical agent, they can also be used in combination with one or more immunomodulators, antiviral agents, other antiinfective agents or vaccines. Other antiviral agents to be administered in combination with a compound of the present invention include AL-721, beta interferon, polymannoacetate, reverse transcriptase inhibitors (for example, dideoxycytidine (DDC), dideoxyinosine (DDI), BCH-189, AzdU, carbovir, DDA, D4C, D4T, DP-AZT, FLT (fluorothymidine), BCH-189, 5-halo-3'-thia-dideoxycytidine, PMEA, zidovudine (AZT) and the like), non-nucleoside reverse transcriptase inhibitors (for example, $R_{82193}$, L-697,661, BI-RG-587 (nevirapine), retroviral protease inhibitors (for example, HIV protease inhibitors such as Ro 31-8959, SC-52151, KNI-227, KNI-272 and the like), HEPT compounds, L,697,639, $R_{82150}$, U-87201E and the like), TAT inhibitors (for example, RO-24-7429 and the like), trisodium phosphonoformate, HPA-23, eflonithine, Peptide T, Reticulose (nucleophosphoprotein), ansamycin LM 427, trimetrexate, UA001, ribavirin, alpha interferon, oxetanocin, oxetanocin-G, cylobut-G, cyclobut-A, ara-M, $BW882C_{87}$, foscarnet, BW256U87, BW348U87, L-693,989, BV ara-U, CMV triclonal antibodies, FIAC, HOE-602, HPMPC, MSL-109, TI-23, trifluridine, vidarabine, famciclovir, penciclovir, acyclovir, ganciclovir, castanospermine, rCD4/CD4-1gG, CD4-PE40, butyl-DNJ, hypericin, oxamyristic acid, dextran sulfate and pentosan polysulfate. Immunomodulators that can be administered in combination with a compound of the present invention include bropirimine, Ampligen, anti-human alpha interferon antibody, colony stimulting factor, CL246,738, Imreg-1, Imreg-2, diethydithiocarbamate, interleukin-2, alpha-interferon, inosine pranobex, methionine enkephalin, muramyl-tripeptide, TP-5, erythropoietin, naltrexone, tumor necrosis facator, beta interferon, gamma interferon, interleukin-3, interleukin-4, autologous CD8+ infusion, alpha interferon immunoglobulin, IGF-1, anti-Leu-3A, autovaccination, biostimulation, extracorporeal photophoresis, FK-565, FK-506, G-CSF, GM-CSF, hyperthermia, isopinosine, IVIG, HIVIG, passive immunotherapy and polio vaccine hyperimmunization. Other antiinfective agents that can be administered in combination with a compound of the present invention include pentamidine isethionate. Any of a variety of HIV or AIDS vaccines (for example, gp120 (recombinant), Env 2-3 (gp120), HIVAC-1e (gp120), gp160 (recombinant), VaxSyn HIV-1 (gp160), Immuno-Ag (gp160), HGP-30, HIV-Immunogen, p24 (recombinant), VaxSyn HIV-1 (p24) can be used in combination with a compound of the present invention.

Other agents that can be used in combination with the compounds of this invention are ansamycin LM 427, apurinic acid, ABPP, AI-721, carrisyn, AS-101, avarol, azimexon, colchicine, compound Q, CS-85, N-acetyl cysteine, (2-oxothiazolidine-4-carboxylate), D-penicillamine, diphenylhydantoin, EL-10, erythropoieten, fusidic acid, glucan, HPA-23, human growth hormone, hydroxchloroquine, iscador, L-ofloxacin or other quinolone antibiotics, lentinan, lithium carbonate, MM-1, monolaurin, MTP-PE, naltrexone, neurotropin, ozone, PAI, panax ginseng, pentofylline, pentoxifylline, Peptide T, pine cone extract, polymannoacetate, reticulose, retrogen, ribavirin, ribozymes, RS-47, Sdc-28, silicotungstate, THA, thymic humoral factor, thymopentin, thymosin fraction 5, thymosin alpha one, thymostimulin, UA001, uridine, vitamin B12 and wobemugos.

Other agents that can be used in combination with the compounds of this invention are antifungals such as amphotericin B, clotrimazole, flucytosine, fluconazole, itraconazole, ketoconazole and nystatin and the like.

Other agents that can be used in combination with the compounds of this invention are antibacterials such as amikacin sulfate, azithromycin, ciprofloxacin, tosufloxacin, clarithromycin, clofazimine, ethambutol, isoniazid, pyrazinamide, rifabutin, rifampin, streptomycin and TLC G-65 and the like.

Other agents that can be used in combination with the compounds of this invention are anti-neoplastics such as alpha interferon, COMP (cyclophosphamide, vincristine, methotrexate and prednisone), etoposide, mBACOD (methotrexate, bleomycin, doxorubicin, cyclophosphamide, vincristine and dexamethasone), PRO-MACE/MOPP (prednisone, methotrexate (w/leucovin rescue), doxorubicin, cyclophosphamide, etoposide/mechlorethamine, vincristine, prednisone and procarbazine), vincristine, vinblastine, angioinhibins, pentosan polysulfate, platelet factor 4 and SP-PG and the like.

Other agents that can be used in combination with the compounds of this invention are drugs for treating neurological disease such as peptide T, ritalin, lithium, elavil, phenytoin, carbamazipine, mexitetine, heparin and cytosine arabinoside and the like.

Other agents that can be used in combination with the compounds of this invention are anti-protozoals such as albendazole, azithromycin, clarithromycin, clindamycin, corticosteroids, dapsone, DIMP, eflornithine, 566C80, fansidar, furazolidone, L,671,329, letrazuril, metronidazole, paromycin, pefloxacin, pentamidine, piritrexim, primaquine, pyrimethamine, somatostatin, spiramycin, sulfadiazine, trimethoprim, TMP/SMX, trimetrexate and WR 6026 and the like.

Among the preferred agents for treatment of HIV or AIDS in combination with the compounds of this invention are reverse transcriptase inhibitors.

It will be understood that agents which can be combined with the compounds of the present invention for the treatment or prophylaxis of AIDS or an HIV infection are not limited to those listed above, but include in principle any agents useful for the treatment or prophylaxis of AIDS or an HIV infection.

When administered as a combination, the therapeutic agents can be formulated as separate compositions which are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A process for the preparation of a compound of the formula:

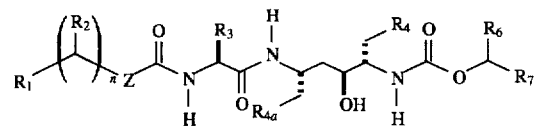

wherein $R_1$ is monosubstituted thiazolyl, monosubstituted oxazolyl, monosubstituted isoxazolyl or monosubstituted isothiazolyl wherein the substituent is selected from $C_1$-to-$C_6$-loweralkyl;

n is 1, 2 or 3;

$R_2$ is hydrogen or $C_1$-to-$C_6$-loweralkyl;

$R_3$ is $C_1$-to-$C_6$-loweralkyl;

$R_4$ and $R_{4a}$ are independently selected from phenyl, thiazolyl and oxazolyl wherein the phenyl, thiazolyl or oxazolyl ring is unsubstituted or substituted with a substituent selected from (i) halo, (ii) $C_1$-to-$C_5$-loweralkyl, (iii) hydroxy, (iv) $C_1$-to-$C_6$-alkoxy or benzyloxy and (v) $C_1$-to-$C_6$-thioalkoxy or benzyl-S-;

$R_6$ is hydrogen or $C_1$-to-$C_6$-loweralkyl;

$R_7$ is thiazolyl, oxazolyl, isoxazolyl or isothiazolyl wherein the thiazolyl, oxazolyl, isoxazolyl or isothiazolyl ring is unsubstituted or substituted with $C_1$-to-$C_6$-loweralkyl; and Z is absent, —O—, —S—, —$CH_2$— or —$N(R_8)$— wherein $R_8$ is $C_1$-to-$C_6$-loweralkyl, $C_3$-to-$C_7$-cycloalkyl, —OH or —$NHR_{8a}$ wherein $R_{8a}$ is hydrogen or $C_1$-to-$C_6$-loweralkyl; or a pharmaceutically acceptable salt thereof, comprising (a) reacting a compound of the formula:

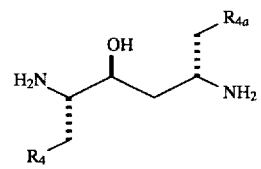

wherein $R_4$ and $R_{4a}$ are as defined above with Ti(OR**)$_4$ wherein R** is $C_1$-to-$C_6$-loweralkyl, followed by reaction with a compound of the formula:

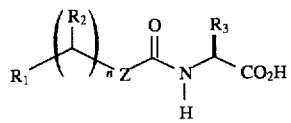

or an activated ester derivative thereof, wherein $R_1$, $R_2$, $R_3$, Z and n are as defined above to give a compound of the formula:

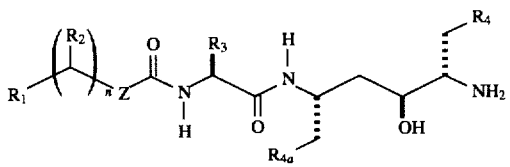

and (b) acylation of the product of step (a) with a compound of the formula ($R_6$)($R_7$)CHOC(O)OL wherein L is an activating group for the acylation reaction and wherein $R_6$ and $R_7$ are defined as above.

2. The process of claim 1 wherein $R_1$ is $C_1$-to-$C_6$-loweralkyl-substituted thiazolyl, $R_2$ is hydrogen, $R_3$ is $C_1$-to-$C_6$-loweralkyl, $R_{4a}$ and $R_4$ are phenyl, $R_6$ is hydrogen, $R_7$ is thiazolyl and n is 1.

3. The process of claim 1 wherein R**** is isopropyl.

4. The process of claim 1 wherein $R_1$ is 2-isopropyl-4-thiazolyl, n is 1, $R_2$ is hydrogen, $R_3$ is isopropyl, $R_4$ and $R_{4a}$ are phenyl, $R_6$ is hydrogen, $R_7$ is 5-thiazolyl, Z is —N(CH$_3$)— and R**** is isopropyl.

* * * * *

UNITED STATES PATENT AND TRADEMARK OFFICE
CERTIFICATE OF CORRECTION

PATENT NO. : 5,616,720
DATED : April 1, 1997
INVENTOR(S) : Kempf, et. al.

It is certified that error appears in the above-indentified patent and that said Letters Patent is hereby corrected as shown below:

Column 108, line 1, change "$C_1$-to-$C_5$" to --$C_1$-to-$C_6$--.

Signed and Sealed this

Fifteenth Day of July, 1997

*Attest:*

BRUCE LEHMAN

*Attesting Officer*    *Commissioner of Patents and Trademarks*